US012102418B2

(12) United States Patent
Mocanu et al.

(10) Patent No.: US 12,102,418 B2
(45) Date of Patent: Oct. 1, 2024

(54) MEDICAL DEVICE FOR MONITORING HEALTH PARAMETERS OF A PATIENT AND METHOD OF MONITORING HEALTH PARAMETERS OF A PATIENT

(71) Applicant: CARDIOMEDIVE HEALTHCARE S.R.L., Bucharest (RO)

(72) Inventors: Ion Mocanu, Bucharest (RO); Adrian-Calin Lupu, Jud. Ilfov (RO); Bogdan-Olivian Radu, Bucharest (RO)

(73) Assignee: CARDIOMEDIVE HEALTHCARE S.R.L, Bucharest (RO)

( * ) Notice: Subject to any disclaimer, the term of this patent is extended or adjusted under 35 U.S.C. 154(b) by 0 days.

(21) Appl. No.: 18/308,615

(22) Filed: Apr. 27, 2023

(65) Prior Publication Data

US 2024/0130623 A1 Apr. 25, 2024
US 2024/0225456 A9 Jul. 11, 2024

(51) Int. Cl.
*A61B 5/0205* (2006.01)
*A61B 5/00* (2006.01)
*A61B 5/1172* (2016.01)
*A61B 5/308* (2021.01)
*A61B 5/318* (2021.01)
*A61B 7/00* (2006.01)

(52) U.S. Cl.
CPC ........ *A61B 5/02055* (2013.01); *A61B 5/0002* (2013.01); *A61B 5/1172* (2013.01);
(Continued)

(58) Field of Classification Search
CPC ..... A61B 5/02055; A61B 5/318; A61B 5/308; A61B 5/0002; A61B 5/1172;
(Continued)

(56) References Cited

U.S. PATENT DOCUMENTS 9,717,432 B2    8/2017 Felix
9,833,193 B2 *  12/2017 Bay .......................... A61B 5/24
(Continued)

FOREIGN PATENT DOCUMENTS

EP       2 675 351 B1    6/2021
WO   WO 2017/068573 A1    4/2017
(Continued)

OTHER PUBLICATIONS

Written Opinion for European Patent Application No. 22 171 553.5, completed Oct. 21, 2022 (5 pages).

*Primary Examiner* — Lynsey C Eiseman
*Assistant Examiner* — Amanda L Steinberg
(74) *Attorney, Agent, or Firm* — Nixon Peabody LLP

(57) ABSTRACT

A medical device is directed to monitoring health parameters of a patient, and includes a main unit and a sensor module. The main unit includes mechanical features, a main array interface, and a processor sub-unit, which includes a processor that has communication drivers, a memory, and a sensor module. The sensor module includes a sensor unit, sensor components, enabling components, and a sensor module array interface that mates with the main array interface. In response to the sensor module being electrically and mechanically coupled to the main unit, the medical device acquires one or more bio-signals of the patient. The bio-signals correspond to an anatomic part of the patient and caries out measurements of health parameters.

18 Claims, 29 Drawing Sheets

(52) U.S. Cl.
CPC .............. *A61B 5/308* (2021.01); *A61B 5/318* (2021.01); *A61B 5/6823* (2013.01); *A61B 5/6826* (2013.01); *A61B 5/6828* (2013.01); *A61B 5/6831* (2013.01); *A61B 7/003* (2013.01); *A61B 2562/0204* (2013.01); *A61B 2562/164* (2013.01)

(58) Field of Classification Search
CPC ... A61B 5/6823; A61B 5/6826; A61B 5/6828; A61B 5/6831; A61B 2562/0204; A61B 2562/164; A61B 5/04; A61B 5/0408; A61B 5/0492; A61B 5/6832; A61B 5/0533
See application file for complete search history.

(56) References Cited

U.S. PATENT DOCUMENTS

| | | |
|---|---|---|
| D831,833 S | 10/2018 | Bishay |
| 10,299,691 B2 | 5/2019 | Hughes |
| 10,499,825 B2 | 12/2019 | Solosko |
| 10,537,270 B2 | 1/2020 | Sarussi |
| 11,024,423 B2 | 6/2021 | Reykhert |
| 2013/0211265 A1 | 8/2013 | Bedingham |
| 2014/0275888 A1 | 9/2014 | Wegerich |
| 2017/0238855 A1 | 8/2017 | Hoppe |
| 2017/0251922 A1 | 9/2017 | Roesicke |
| 2018/0085069 A1 | 3/2018 | Murali |
| 2018/0249957 A1 | 9/2018 | Bay |
| 2019/0005596 A1 | 1/2019 | Mansker |
| 2019/0206565 A1 | 7/2019 | Shelton |
| 2020/0178828 A1 | 6/2020 | Bahney |
| 2020/0330037 A1 | 10/2020 | Al-Ali |
| 2021/0000351 A1 | 1/2021 | Murali |
| 2021/0038102 A1 | 2/2021 | Boleyn |
| 2021/0093218 A1 | 4/2021 | Bishay |

FOREIGN PATENT DOCUMENTS

| | | |
|---|---|---|
| WO | WO 2020/095296 A1 | 5/2020 |
| WO | WO 2020/161709 A1 | 8/2020 |

* cited by examiner

| Light Path No. | Light Emitter | Light Sensor | Light Separation Distance No. | Separation Distance unit values | Optimised for Anatomical Place |
|---|---|---|---|---|---|
| 1 | 109-111 | 109-121 | d1 | 6.25 | Arm |
| 2 | 109-111 | 109-122 | d2 | 12.13 | Chest |
| 3 | 109-111 | 109-123 | d3 | 10.31 | Chest |
| 4 | 109-112 | 109-121 | d4 | 7.46 | Arm |
| 5 | 109-112 | 109-122 | d5 | 10.61 | Chest |
| 6 | 109-112 | 109-123 | d6 | 12.82 | Chest |
| 7 | 109-113 | 109-121 | d7 | 6.77 | Arm |
| 8 | 109-113 | 109-122 | d8 | 5.53 | Wrist |
| 9 | 109-113 | 109-123 | d9 | 10.67 | Chest |
| 10 | 109-114 | 109-121 | d2 | 12.13 | Chest |
| 11 | 109-114 | 109-122 | d1 | 6.25 | Arm |
| 12 | 109-114 | 109-123 | d10 | 12.39 | Chest |
| 13 | 109-115 | 109-121 | d11 | 11.15 | Chest |
| 14 | 109-115 | 109-122 | d12 | 5.30 | Wrist |
| 15 | 109-115 | 109-123 | d13 | 9.91 | Chest |
| 16 | 109-116 | 109-121 | d7 | 6.77 | Arm |
| 17 | 109-116 | 109-122 | d8 | 5.53 | Wrist |
| 18 | 109-116 | 109-123 | d14 | 2.58 | Wrist |
| 19 | 109-117 | 109-121 | d4 | 7.46 | Arm |
| 20 | 109-117 | 109-122 | d5 | 10.61 | Chest |
| 21 | 109-117 | 109-123 | d15 | 4.08 | Wrist |
| 22 | 109-118 | 109-121 | d12 | 5.30 | Wrist |
| 23 | 109-118 | 109-122 | d11 | 11.15 | Chest |
| 24 | 109-118 | 109-123 | d16 | 7.49 | Chest |

MEDICAL DEVICE FOR MONITORING HEALTH PARAMETERS OF A PATIENT AND METHOD OF MONITORING HEALTH PARAMETERS OF A PATIENT

CROSS-REFERENCE TO RELATED APPLICATIONS

This application claims priority to and the benefit of European Patent Application No. 22 171 553.5, filed May 4, 2022, which is incorporated by reference in its entirety.

FIELD OF THE INVENTION

The present invention refers to a medical device for monitoring health parameters of a patient.

In particular, the present invention refers to a modular medical device for monitoring health parameters of a patient comprising a sharable main unit and a sensor module, the sensor module selected among a plurality of sensor modules. The invention also refers to a method of monitoring health parameters of a patient using the main unit and one or more sensor modules used successively.

Terms to be used in the invention

The term "sensor" refers to all kind of sensors used to collect health parameter data from a patient. When used alone, the term "sensor" designates any of the sensors of the invention.

The term "sensors' components" refers to parts of the sensors for example: electrodes for electrical skin contact, or, depending on the case, to the sensor in its entirety, for example a photoplethysmography PPG sensor, electrocardiograph ECG sensor, auscultation sensor for stethoscope formed by microphone array, movement sensor formed by gyroscope and accelerometer sensor etc.

The term "monitoring health parameters" includes the measurement of said health parameters either as spot measurements or continuously, for example: measure the electrical heart activity with an electrocardiograph ECG during the doctor's consultation, or as repetitive measurements over a period of time, the periodicity and the duration of measurements as prescribed by the doctor, for example: measure the electrical heart activity with an electrocardiograph ECG for 30 seconds twice per day or continuously for several weeks, for example 14 days.

The term "measurement" refers to the final result of measuring of one health parameter, such as, but not limited to: one lead electrocardiograph ECG, heart rate, blood pressure, oxygenation rate, body temperature, the electrical heart activity. Any type of health parameter that can be measured falls within this category. The term "more measurements" refers to the result of measuring of two or more health parameters.

The term "measurement corresponding to an anatomic part of the patient" refers to the fact that any measurement takes its data from a specific anatomic part of the patient, such as: the chest, fingers, the forehead, arm etc. In some cases, as it will be detailed hereafter, for the same type of measurement, e.g. electrocardiograph ECG and heart rate or blood oxygenation, it is possible to make measurements from more than one anatomic part. The teaching of the invention is not limited to the specific anatomic part of the patient from which the measurements are collected.

The term "example" stands for a non-limiting example for illustrating the teaching of the invention. Given the complexity of the invention, many examples are provided for a better understanding, none of these examples shall limit the invention to its respective content.

BACKGROUND OF THE INVENTION

Increasing pressure on the medical system and the development of telecommunications technologies have led to the development of telemedicine solutions to provide medical services directly to patients' homes without the need that the patients visit to the medical facilities.

Providing remote health care services to the patient implies that the patient handles himself the monitoring of the health parameters and/or the health specialist examines the patient at patient's home using clinical remote examination devices.

Traditionally, said examination, diagnostic or monitoring being was done at the doctor's office by health specialists like a doctor or a nurse, using multiple specialized medical devices. Providing remote health care services requires telecommunication capabilities to transmit and, respectively, to receive the measurements data and to store them to a storing device external to the patient's home or to allow viewing them by a doctor's viewing terminal.

There is a wide range of such medical devices, starting from simpler devices comprising one-sensor, such as thermometers for body temperature measurements, oximeters for blood oxygen level measurements, blood pressure meters and continuing with more complex devices, such as electrocardiograph in the form of traditional Holter monitor or event recorder for spot measuring electrocardiogram ECG, electronic stethoscope for lung and heart medical examination auscultation.

In the case of some chronic diseases, like cardiovascular diseases or respiratory diseases, different devices are used to monitor each phase of disease. In the early disease stages some specific devices are used, in the chronic stage other devices are used, whereas for the monitoring of the rehabilitation stage where appropriate, yet other devices are used.

Disadvantages of Prior Art

First group of disadvantages: limited correlation capability between the measurements of various sensors.

Due to complexity of medical services, a wide range of different devices is required for monitoring health parameters.

Some of the measurements are directly related to the cause of patient's disease. Taking as example patients with cardiovascular diseases, electrocardiography ECG or blood pressure are very important measurements, but in the same time, other health parameters are of use, like respiration rate, blood saturation, temperature, motion index, lung or heart auscultation etc., because their respective measurements can provide the doctor with supplementary hemodynamic data about the progress and acuity of the respective disease, or particulars of the chronical stage of the disease.

Today, for non-critical patients, many of the above-mentioned health parameters are measured with many different devices, usually one device at a time for example: body thermometer, oximeter for blood saturation, blood pressure monitor cuff, stethoscope for lung and heart examination, electrocardiograph ECG for electrical heart activity measurements, phonocardiograph PCG for heart synchronous electrical and mechanical activity examination, a camera for skin, throat or ear examination etc. In case of long-term patient monitoring, repetitive measurements are performed using the same devices used for spot measurements by measuring the same health parameters like temperature, heart rate, blood pressure, blood oxygenation more frequently, for example 2-7 times per day each time using sequentially one different device for each health parameter after the other which require separate time for each device to carry out the respective measurements.

Using all of these devices in a telemedicine environment at patient's home by the patient himself brings into play the problem of limited correlation capability between the measurements of various sensors because:

- each device has its specific capabilities to carry out measurements and to process them,
- each device has its specific capabilities and requirements for connection configuration, acquiring data and sending data,
- many devices require cumbersome configuration setup for each of them like wireless paring, connecting, disconnecting, charging battery for each of them which leads to waste of doctor or patient time and reduce patient adherence to treatment,
- it's very difficult if not impossible to fusion synchronized data from more than one device, because, typically each device has its specific capabilities and requirements for storing and transmitting the measurements which, in many cases are multi-vendor, with different ownership of the storage, either on device or on cloud facilities and custom private communication protocols among other factors,
- it's very difficult to ensure full separation of the measurements from different patients, the processing, the storage as well as the transmission to patient account data to the health specialist if the same devices are used by more than one patient without some authentication level.

Second group of disadvantages: using various sensors makes the medical device a bulky assembly, in some cases may rise conflicting technical requirements.

Each sensor has its own specific technical requirements in order to function properly. The technical requirements include specific adaptations of the sensors to be placed to the best anatomic part for each sensor where the device comprising the sensor must be placed on patient's body. Said best anatomic part usually differs when it comes to measuring different health parameters. For example, for the electrocardiograph ECG, the best anatomic part to place the respective sensor is on patient's chest near the heart, because the electrical signal acquired from the heart is stronger; for blood saturation places, finger thumbs or ear-lobs are the best anatomic parts due to high vascularization area; for temperature, the forehead or underarm can be good place to measure; for lung or heart auscultation the best anatomic part of the sensor is in proximity contact with those organs on chest are required.

The mere putting all together of known medical devices as they are today in one box will inherit pre-existing disadvantages and may rise conflicting technical requirements. In their turn, the conflicting technical requirements may lead to bulky, user-unfriendly, and cumbersome device when attempting to resolve them.

An example of conflicting technical requirements occurs if one wishes to combine an electrocardiograph ECG with a photoplethysmogram PPG. For example, for the daily spot measurements, it is much easier to measure blood saturation or ECG from the fingers of the patient by placing the finger thumb on electrode pads or on the photoplethysmogram PPG optical area, in order to free-up hands and allow daily activities, but this approach is not suitable for the respective measurements over a continuous longer period of time for high-risk patients. For continuous monitoring, the chest, the wrist or the arm are preferred locations allowing the sensors to be in permanent contact with the patient's skin through a patch with skin adhesive, wrist band, chest belt or arm band. The finger is a good place for the photoplethysmogram PPG sensor, but the measurements acquired from the finger are not so accurate for electrocardiograph ECG because of the longer distance between the finger and the heart, which leads to acquiring weak electrocardiograph ECG signal. In the case of the chest, if using a patch electrode device a good location for electrocardiograph ECG is near heart but is very challenging for photoplethysmogram PPG measurements because of much less vascularization and more deeper and thinner blood vessels in this area.

Problem to be Solved by the Invention

There is a need for an improved multi-role medical device, easy to use at home, preferable all-in one with no or little maintenance capable to cover common episodic primary care events, perform clinical remote examination up to more complex chronical diseases needs like the cardiovascular diseases CVD or respiratory diseases.

There is also a need that the improved multi-role medical device enables the monitoring of the health parameters in integrated longitudinal approach in respect to various stages of the disease from prevention, diagnostic, living with chronic disease, acute phase and post-acute episode rehabilitation, covering the situations when the monitoring takes place either at the doctor's office, or at patient's home carried out by the patient, or at patient's home carried out by the health specialist using clinical remote examination techniques and devices.

Finally, there is also a need that the improved multi-role medical device enables the monitoring of the health parameters for the sports, fitness and wellness patient workouts activities.

The technical problem to be solved to address all the afore-mentioned needs is to find a medical device for monitoring health parameters capable of connecting and controlling a wide range of single or multi-functional sensors to address different monitoring needs in respect to the place of monitoring and in respect to the objective of the monitoring, without being too complex or cumbersome when being used, while overcoming possible incompatibilities between the technical requirements of various sensors included in the medical device. The medical device of the invention must address the needs to monitor the health parameters either by the health specialist in the health facilities, or by the patient at patient's home carried out, or by the health specialist at patient's home carried out using clinical remote examination. The medical device of the invention must address the needs to monitor the health parameters for the purpose of prevention, diagnostic, acute phase, living with chronic disease, rehabilitation, sports, fitness and wellness activities.

SUMMARY OF THE INVENTION

In order to overcome the disadvantages of prior art, in a first aspect of the invention it is presented a medical device for monitoring health parameters of a patient comprising a main unit electrically and mechanically connectable to a sensor module.

When the sensor module is electrically and mechanically connected to the main unit, the medical device is configured to acquire one or more bio-signals of the patient corresponding to an anatomic part of the patient, and the medical device is configured to carry out measurements of health parameters by means of configurations of the main unit and, respectively of the sensor module.

The main unit comprises:
main unit mechanical means configured for detachable mechanical connection to a sensor module mechanical means of the sensor module,
  wherein the shape of the sensor module is configured to accommodate partially the main unit within a sensor module cavity of a sensor module receptacle of the sensor module, and
  wherein the sensor module mechanical means comprises:
    a guiding recess corresponding to a guiding element of the main unit for guiding the mechanical connection of the main unit within said sensor module cavity,
    two or more sensor module detent recesses, each sensor module detent recess corresponding to a spring-loaded detent of a spring-loaded detent mechanism,
a main unit array interface configured for electrical connection to a sensor module array interface of the sensor module, the main unit array interface comprising:
  main unit fixed-function electrical contacts,
  main unit multi-function electrical contacts,
  one or more programmable multiplexer switches,
  one or more simple switches,
a processors' sub-unit, the processors' sub-unit comprising:
  a main processor, the main processor comprising communication drivers,
  a memory,
  main unit sensors' components,
  enabling components, the enabling components comprising at least:
    a lock-in detection interface,
    an identification interface.

The sensor module comprises:
sensors' components, the sensors' components configured to carry out sensor module tasks, the sensor module array interface arranged within the sensor module cavity, the sensor module array interface comprising:
  sensor module fixed-function electrical contacts, or
  sensor module multi-function contacts, or
  sensor module fixed-function electrical contacts and sensor module multi-function contacts,
sensor module enabling components, the sensor module enabling components comprising at least:
  a sensor module lock-in detection interface, the sensor module lock-in detection interface configured to mate the lock-in detection interface of the main unit,
  a sensor module identification interface, the sensor module identification interface configured to mate the identification interface of the main unit,
[1] wherein
the main unit fixed-function electrical contacts are configured to be connected to the sensor module fixed-function electrical contacts when the sensor module is mechanically connected to the main unit, and
the main unit multi-function electrical contacts are configured to be selectively connected to one of the three selected from the below list when the sensor module is mechanically connected to the main unit:
  to the sensor module multi-function contacts, or
  to the sensor module fixed-function electrical contacts, or
  to the sensor module multi-function contacts and the sensor module fixed-function electrical contacts,
[2] and wherein
the one or more simple switches are configured for connecting the main unit sensors' components and the enabling components to the main unit fixed-function electrical contacts, and the one or more programmable multiplexer switches are configured for selectively connecting the communication drivers and the enabling components to the main unit multi-function electrical contacts,
[3] and wherein
the lock-in detection interface is configured together with the sensor module lock-in detection interface to detect when the electrical and mechanical connection of the sensor module to the main unit is established, the identification interface is configured together with the sensor module identification interface to recognize the sensor module connected to the main unit and the associated sensor module tasks of said connected sensor module,
[4] and wherein
the processors' sub-unit is configured to comprise predetermined processors' instructions stored in the memory for the following:
  instructions for detection of the sensor module when the sensor module is electrically and mechanically connected to the main unit,
  instructions for the recognition of the associated sensor module tasks,
  instructions for selection of one or more specific sensor module tasks,
  instructions for loading configuration for sensor module, corresponding to one or more specific sensor module tasks
  instructions for connecting, by means of the one or more simple switches, the main unit sensors' components and the enabling components to the sensor module fixed-function electrical contacts, for the one or more selected specific sensor module tasks, according to the configuration,
  instructions for selectively connecting, by means of the one or more programmable multiplexer switches, the communication drivers and the enabling components to the sensor module multi-function contacts or to the sensor module fixed-function electrical contacts, or to the sensor module multi-function contacts and the sensor module fixed-function electrical contacts, for the one or more selected specific sensor module tasks, according to the configuration
  instructions for processing the measurements,
  instructions for storage of the processed measurements in the memory as a patient data file, and instructions for making available the measurements of health parameters to one or more external devices in order to be used for monitoring the health parameters of the patient,
  instructions for electrically disconnecting of the main unit from the sensor module.

In a second aspect of the invention it is presented a computer-implemented method of monitoring health parameters of a patient using the medical device configured to carry out measurements of health parameters according to any of the claims 1 to 14, the method comprising the following steps:

S1 electrically and mechanically connecting of the main unit of the medical device to a selected sensor module of the medical device, S2 detecting the electrical and mechanical connection between the main unit and the sensor module by the lock-in detection interface together with the sensor module lock-in detection interface, S3 recognizing the associated sensor module tasks of the sensor module by the identification interface together with the sensor module identification interface, S4 selecting by the processors' sub-unit one or more specific sensor module tasks from the sensor module tasks S5 loading configuration for the sensor module by the processors' sub-unit corresponding to the one or more specific sensor module tasks, S6 Simultaneously, at the instructions received from the processors' sub-unit, for the one or more selected specific sensor module tasks:

electrically connecting the main unit sensors' components and the enabling components to the sensor module fixed-function electrical contacts, according to the configuration, electrically connecting the communication drivers to the sensor module multi-function contacts or to the sensor module fixed-function electrical contacts, or to the sensor module multi-function contacts and to the sensor module fixed-function electrical contacts, according to the configuration, S7 acquiring by the medical device of the one or more bio-signals from an anatomic part of the patient, S8 processing the one or more bio-signals and outputting the measurements of health parameters by the main processor of the processors' sub-unit, S9 storing the measurements of health parameters in a memory as a patient data file to be used for monitoring health parameters of the patient, and making available by the processors' sub-unit of the measurements of health parameters to one or more external devices in order to be used for monitoring the health parameters of the patient, S10 electrically and mechanically disconnecting of the main unit from the sensor module.

In a third aspect of the invention it is presented a non-transitory computer-readable storage medium encoded with a computer program, the computer program comprising instructions executable by the medical device for monitoring health parameters of a patient of any preferred embodiment, which, upon such execution by the medical device, causes the medical device to perform operations of the method for monitoring health parameters of the patient of any preferred embodiment.

Any feature in one aspect of the invention may be applied to other aspects of the invention, in any appropriate combination. In particular, method features may be applied to device features, and vice versa.

Wherever applicable, means—plus—function features may be expressed alternatively in terms of their corresponding structure.

Particular combinations of the various features of the invention can be implemented and/or supplied and/or used independently.

Advantages

The medical device of the invention has the following advantages:

the medical device is very versatile allowing the connection and control of a plurality of sensors because it has various sensor modules that can be connected to the main unit, the patient or the health specialist selecting among them the sensors module best fit to make the measurements of the required health parameters, including connecting successively various sensor modules and storing all the measurements made by each of them, the problems of the conflicting technical requirements are solved by the centralized control of various sensors, fusion computing advantages are obtained by carrying out the synchronized tasks of the final processing operations ending with the measurements in a single place of the main unit, the medical device is neither bulky nor heavy because it uses the same connection and processing capability of the main unit with each sensor module and because of the optimized design of both the main unit and each sensor module as a unitary device, the medical device allows a unitary storage of all measurements of the health parameters for a longer period of time marking exactly timestamp when each measurement was done and corresponding to which sensor module, benefiting of storing all the health parameters into the same memory.

the medical device allows optimization of the processing power by using the main processor of the main unit as a centralized main processor, which in its turn leads to the optimization of the monitorization on long-term basis and also leads to the possibility of miniaturizing the sensor module, because the processing needs of the sensor module is dynamically adjusted for each sensor module task.

LIST OF DRAWINGS

Further special features and advantages of the present invention can be taken from the following description of an advantageous embodiment by way of the accompanying drawings.

Example of Realization of the Main Unit

Figure 5:
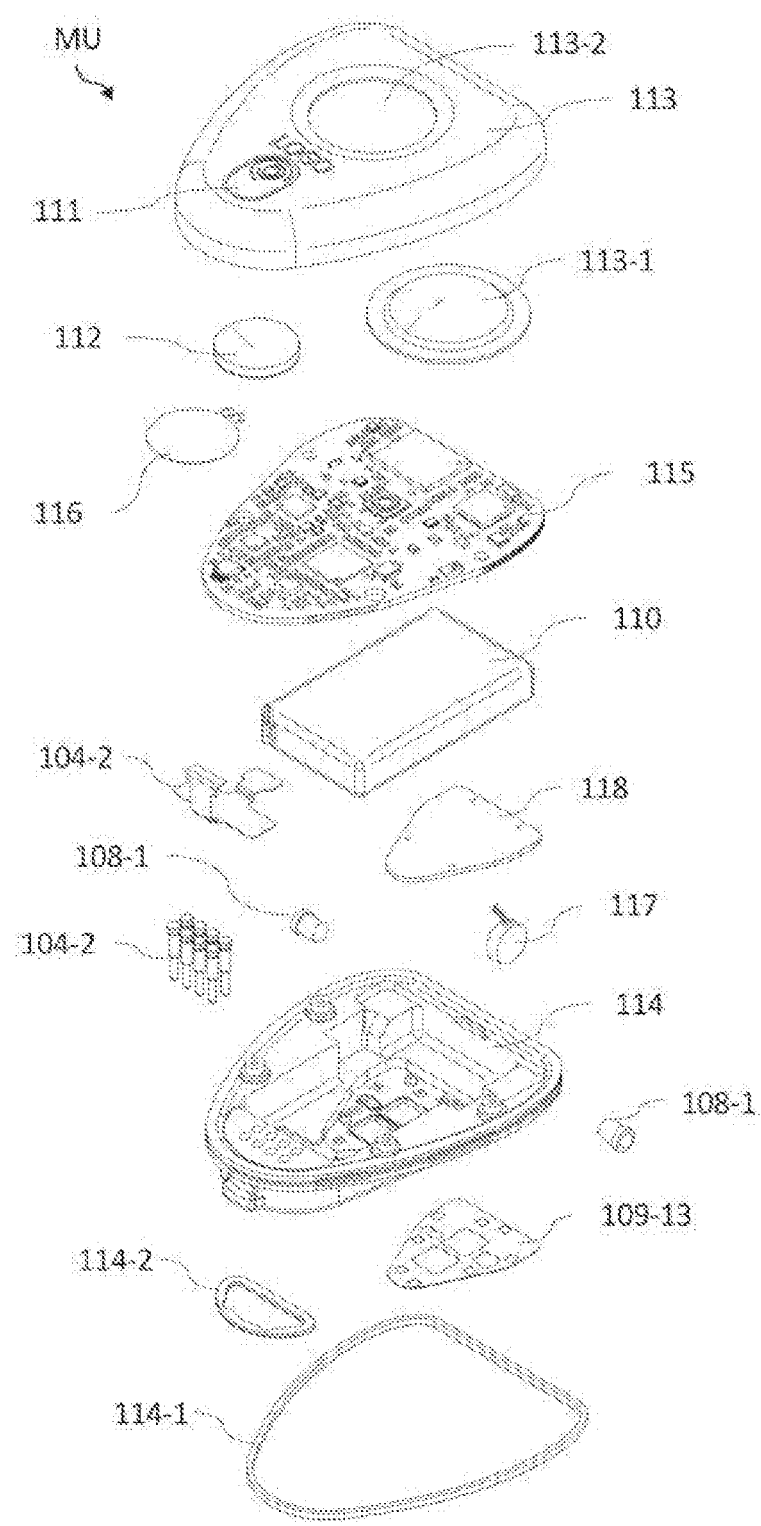

FIG. 5 illustrates an exploded view of the main unit of an example of realization.

Figure 6A:
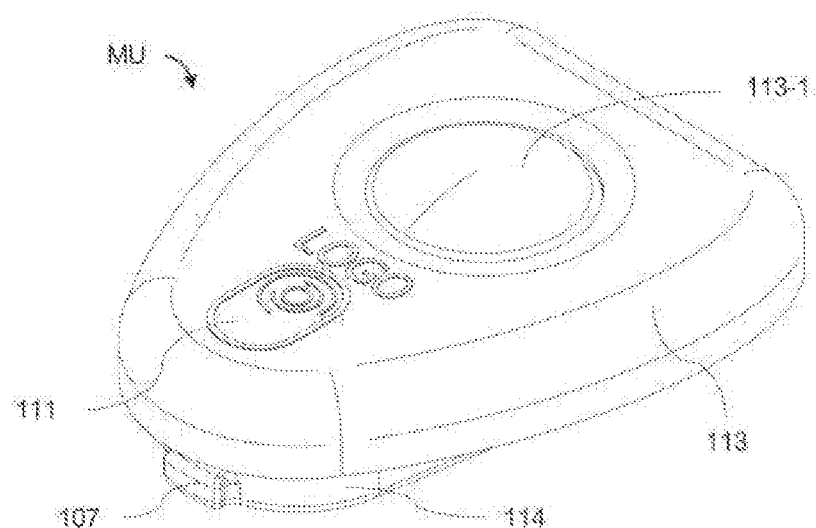

FIG. 6A illustrates a view from the exterior of the main unit.

Figure 6B:
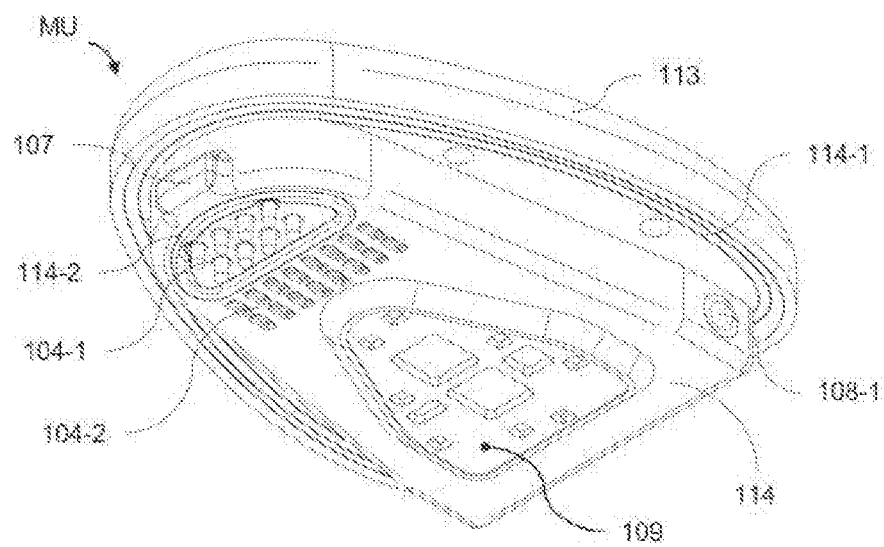

FIG. 6B illustrates a view of the main unit from the side of the mechanical and electrical connection.

Figure 7A:
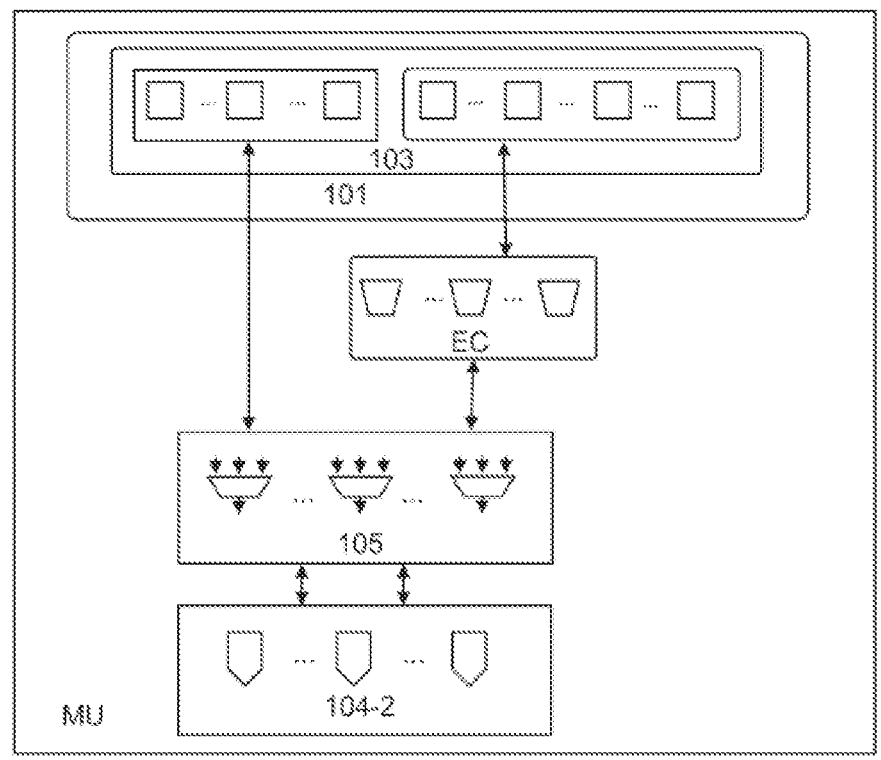

FIG. 7A illustrates schematically the connection of the communication drivers with the one or more programmable multiplexer switches.

Figure 7B:
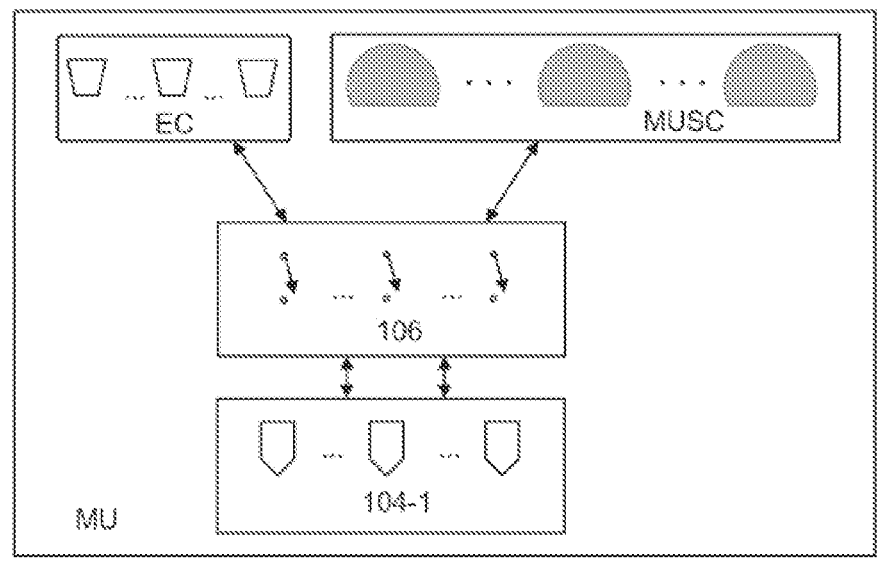

FIG. 7B illustrates schematically the connection of the sensors' components enabling components with the one or more simple switches.

Figure 7C:
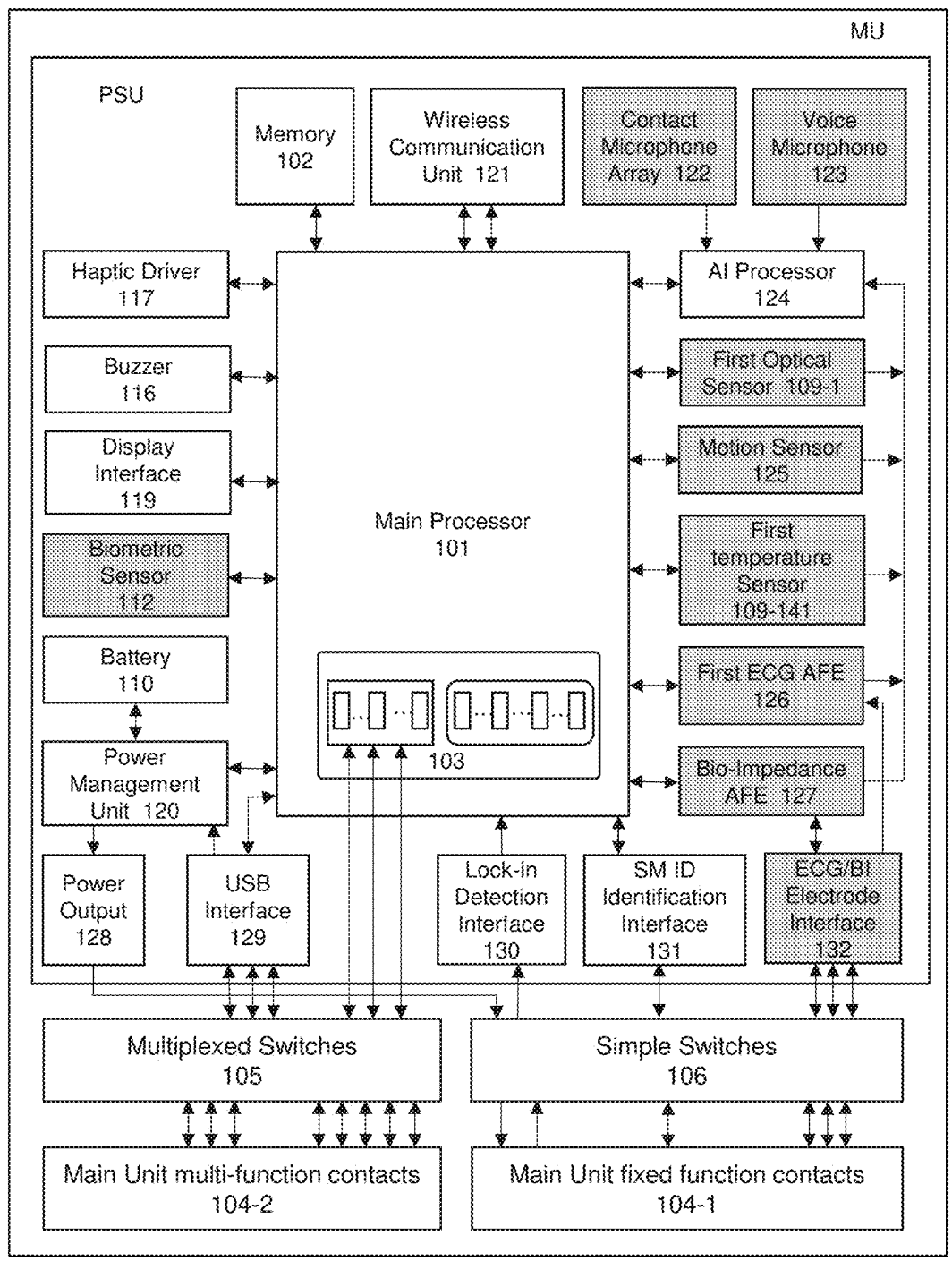

FIG. 7C illustrates the diagram of the electronic components of the main unit.

Examples of Positioning of the Medical Devices

Figure 8A:
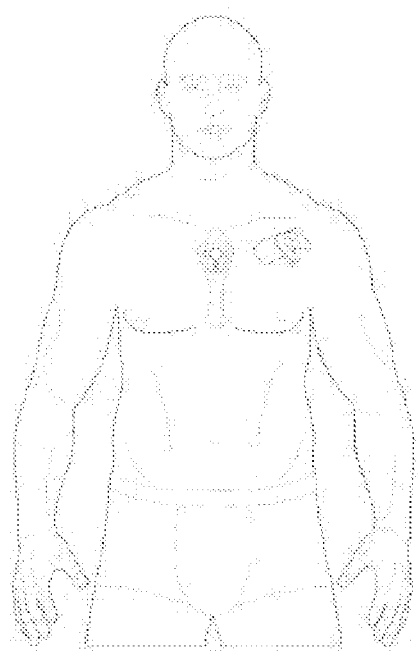

FIG. 8A illustrates non-limiting examples of positioning the medical device corresponding to the sensor module of the first sensor module preferred embodiment.

Figure 8B:
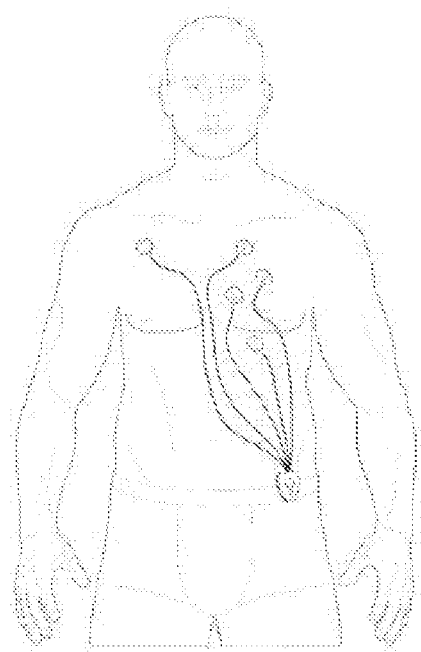

FIG. 8B illustrates non-limiting examples of positioning the medical device corresponding to the fourth first preferred embodiment of the sensor module.

Figure 8C:
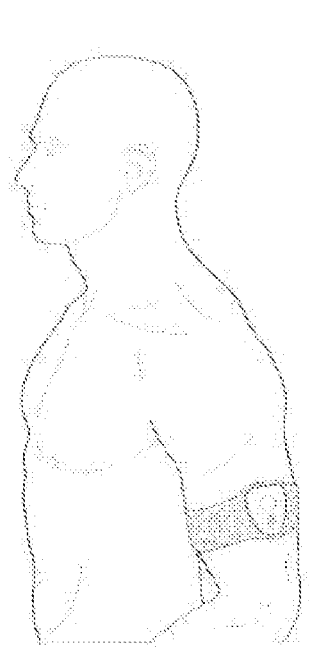

FIG. 8C illustrates non-limiting examples of positioning the medical device corresponding to the seventh preferred embodiment of the sensor module.

Figure 8D:
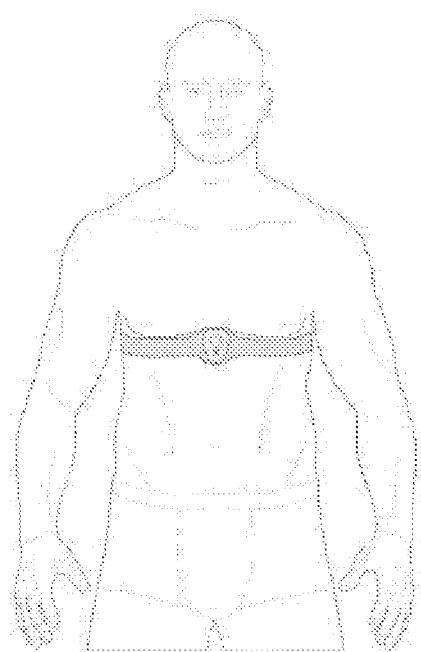

FIG. 8D illustrates non-limiting examples of positioning the medical device corresponding to the fifth preferred embodiment of the sensor module.

First Sensor Module Preferred Embodiment SM1

Figure 9A:
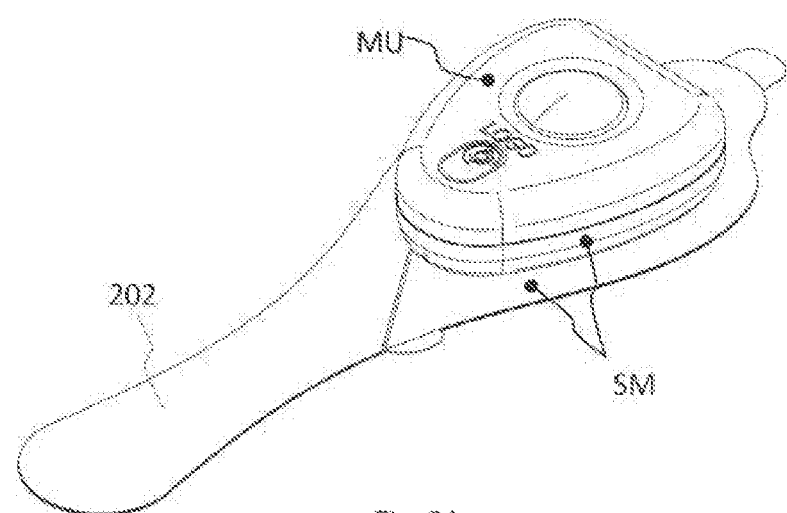

FIG. 9A illustrates the main unit connected to the sensor module.

Figure 9B:
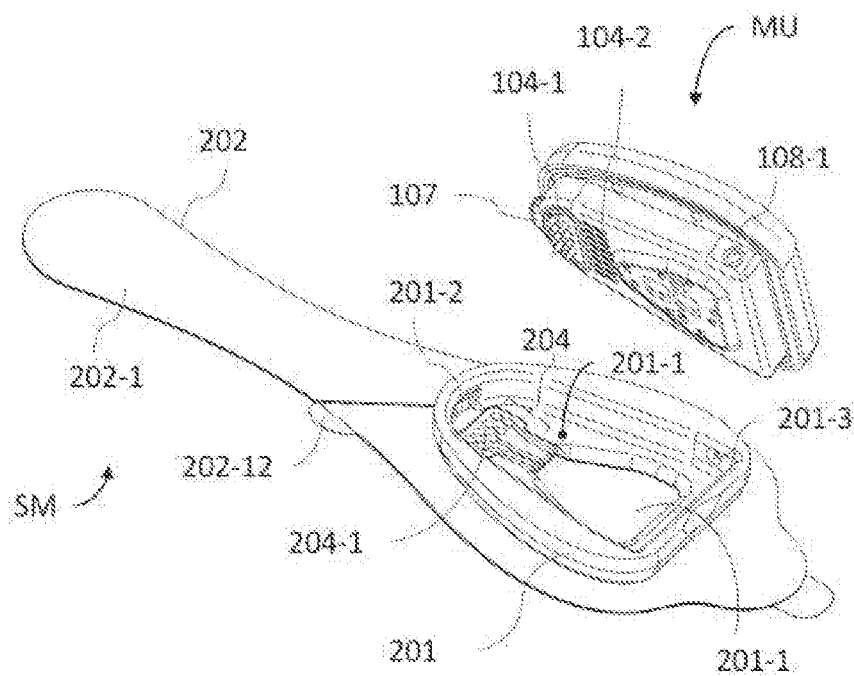

FIG. 9B illustrates a view depicting the main unit disconnected to the sensor module, illustrating the main unit array interface and the sensor module array interface.

Figure 9C:
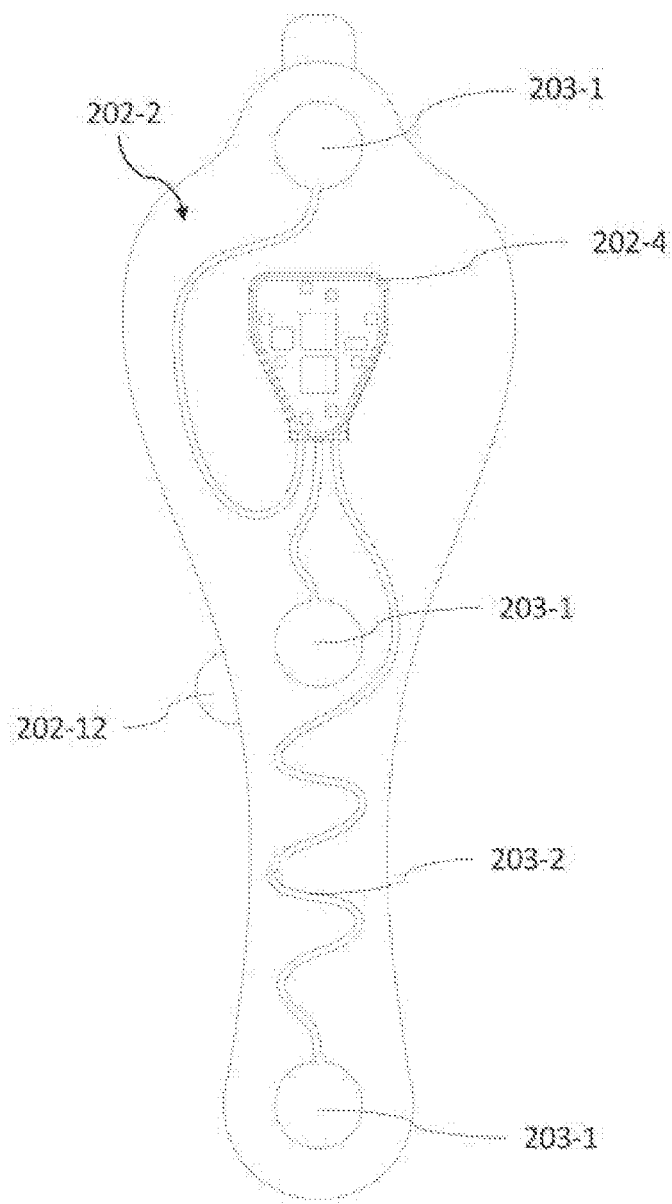

FIG. 9C illustrates a view from of the flexible foil second side.

Figure 9D:
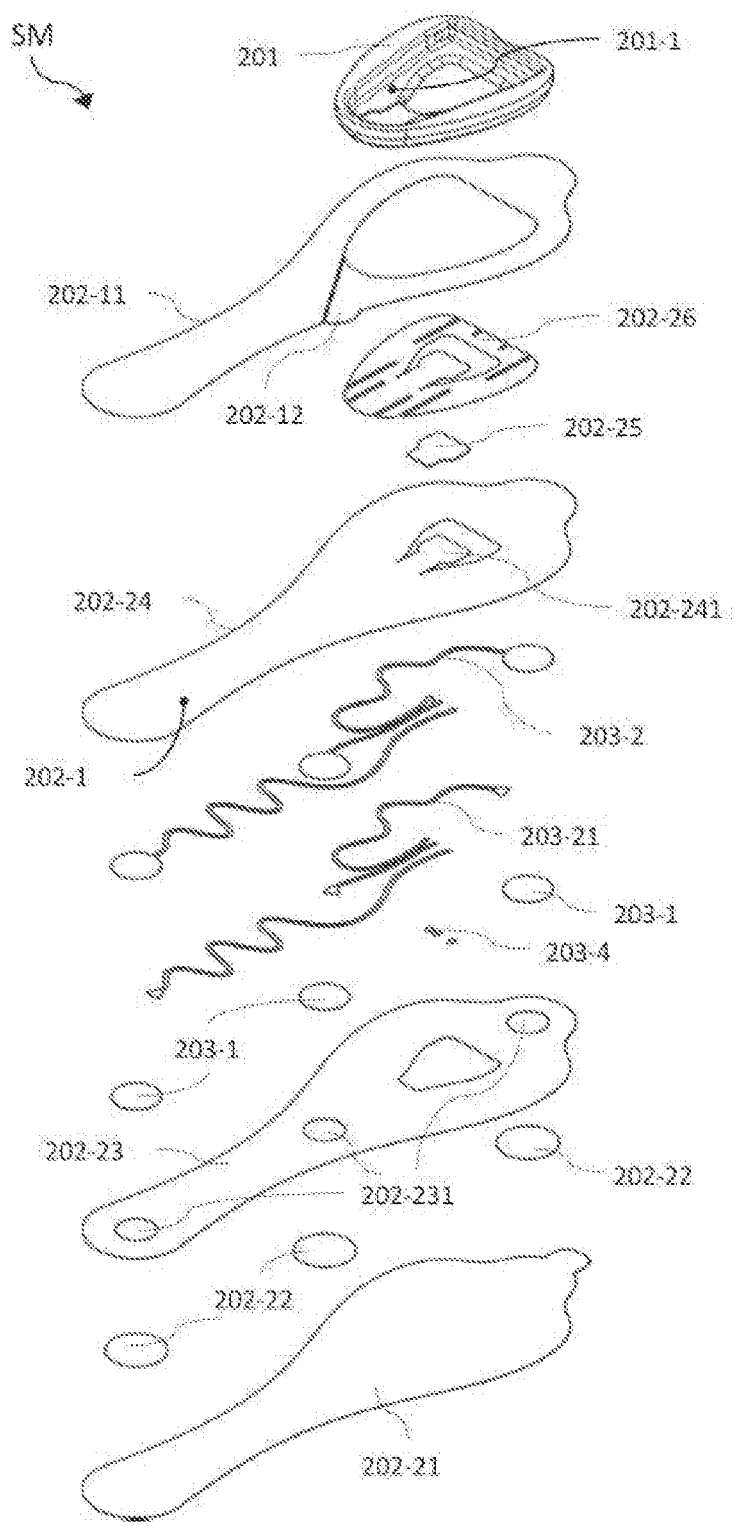

FIG. 9D illustrates an exploded view of the components of the flexible foil.

Figure 9E:
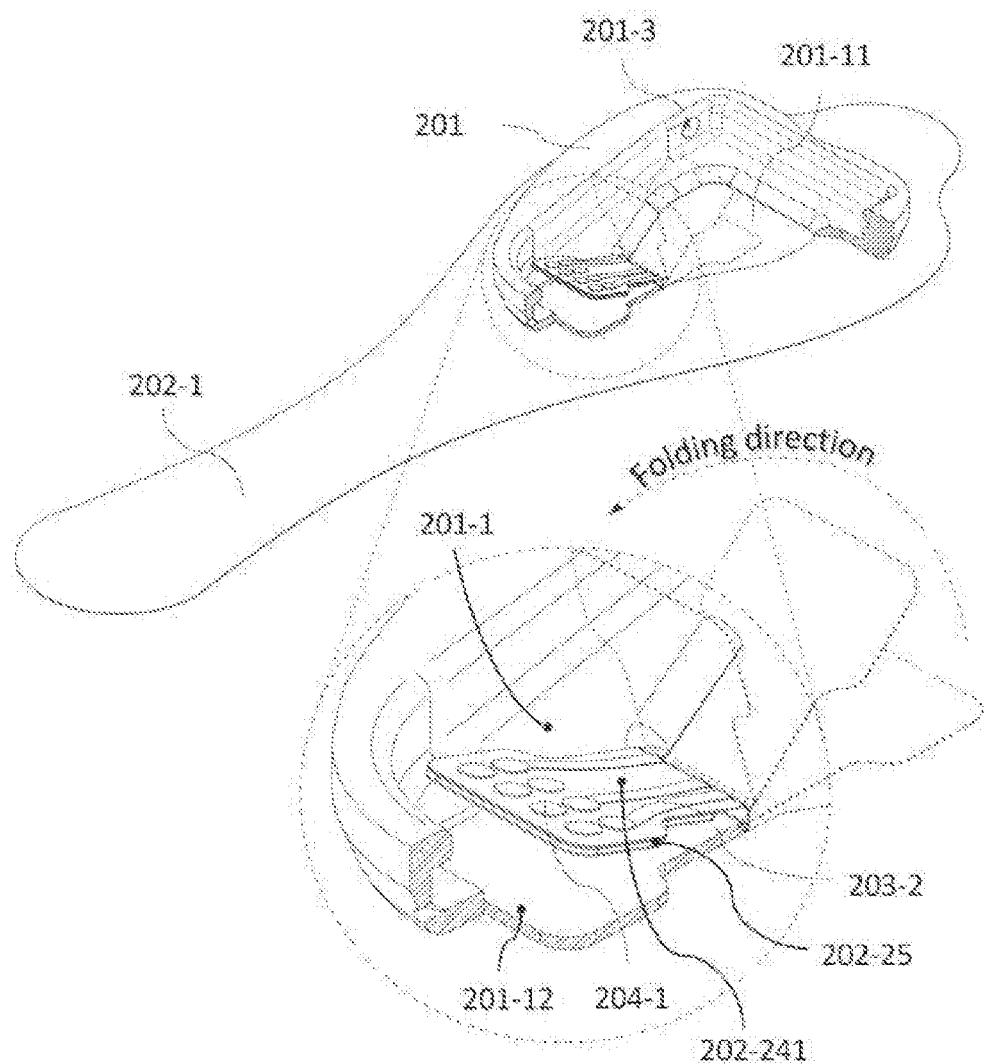

FIG. 9E illustrate a first alternative example of realization.

Figure 9F:
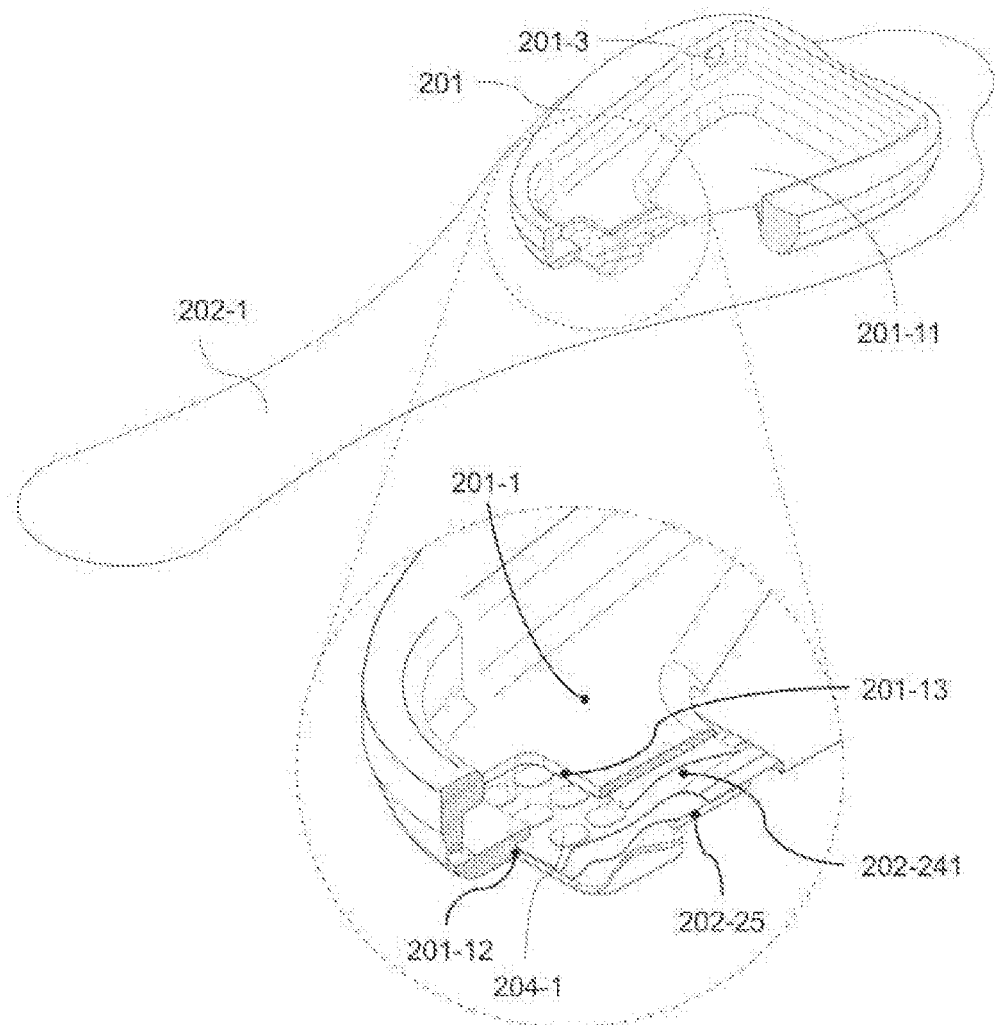

FIG. 9F illustrates a second alternative example of realization.

Figure 9G:
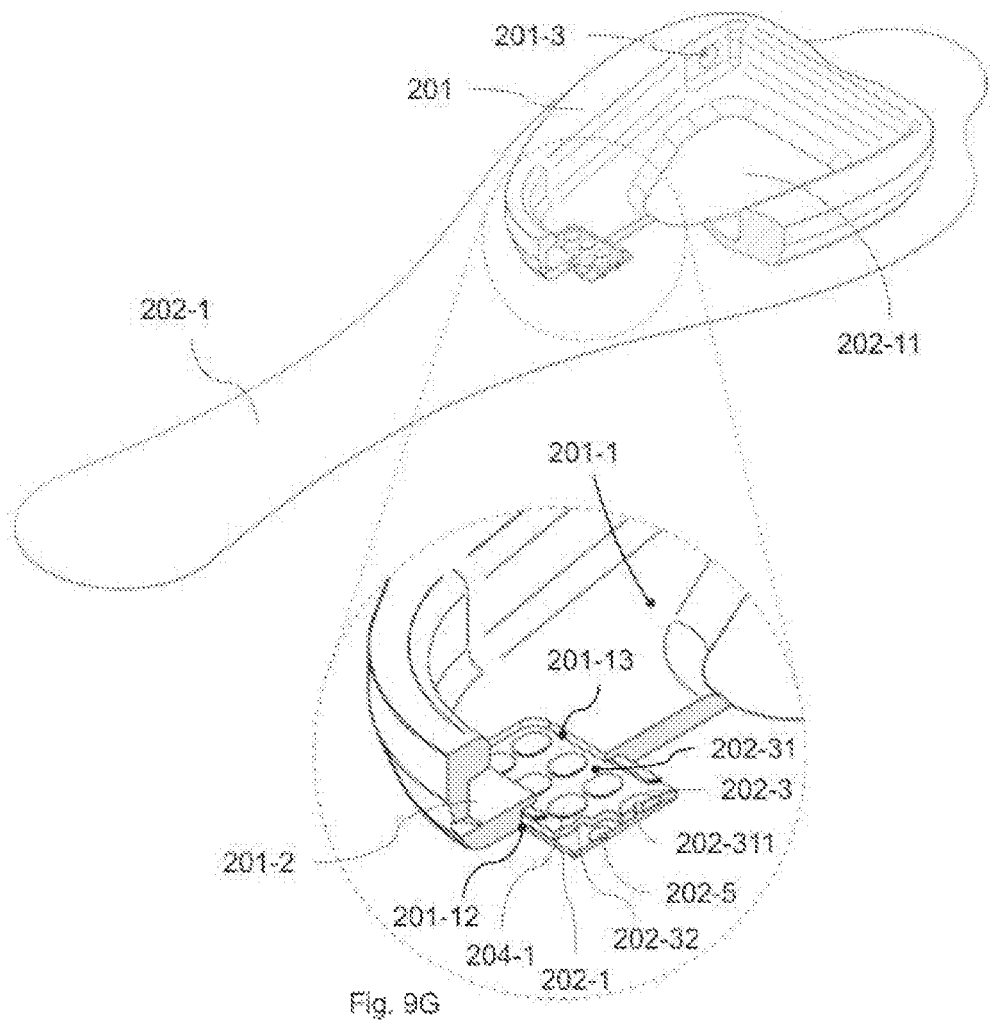

FIG. 9G illustrates a third alternative example of realization.

Figure 9H:
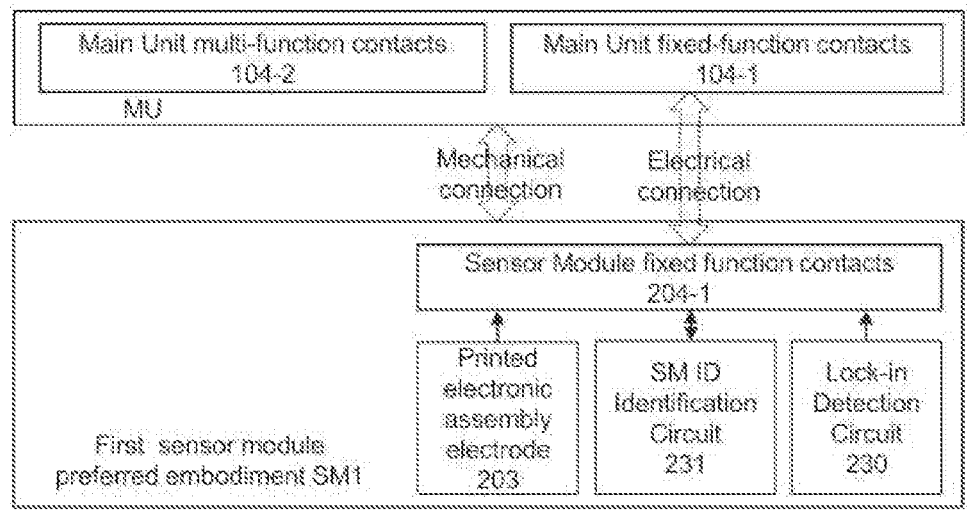

FIG. 9H illustrates the diagram of the electronic components of the sensor module.

Second Sensor Module Preferred Embodiment SM2

Figure 10A:
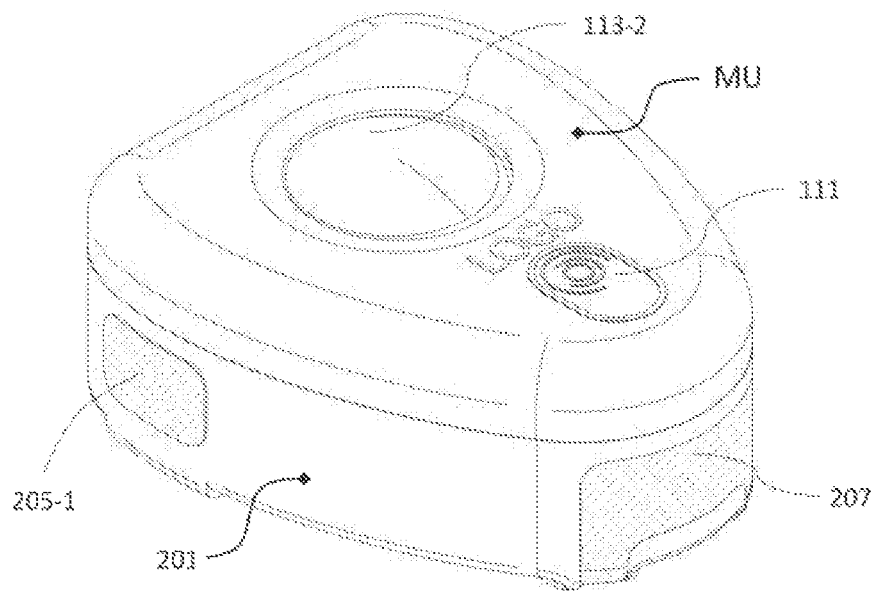

FIG. 10A illustrates the main unit connected to the sensor module—lateral view.

Figure 10B:
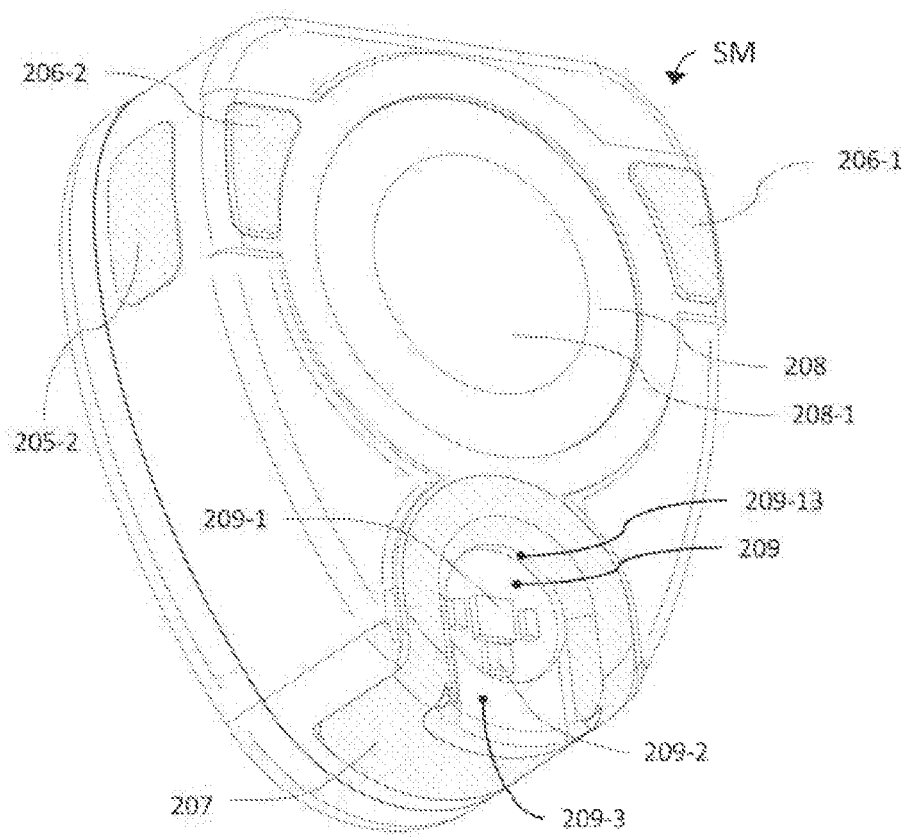

FIG. 10B illustrates the main unit connected to the sensor module—bottom view from the contact point with patient's skin.

Figure 10C:
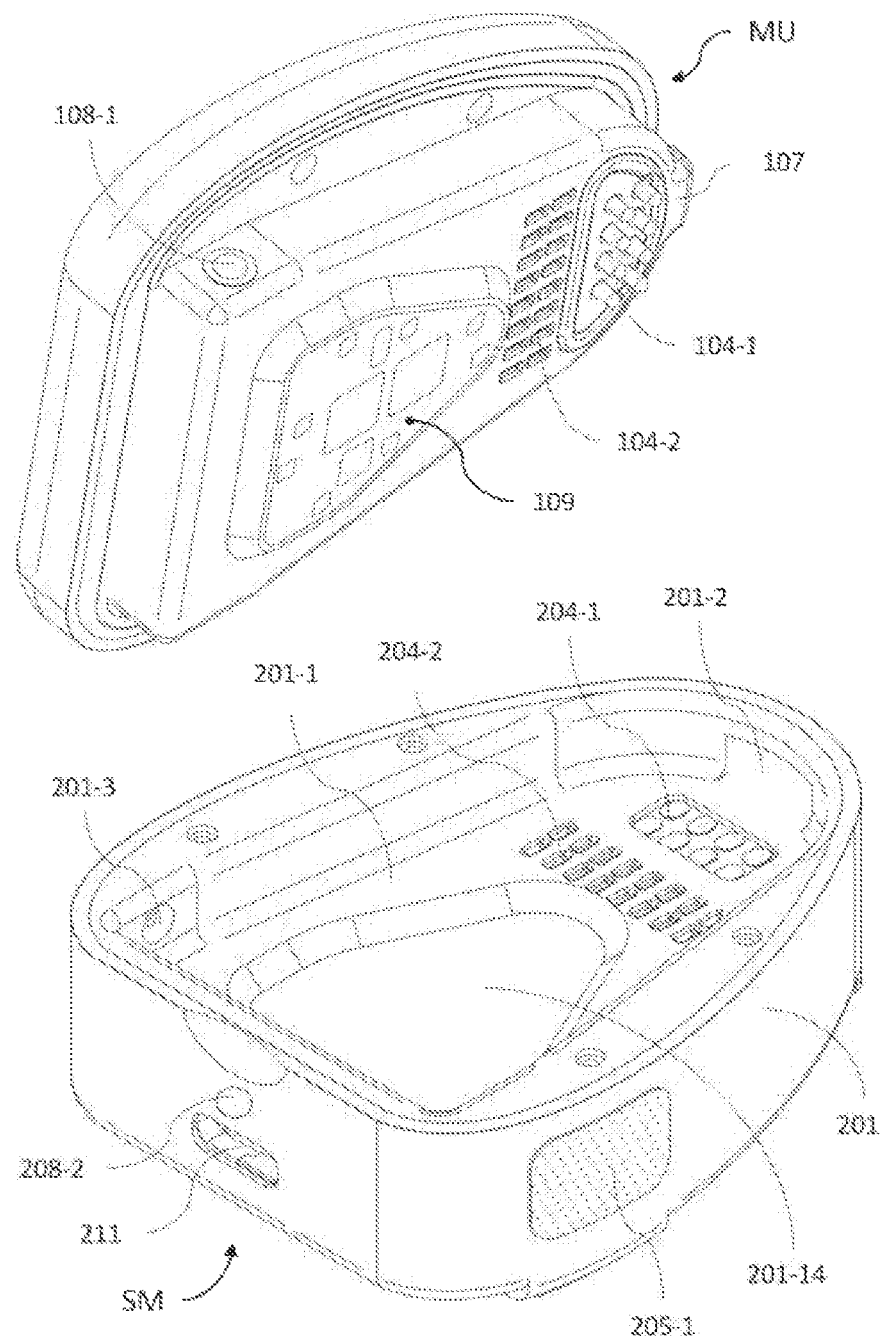

FIG. 10C illustrates a view depicting the main unit disconnected to the sensor module, illustrating the main unit array interface and the sensor module array interface.

Figure 10D:

FIG. 10D illustrates the modality of placing the sensor module in contact with skin of the patient when the one or more forehead temperature sensors is activated.

Figure 10E:
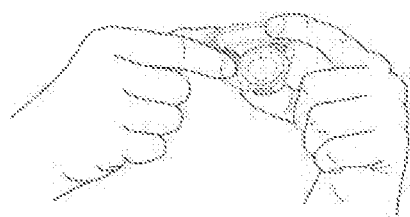

FIG. 10E illustrates the modality of placing the sensor module in contact with skin of the patient when the first loop is activated.

Figure 10F:
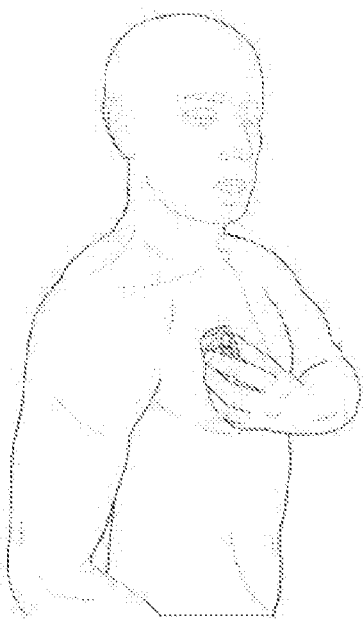

FIG. 10F illustrates the modality of placing the sensor module in contact with skin of the patient when the second loop and/or the stethoscope are activated.

Figure 10G:
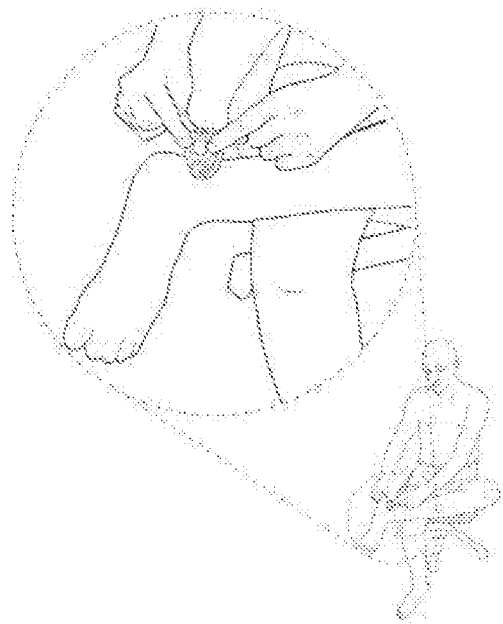

FIG. 10G illustrates the modality of placing the sensor module in contact with skin of the patient when the electrocardiogram is carried out accordingly to Einthoven's triangle method, when the third loop is activated.

Figure 10H:
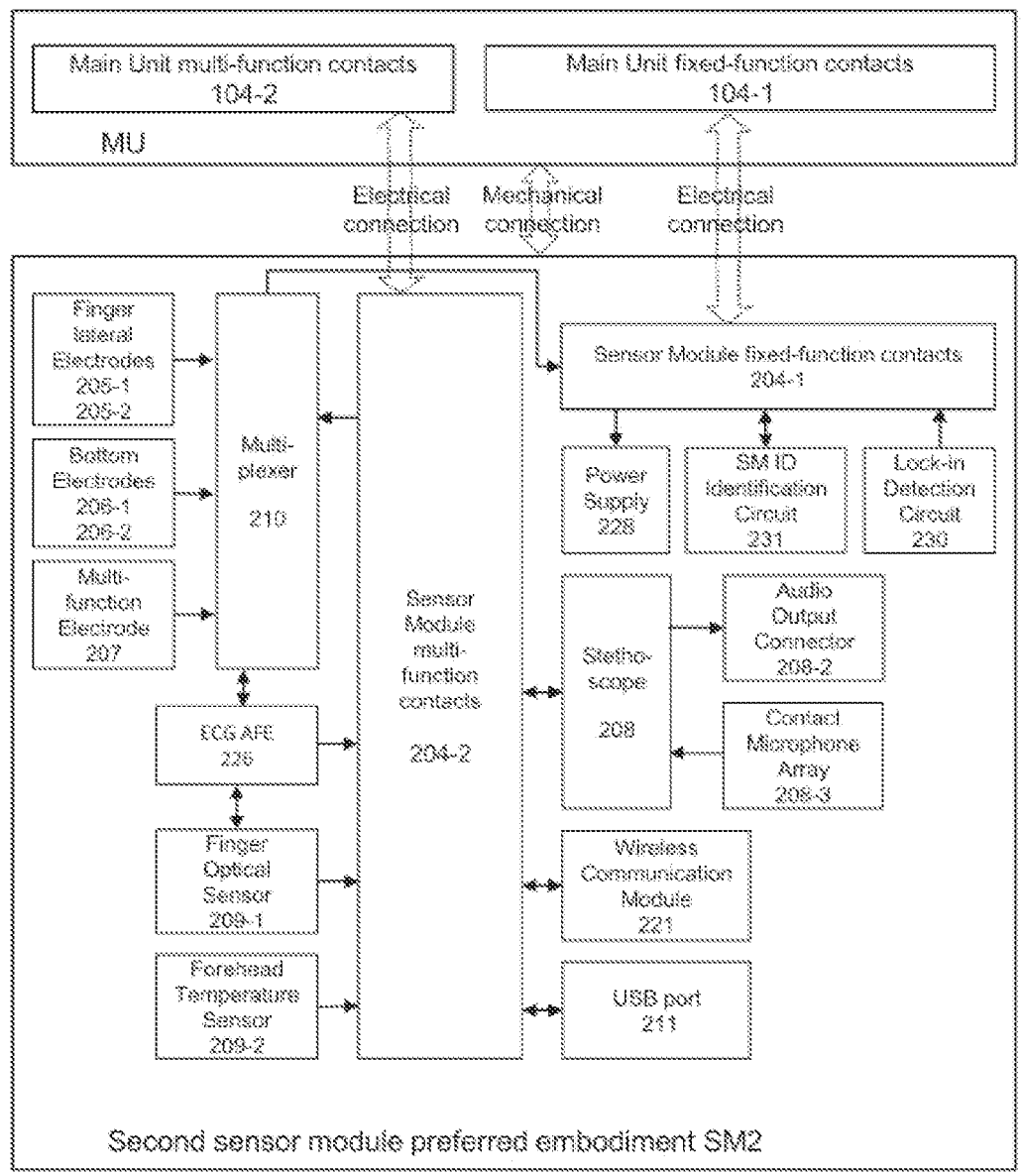

FIG. 10H illustrates the diagram of the electronic components of the sensor module.

Third Sensor Module Preferred Embodiment SM3

Figure 11A:
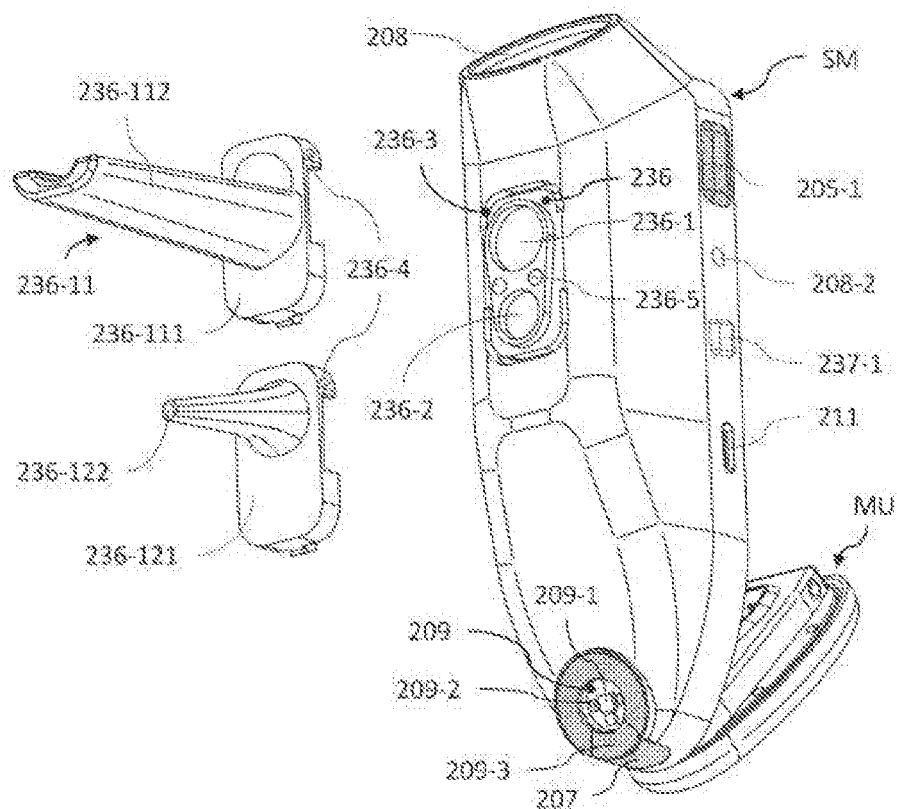

FIG. 11A illustrates the main unit connected to the sensor module—perspective view from video camera area side.

Figure 11B:
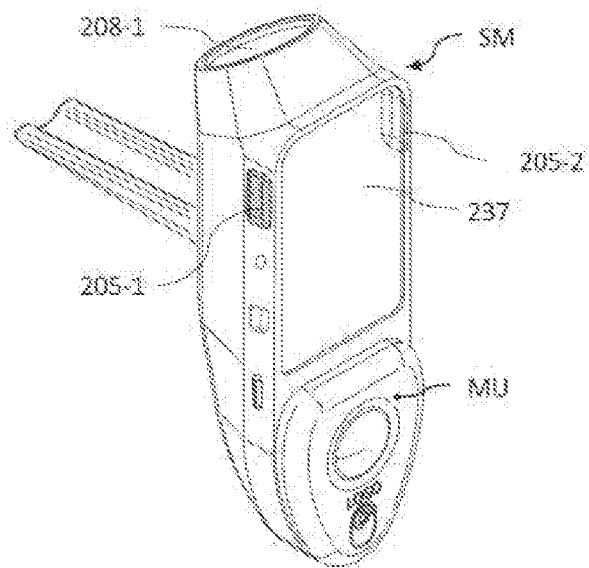

FIG. 11B illustrates the main unit connected to the sensor module—perspective view from the main unit side.

Figure 11C:
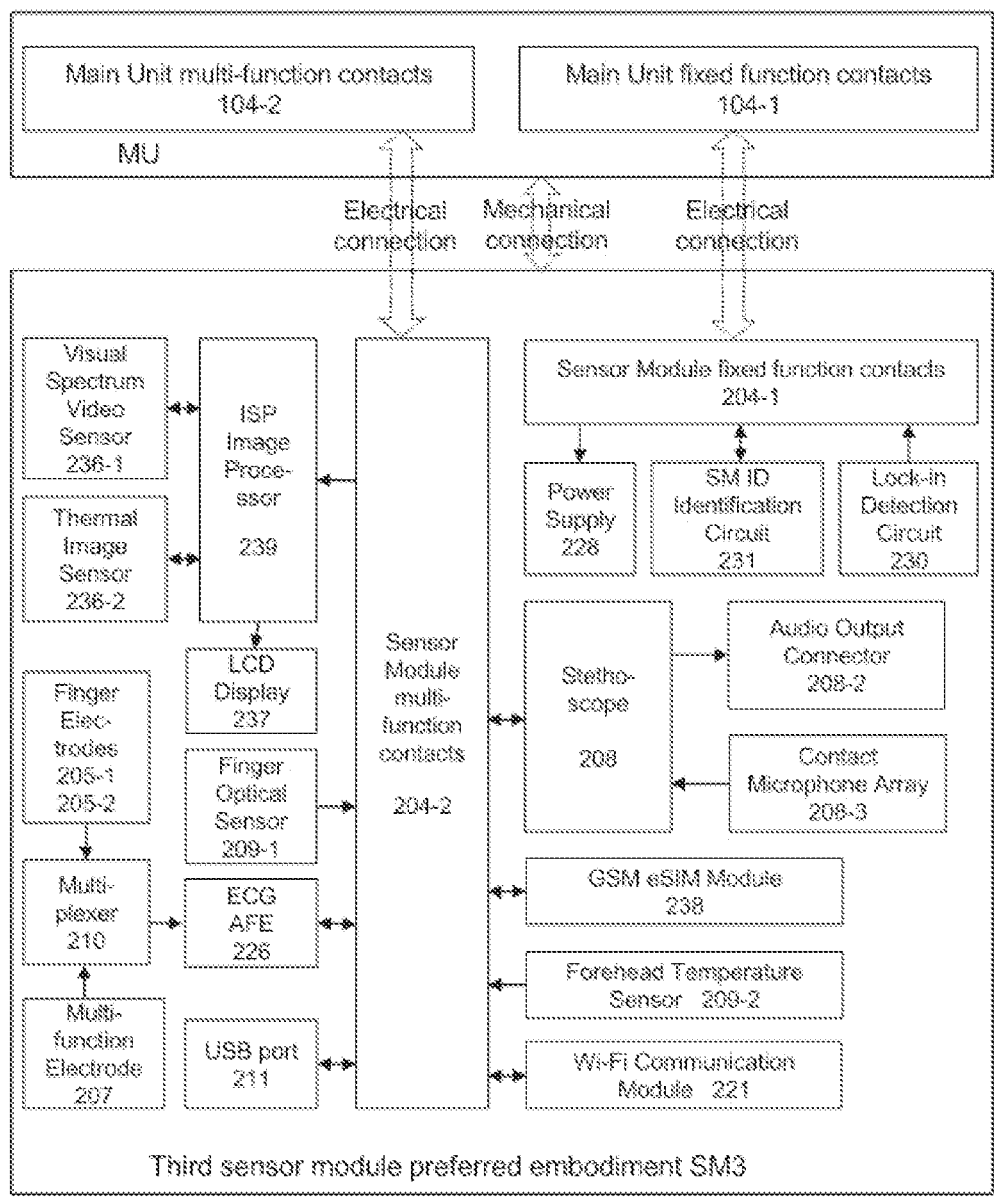

FIG. 11C illustrates the diagram of the electronic components of the sensor module.

Fourth Sensor Module Preferred Embodiment SM4

Figure 12A:
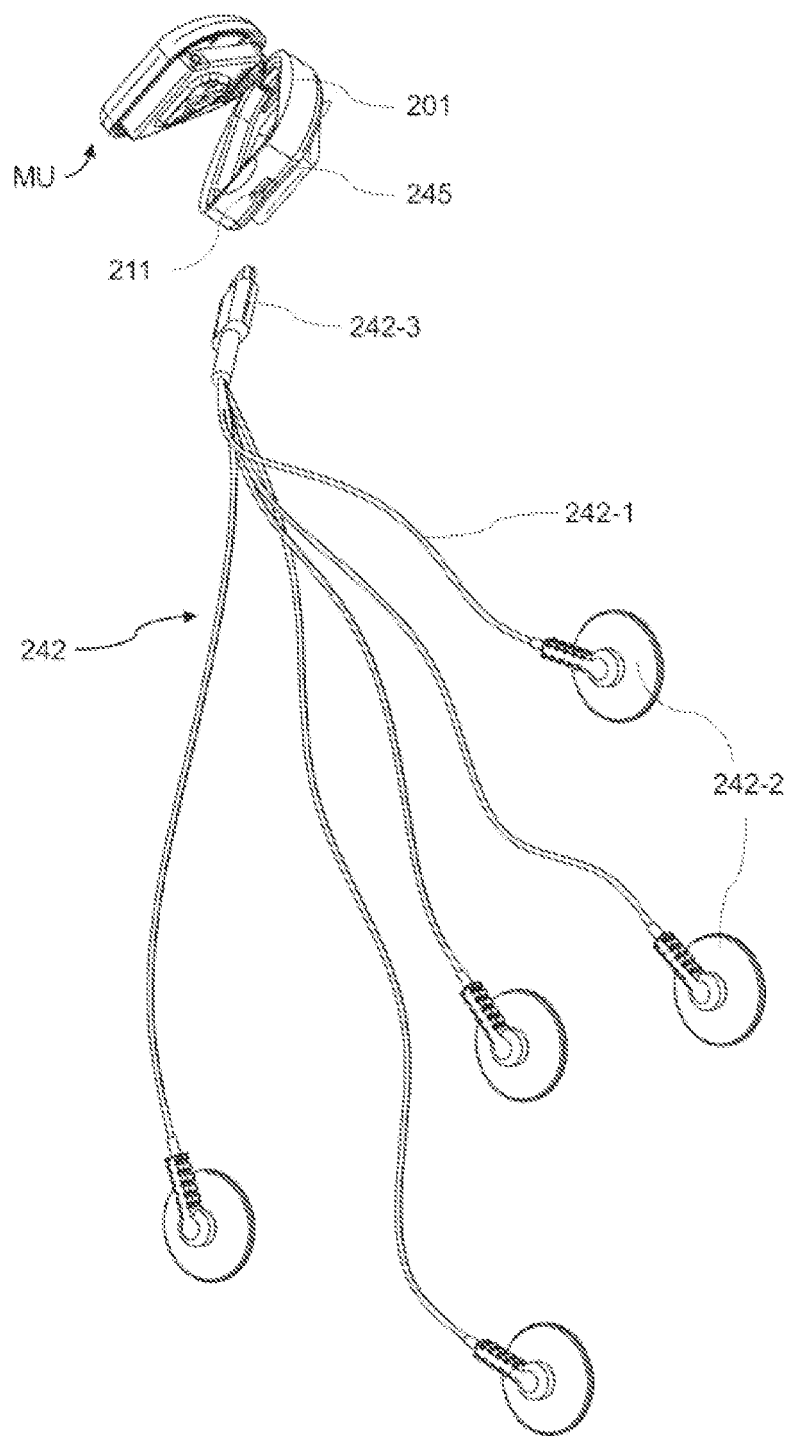

FIG. 12A illustrates the main unit connected to the sensor module—perspective view.

Figure 12B:
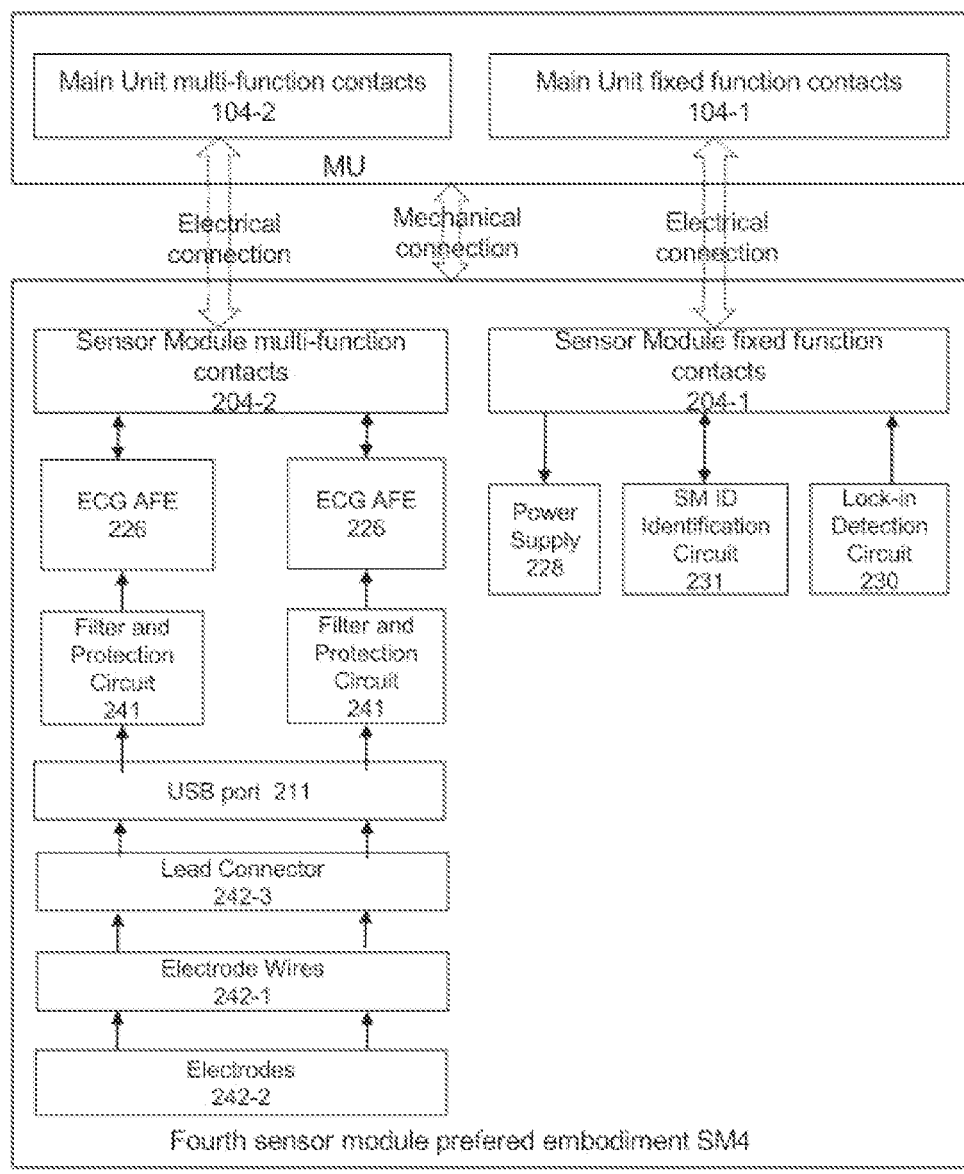

FIG. 12B illustrates the diagram of the electronic components of the sensor module.

Fifth Sensor Module Preferred Embodiment SM5

Figure 13A:
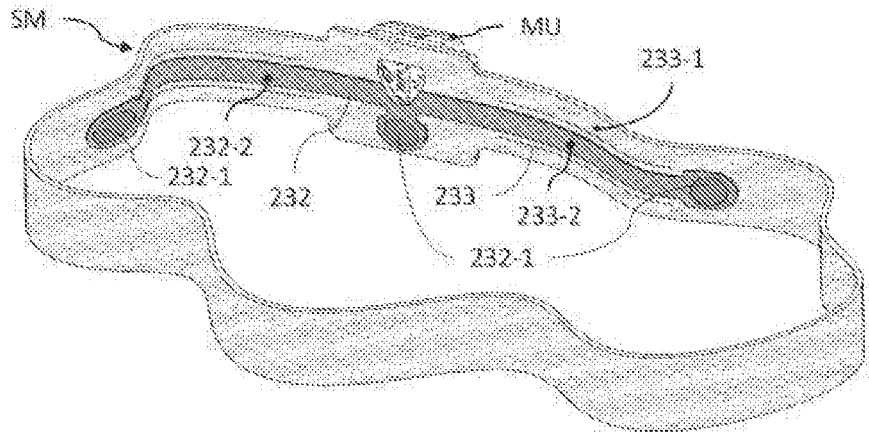

FIG. 13A illustrates the main unit connected to the sensor module—perspective view from patient skin's side.

Figure 13B:
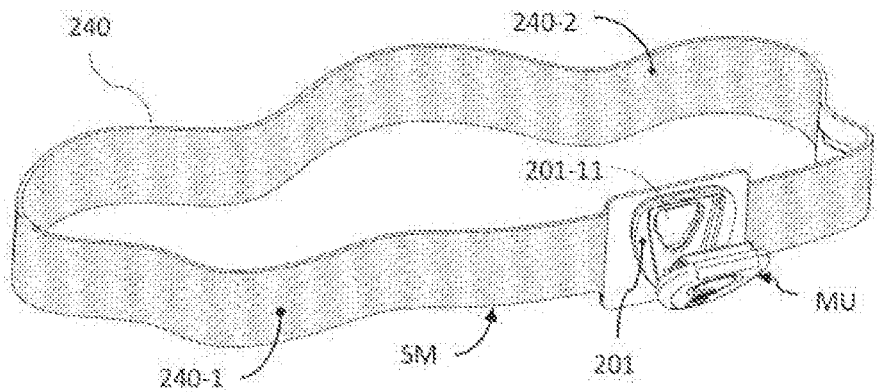

FIG. 13B illustrates the main unit connected to the sensor module—perspective view from the side opposite to patient skin's side.

Figure 13C:
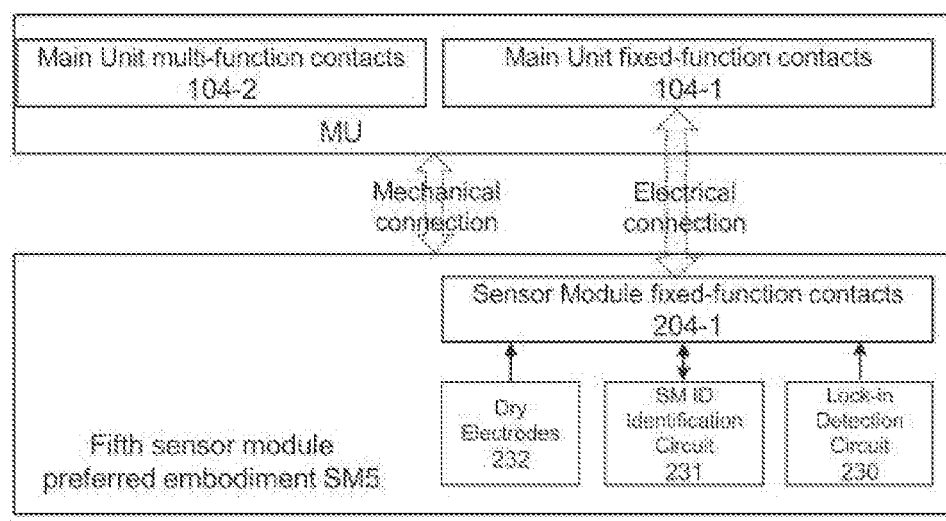

FIG. 13C illustrates the diagram of the electronic components of the sensor module.

Sixth Sensor Module Preferred Embodiment SM6

Figure 14A:
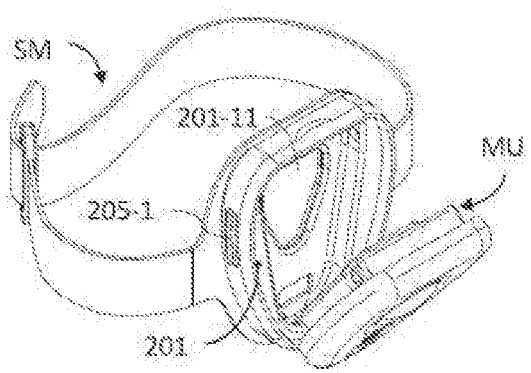

FIG. 14A illustrates the main unit connected to the sensor module—perspective view from the opposite side in respect to patient's skin.

Figure 14C:
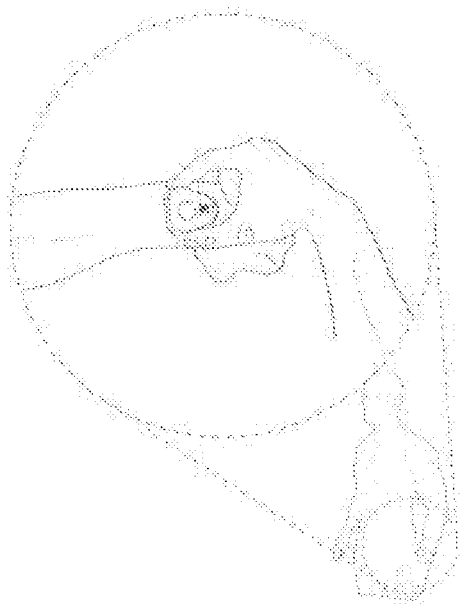
Figure 14B:
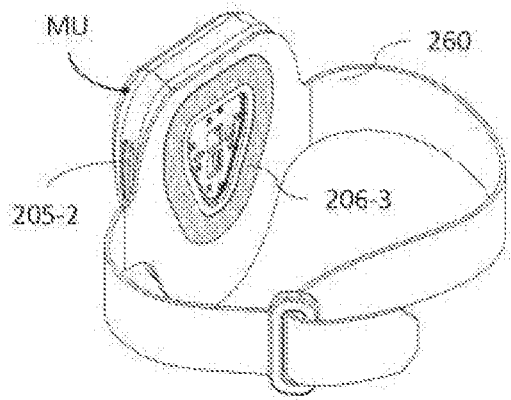

FIG. 14B illustrates the main unit connected to the sensor module—perspective view from the patient skin side.

FIG. 14C illustrates non-limiting examples of positioning the medical device corresponding to the sixth first preferred embodiment of the sensor module.

Figure 14D:
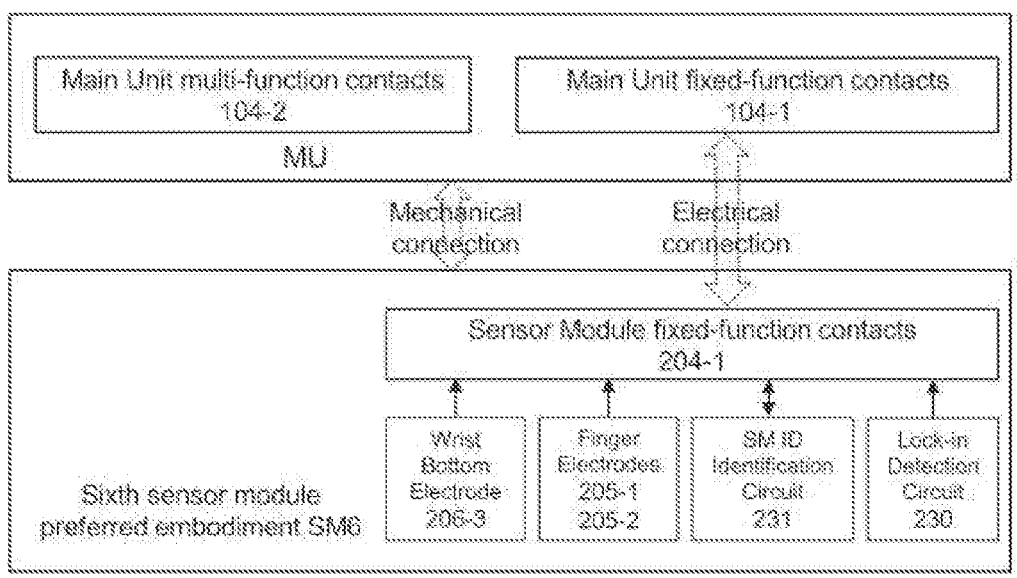

FIG. 14D illustrates the diagram of the electronic components of the sensor module.

Seventh Sensor Module Preferred Embodiment SM7

Figure 15A:
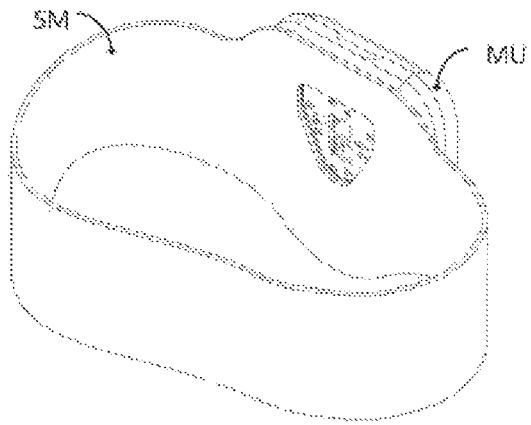

FIG. 15A illustrates the main unit connected to the sensor module—perspective view from patient skin's side.

Figure 15B:
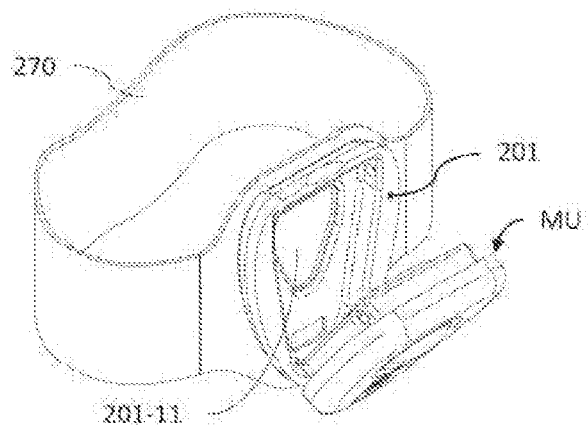

FIG. 15B illustrates the main unit connected to the sensor module—perspective view from the opposite side in respect to patient's skin.

Figure 15C:
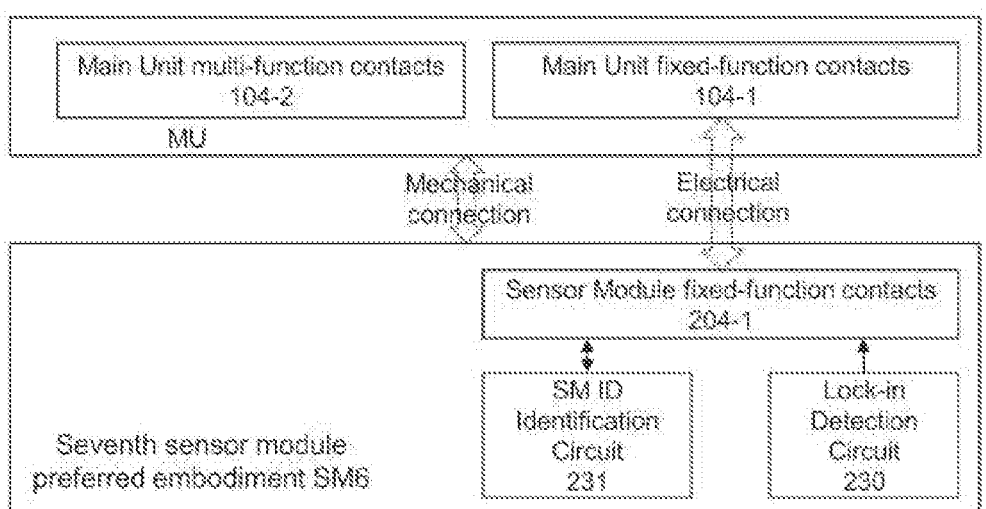

FIG. 15C illustrates the diagram of the electronic components of the sensor module.

External Devices

Figure 16:
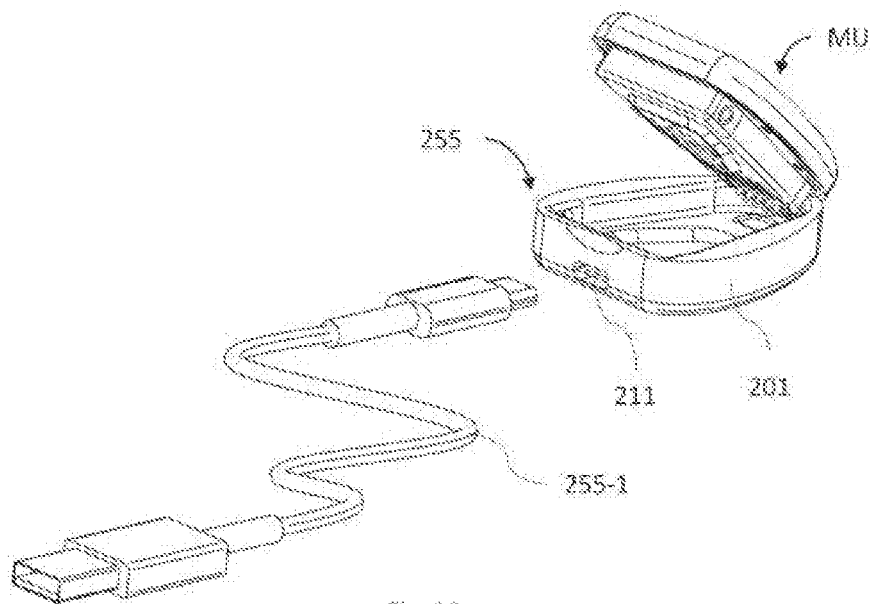

FIG. 16 illustrates an example of external device.

Figure 17:
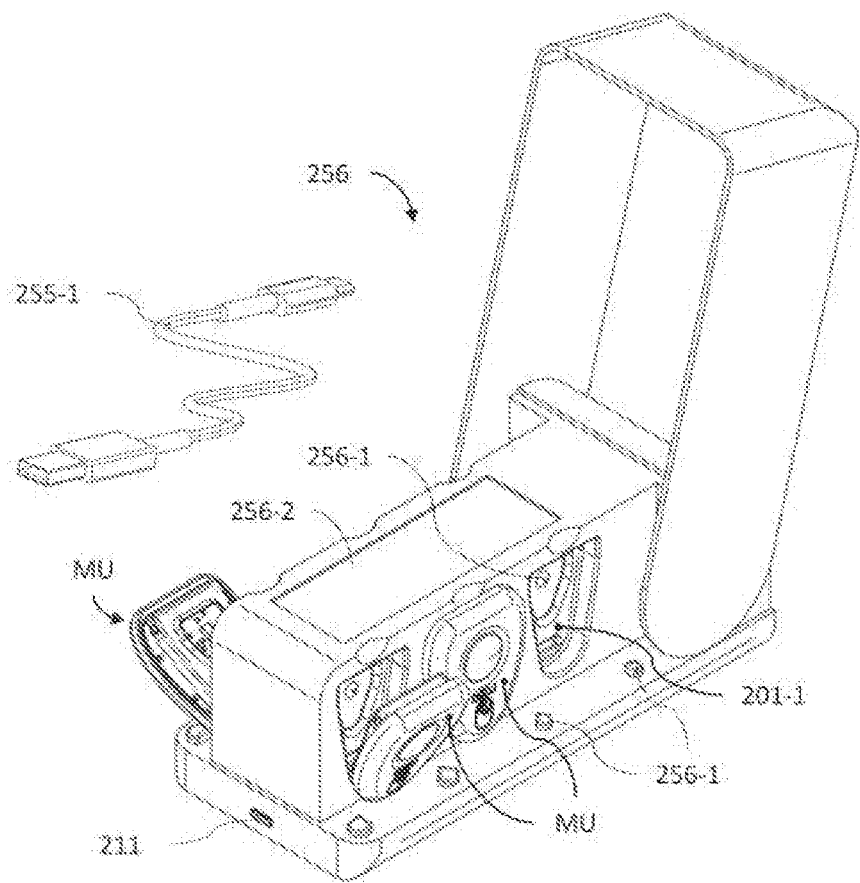

FIG. 17 illustrates another example of external device.

Method

Figure 18:
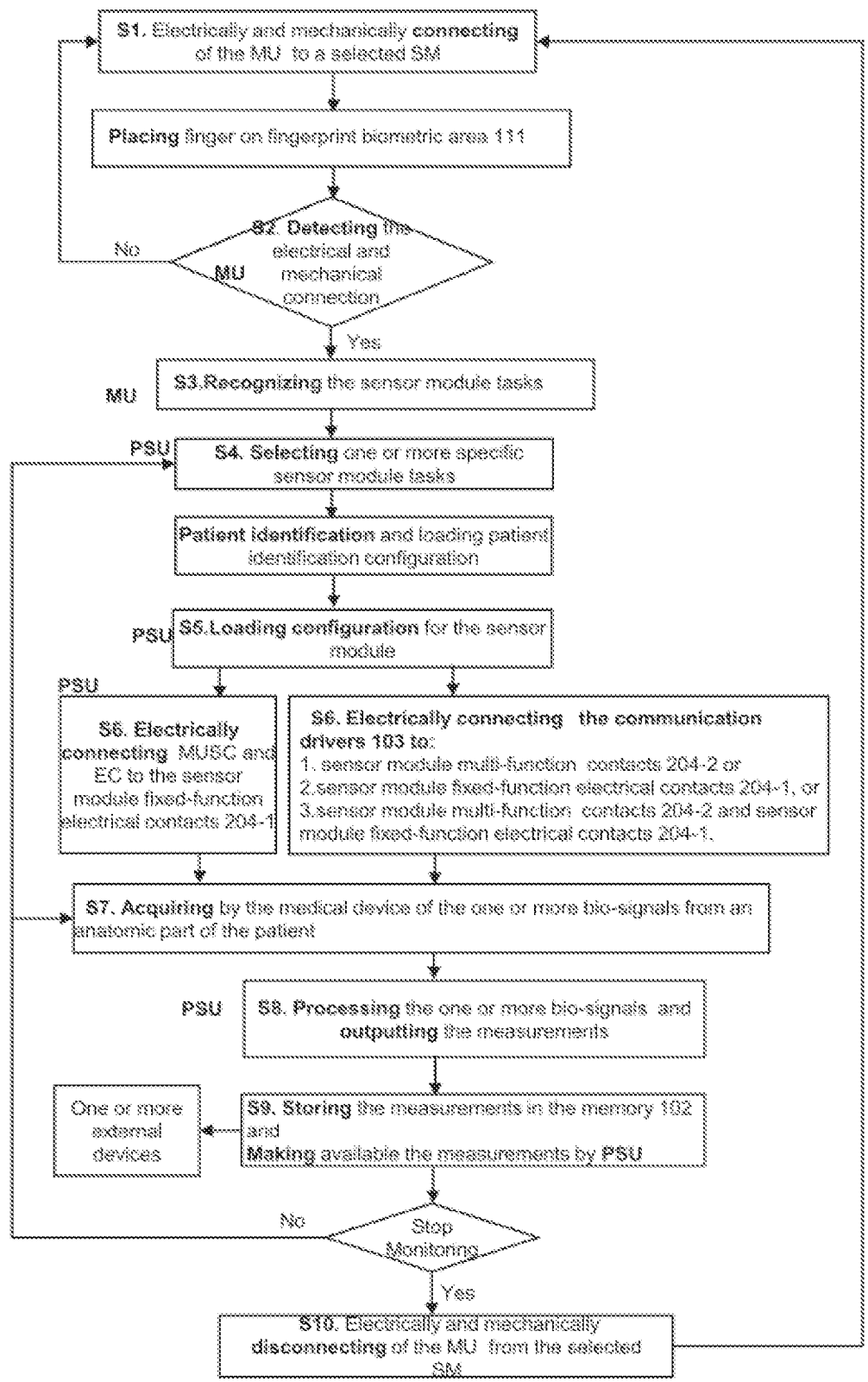

FIG. 18 illustrates the diagram of the method according to the invention.

DETAILED DESCRIPTION

First Aspect of the Invention

Figure 1:
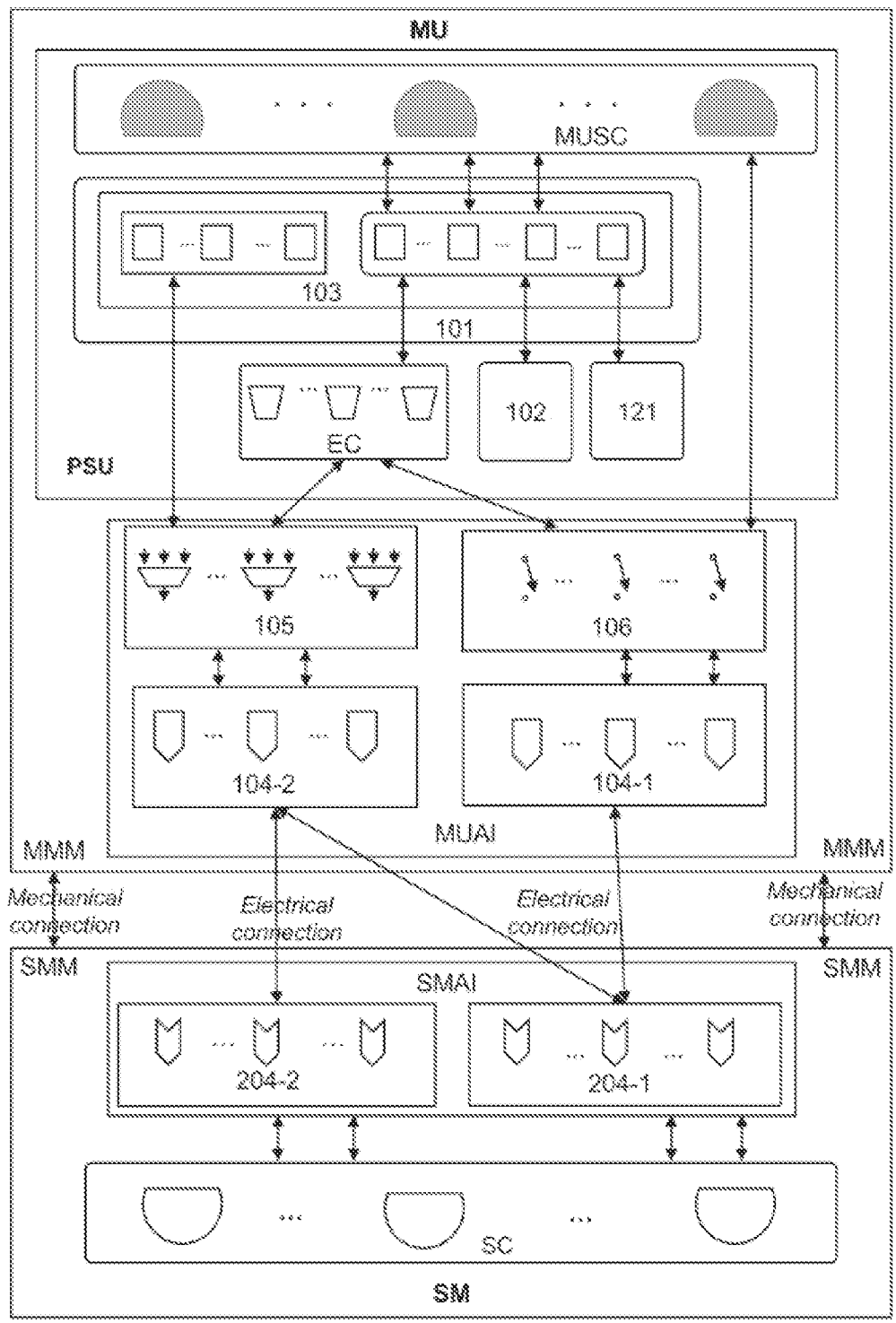
FIG. 1 illustrates a schematical diagram of the medical device of the invention.

Referring to FIG. 1, the invention is carried out by a modular medical device for monitoring health parameters of a patient, hereafter called in short medical device.

The medical device of the invention comprises a sharable main unit MU, hereafter called in short main unit MU electrically and mechanically connectable to a sensor module SM.

When the sensor module SM is electrically and mechanically connected to the main unit MU, the medical device of the invention is configured to acquire one or more bio-signals of the patient corresponding to an anatomic part of the patient, and the medical device is configured to carry out measurements of health parameters by means of configurations of the main unit MU and, respectively of the sensor module SM. Said respective configurations of the main unit MU and of the sensor module SM shall be detailed in this section. It shall be understood that the separate disclosure of the respective configurations of the main unit MU and of the sensor module SM is made only for the better understanding of the teaching of the invention. Throughout the invention, it shall be understood that all the configurations of the medical device to carry out the measurements of the health parameters apply when the sensor module SM is electrically and mechanically connected to the main unit MU.

In general, the sensors used for measuring the health parameters usually include some components that acquire the bio-signals from the patient, for example electric signals or acoustic signals, while other components pre-process and process the acquired bio-signals, the final result being the measurements expressed as meaningful parameters for the health specialist, e.g. heart rate, temperature, or blood oxygenation.

The medical device of the invention is based on two principles.

Figure 2:
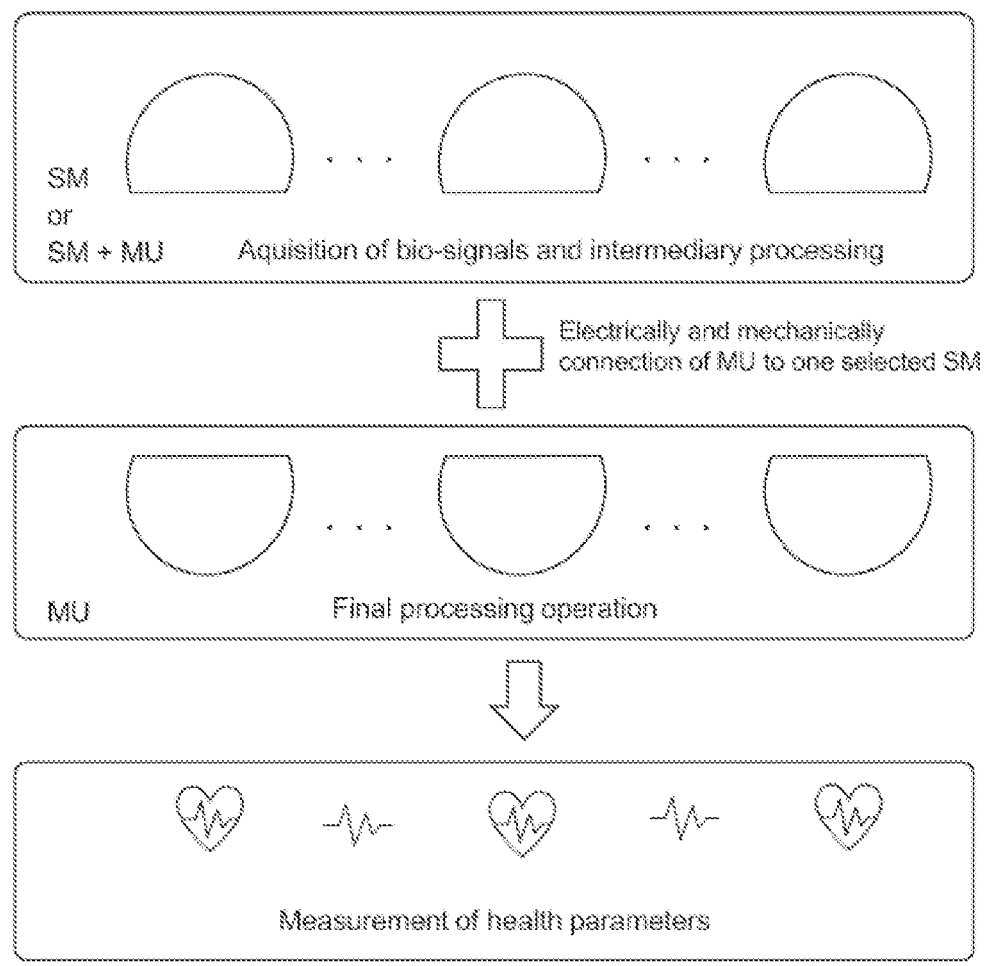
FIG. 2 illustrates symbolically the joint measurement of the main unit sensors' components and the sensor module sensors' components.

The first principle is to have either the sensor module SM or the main unit MU together with the sensor module SM configured for acquiring the bio-signals from the patient and the main unit MU configured for carrying out final processing operations of the bio-signals and outputting the measurements. The distributed tasks are depicted symbolically in FIG. 2 as first halves and second halves. All the processing operations except the final processing operations are hereafter called intermediary processing operations. Said intermediary processing operations are distributed among the sensor module SM and the main unit MU.

In this way, the final processing operations ending with the measurements, that in the prior art are carried out by each individual sensor, are carried out in the invention by the main unit MU. This leads to the advantage of overcoming the problems of prior art regarding the conflicting technical requirements among various sensors.

The second principle is that the invention discloses various sensor modules SM, which share the same main unit MU for the final processing operations, reason for which the full name of the main unit MU is sharable main unit MU, and, correspondingly, the full name of the medical device of the invention is modular medical device.

The patient uses a single selected sensor module SM at a time, selected among the various sensor modules SM disclosed in the invention, but he is able to use one sensor modules SM after another. Hereafter, for the ease of understanding of the invention, unless otherwise expressly stated, the term sensor module SM shall refer to the selected sensor module SM among the various sensor modules SM.

By implementing the two principles into the configurations of the medical device of the invention as disclosed herein, the medical device has the advantage of connecting and controlling a wide range of sensors to carry out different specific tasks, overcoming possible incompatibilities between the technical requirements of said sensors, without being too bulky and/or heavy or cumbersome.

The main unit MU comprises: main unit mechanical means MMM, a main unit array interface MUAI and a processors' sub-unit PSU.

The main unit mechanical means MMM is configured for detachable mechanical connection of the main unit MU to a sensor module mechanical means SMM of the sensor module SM. The shape of the sensor module SM is configured to accommodate partially the main unit MU within a sensor module cavity 201-1 of a sensor module receptacle 201 of the sensor module SM. The sensor module mechanical means SMM comprises:

- a guiding recess 201-2 corresponding to a guiding element 107 of the main unit for guiding the mechanical connection of the main unit MU within said sensor module cavity 201-1,
- two or more sensor module detent recesses 201-3, each sensor module detent recess 201-3 corresponding to a spring-loaded detent 108-1, of a spring-loaded detent mechanism.

The main unit array interface MUAI configured for electrical connection of the main unit MU to a sensor module array interface SMAI of the sensor module SM. The main unit array interface MUAI comprises:

- main unit fixed-function electrical contacts 104-1,
- main unit multi-function electrical contacts 104-2,
- one or more programmable multiplexer switches 105,
- one or more simple switches 106.

The processors' sub-unit PSU comprises:

- a main processor 101, the main processor 101 comprising communication drivers 103,
- a memory 102,
- main unit sensors' components MUSC,
- enabling components EC, the enabling components EC comprising at least:
  - a lock-in detection interface 130,
  - an identification interface SM ID 131.

The sensor module SM comprises: the sensor module mechanical means SMM, sensors' components SC, the sensor module array interface SMAI, and sensor module enabling components SEC.

The sensors' components SC are configured to carry out sensor module tasks.

The sensor module array interface SMAI are arranged within the sensor module cavity 201-1. The sensor module array interface SMAI comprise:

- sensor module fixed-function electrical contacts 204-1, or
- sensor module multi-function contacts 204-2, or
- sensor module fixed-function electrical contacts 204-1 and sensor module multi-function contacts 204-2.

The sensor module enabling components SEC comprise at least:

- a sensor module lock-in detection interface 230, the sensor module lock-in detection interface 230 configured to mate the lock-in detection interface 130 of the main unit MU,
- a sensor module identification interface SM ID 231, the sensor module identification interface 231 SM ID configured to mate the identification interface SM ID 131 of the main unit MU.

The terms "main processor" and "memory" shall be understood, respectively, as one or more processors, respectively one or more memories.

The main processor 101 is configured to carry out at least the final processing operations of the main unit MU, and to output the measurements of health parameters.

The memory 102 is configured to store at least the sensor module tasks of all the sensor modules SM, pre-determined processors' instructions that will be detailed hereafter, the processed measurements as outputted result of the method of the invention, as well as intermediary processing results of the intermediary processing operations.

The communication drivers 103 are configured to ensure data and command transmission from the main processor 101 to the main unit multi-function electrical contacts 104-2 by means of the one or more programmable multiplexer switches 105 by using communication protocols either directly to said main unit multi-function electrical contacts 104-2 or by means of the enabling components EC, as shown in FIG. 1 and FIG. 7A.

The communication drivers 103 are configured to ensure data and command transmission from the main processor 101 to the main unit fixed-function electrical contacts 104-1 by means of the enabling components EC and of the one or more simple switches 106 as shown in FIG. 1.

Non-limiting examples of communication drivers are: Serial Peripheral Interface SPI, Inter-Integrated Circuit I2C, Universal Serial Bus USB, Inter-IC Sound I2S, Universal Synchronous Receiver UART, General-Purpose Input/Output GPIO, Secure Digital Input Output SDIO.

The sensor module tasks refer to the configurations for acquiring the bio-signals from the patient and sending the acquired bio-signals to the sensor module array interface SMAI, with or without intermediary processing of said acquired bio-signals by the sensor module SM.

A typical non-limiting example of sensor module tasks is acquiring electric signals from the heart of the patient necessary to carry out an electrocardiogram.

The sensor module array interface SMAI is configured for mating the main unit array interface MUAI.

In some situations, it is sufficient for the sensor module array interface SMAI to have only the sensor module fixed-function electrical contacts 204-1, complementary to the main unit fixed-function electrical contacts 104-1. A non-limiting example is the first sensor module preferred embodiment.

In other situations, the sensor module array interface SMAI comprises the sensor module fixed-function electrical contacts 204-1 and sensor module multi-function electrical contacts 204-2, the sensor module multi-function electrical contacts 204-2 being complementary to main unit multi-function electrical contacts 104-2. A non-limiting example is the second sensor module preferred embodiment, where both fixed-function and multi-function electrical contacts are used.

The mechanical connection of the main unit MU to the sensor module SM must ensure, on one hand, that the main unit MU remains firmly engaged to the sensor module SM ensuring their electrical connection while carrying out the measurements, and, on the other hand, the sensor module SM can be easily detached from the main unit MU once the measurements are ended.

FIG. 3 shows the principles of mechanical connection.

It shall be understood that the shape of the main unit MU and, correspondingly of the sensor module SM, as represented in FIG. 3, is not limiting the scope of the invention. The respective shapes and the dimensions of the main unit MU, and, respectively of the sensor module SM, depend on the possibility given by the technology to accommodate all the components disclosed in this invention on one hand, and the handy use of the main unit MU and, correspondingly of the sensor module SM by the patient, on the other hand.

Figure 3A:
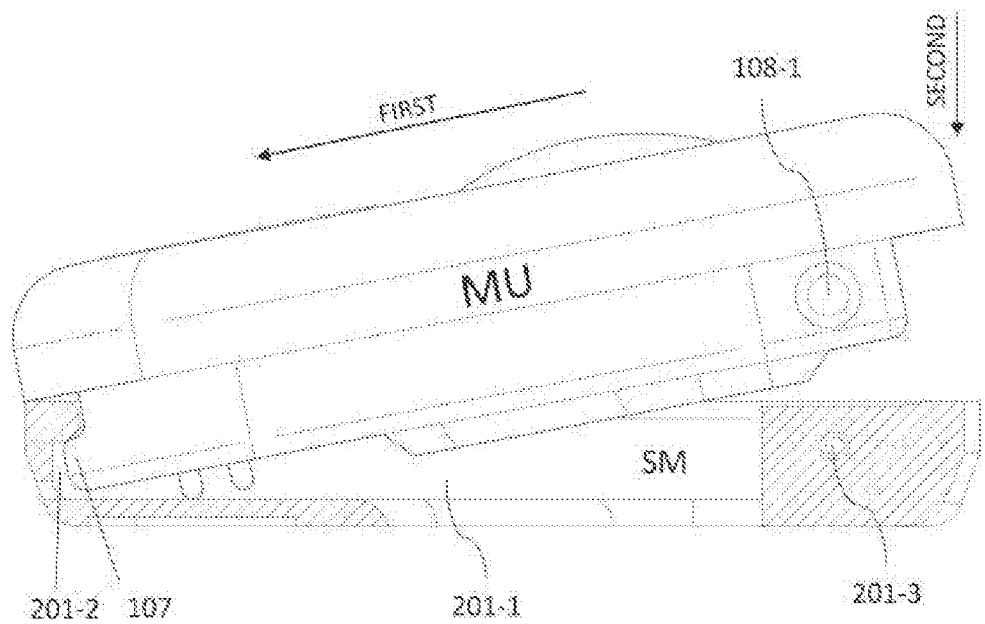
FIG. 3A illustrates the principles of mechanical connection of the main unit to the sensor module in a longitudinal cross-section.

The configurations of the main unit mechanical means MMM and, respectively, of the sensor module mechanical means SMM are such that to ensure the handy attachment and detachment of the main unit MU to the sensor module SM, using the sequence of operations marked with "first" and "second" in FIG. 3A.

Figure 3B:
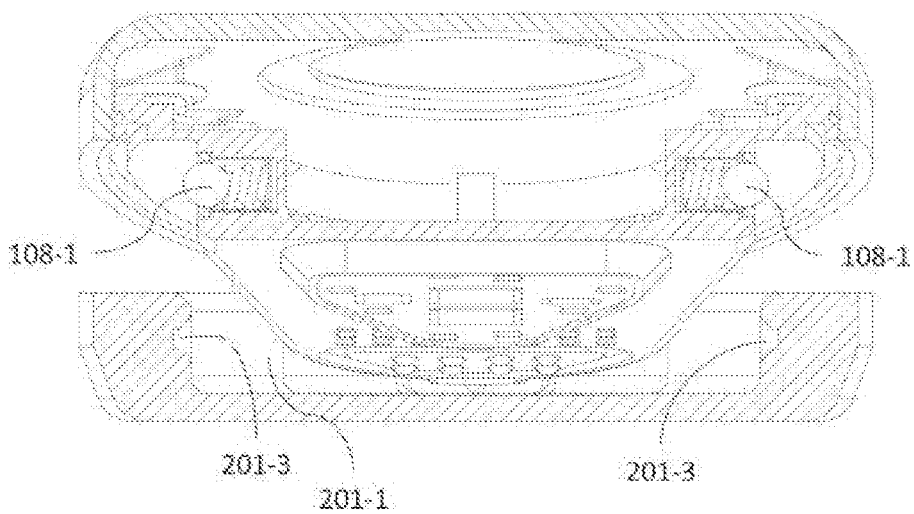
FIG. 3B illustrates the principles of mechanical connection of the main unit to the sensor module in a transverse cross-section.

With reference to FIG. 3A and FIG. 3B, the main unit mechanical means MMM comprises:
  a guiding element 107 for centering the main unit MU on the sensor module SM when the main unit MU is being accommodated in the sensor module SM, corresponding to the first operation marked with "first" in FIG. 3A,
  a spring-loaded detent mechanism comprising two or more spring loaded detents 108-1, each spring-loaded detent 108-1 accommodated in a corresponding spring-loaded detent hole, corresponding to the second operation marked with "second" in FIG. 3A.

The spring-loaded detents 108-1 can be either mechanical or magnetic. The number of spring-loaded detents 108-1 is limited by the possibility to action them by the patient, reason for which, preferably, the number of spring-loaded detents 108-1 is two or three.

As shown in FIGS. 3A and 3B, the sensor module receptacle 201 has the sensor module cavity 201-1 configured for partially accommodating the main unit MU within said sensors' unit cavity 201-1.

In order to ensure the firm engagement of the main unit MU to the sensor module SM while carrying out the measurements, the shape of the part of the sensor module receptacle 201 matches the shape of the corresponding part of the main unit MU that is accommodated within said sensors' unit cavity 201-1.

The dimension of the sensor module cavity 201-1 is such that to ensure the firm engagement of the main unit MU to the sensor module SM. The shape and dimension of the two sensor module detent recesses 201-3 are such that to ensure handy connection and disconnection of the sensor module SM from the main unit MU.

The respective shapes of the guiding element 107, of the spring-loaded detent 108-1 of the sensor module cavity 201-1, of the guiding recess 201-2 and of the sensor module detent recesses 201-3 as seen in FIG. 3A are for exemplification only and shall not be considered as limiting.

[1] When the sensor module SM is mechanically connected to the main unit MU, the main unit fixed-function electrical contacts 104-1 are configured to be connected to the sensor module fixed-function electrical contacts 204-1, whereas the main unit multi-function electrical contacts 104-2 are configured to be selectively connected to one of the three selected from the below list:
  to the sensor module multi-function contacts 204-2, or
  to the sensor module fixed-function electrical contacts 204-1, or
  to the sensor module multi-function contacts 204-2 and to the sensor module fixed-function electrical contacts 204-1.

[2] The main unit sensors' components MUSC are electronic components that are configured for use together with the sensors' components SC for carrying out some of the measurements of health parameters.

The enabling components EC are electronic components that are not sensors' components, but are configured to enable the use of the main unit sensors' components MUSC together with the sensors' components SC.

With reference to FIG. 1 and FIG. 7B, the one or more simple switches 106 are configured for connecting the main unit sensors' components MUSC and the enabling components EC to the main unit fixed-function electrical contacts 104-1, for enabling the mating of the main unit fixed-function electrical contacts 104-1 with the sensor module fixed-function electrical contacts 204-1. FIG. 7B is simplified in respect to FIG. 1 to ease the understanding of the connections through the one or more simple switches 106.

With reference to FIG. 1 and FIG. 7A, the one or more programmable multiplexer switches 105 are configured for selectively connecting the communication drivers 103 and the enabling components EC to the main unit multi-function electrical contacts 104-2, for enabling the mating of the main unit multi-function electrical contacts 104-2 with the sensor module multi-function contacts 204-2, or with to the sensor module fixed-function electrical contacts 204-1, or with the sensor module multi-function contacts 204-2 and the sensor module fixed-function electrical contacts 204-1. FIG. 7A is simplified in respect to FIG. 1 to ease the understanding of the connections through the one or more programmable multiplexer switches 105.

The main unit fixed-function electrical contacts 104-1 have the same configuration for connecting all the sensor modules SM.

The main unit multi-function electrical contacts 104-2 have specific configuration for each sensor module SM.

The selective connection is enabled due to the configurations of each programmable multiplexer switch 105 that has one or more inputs from the communication drivers 103 and the enabling components EC and a sole output to one of the main unit multi-function electrical contacts 104-2.

With reference to FIG. 7C, non-limiting examples of further enabling components EC are as follows:
a buzzer 116,
a haptic interface controller 117,
a display interface 119,
a power management unit 120,
a wireless connection module 121,
an artificial intelligence processor 124,
a power output interface 128,
an USB interface 129.

[3] There are two mandatory enabling components for all the sensor modules SMs: the lock-in detection interface 130, and the identification interface SM ID 131.

The lock-in detection interface 130 is configured together with the sensor module lock-in detection interface 230 to detect when the electrical and mechanical connection of the sensor module SM to the main unit MU is established.

The identification interface SM ID 131 is configured together with the sensor module identification interface SM ID 231 to recognize the sensor module SM connected to the main unit MU and the associated sensor module tasks of said connected sensor module SM that are loaded in the memory 102.

With reference to FIG. 7C, non-limiting examples of main unit sensors' components MUSC are as follows:
a contact microphone array 122,
a voice microphone 123,
a motion sensor 125,
a first electrocardiogram analogue front end ECG AFE component 126,
a bio-impedance component 127,
an ECG/BI electrode interface 132.

Throughout the invention, the term "an ECG/BI electrode interface 132" includes one or more ECG/BI electrode interfaces 132, each ECG/BI electrode interface 132 configured for different anatomical part where the various electrodes of the sensor modules SM as described in the invention acquire the electrical signals depending on electrode types like dry or wet electrodes, body and electrode impedance corresponding to said anatomical part.

[3] The processors' sub-unit PSU is configured to comprise pre-determined processors' instructions stored in the memory 102. The pre-determined processors' instructions include but do not limit to the following:
instructions for detection of the sensor module SM when the sensor module SM is electrically and mechanically connected to the main unit MU.

These instructions enable the processors' sub-unit PSU to recognize that a sensor module SM is electrically and mechanically connected to the main unit MU. These instructions include the powering on of the sensor module SM, where applicable.

instructions for the recognition of the associated sensor module tasks.

These instructions enable the processors' sub-unit PSU to recognize when the electrical and mechanical connection of the sensor module SM to the main unit MU is established and which are the associated sensor module tasks of said connected sensor module SM that are loaded in the memory 102.

This is carried out due to the configurations of a lock-in detection pair of corresponding electrical contacts: a main unit lock-in detection fixed-function electrical contact 104-1 configured to connect to a sensor module lock-in detection fixed-function electrical contact 204-1. The lock-in detection pair of corresponding electrical contacts communicates with the processors' sub-unit PSU by means of the lock-in detection interface 130.

instructions for selection of one or more specific sensor module tasks.

The instructions for selection of one or more specific sensor module tasks enable the processors' sub-unit PSU to select, from the total number of sensor module tasks of the sensor module SM, the one or more specific sensor module tasks which are useful for the measurements. For example: selecting the task of using photoplethysmography PPG together with electrocardiograph ECG from the patient's finger thumb or performing lung auscultation with the stethoscope sensor, both types of tasks being carried out by the same sensor module SM.

instructions for loading configuration for sensor module SM, corresponding to one or more specific sensor module tasks.

These instructions enable the processors' sub-unit PSU to load the appropriate configuration for the selected sensor module SM either from the memory 102 or, for the embodiments where the main unit includes the wireless connection module 121, said appropriate configuration can be received by said wireless connection module 121 for example from a specific external device.

instructions for connecting, by means of the one or more simple switches 106, of the main unit sensors' components MUSC and the enabling components EC to the sensor module fixed-function electrical contacts 204-1, for the one or more selected specific sensor module tasks, according to the configuration,
instructions for selectively connecting, based on the one or more selected specific sensor module tasks, of the communication drivers 103 to the sensor module multifunction contacts 204-2 or to the sensor module fixed-function electrical contacts 204-1, or to the sensor module multi-function contacts 204-2 and the sensor module fixed-function electrical contacts 204-1, according to the configuration.

Each sensor module SM requires one or more specific communication drivers 103 from the total number of communication drivers 103 available for the communication of the sensor module array interface SMAI with the main processor 101.

For the embodiments when the sensor module SM does not comprise the sensor module multi-function electrical contacts 204-2, the instructions for dynamically assignment de-activate the main unit multi-function electrical contacts 104-2.

instructions for processing the measurements.

The instructions for processing the measurements enable the processors' sub-unit PSU to process the measurements carried out by the medical device of the invention that is to carry out the intermediary processing operations and the final processing operations. The processing instructions include but are not limited to: instructions for fusion of the measurements, formatting the measurements to predefined formats, instructions avoiding conflicts in fusing various measurements, patient safety instructions sensor, data intermediary processing signal conditioning instructions, etc.

instructions for storage of the measurements, and instructions for making available the measurements of health parameters to one or more external devices in order to be used for monitoring the health parameters of the patient.

The instructions for processing the measurements enable the processors' sub-unit PSU to store the processed measurements carried out by the medical device of the invention in the memory 102 as a patient data file, instructions for electrically disconnecting of the main unit MU from the sensor module SM sent through to lock-in detection interface 130 lock-in to the detection pair of corresponding electrical contacts.

Thus, the lock-in detection interface 130 is configured to disconnect the main unit lock-in detection fixed-function electrical contact 104-1 from the corresponding module lock-in detection fixed-function electrical contact 204-1.

Preferred Embodiments of the Main Unit MU

With reference to FIG. 4A, FIG. 4B, FIG. 5, FIG. 6B, in a first main unit preferred embodiment, the main unit MU further comprises a skin sensors' island area 109.

The skin sensors' island area 109 comprises one or more main unit optical sensors 109-1, each of the one or more optical sensors 109-1 comprising:
one or more light sources arranged to emit light through one or more light-transfer optical components 109-13,
one or more light-detectors, arranged to detect light through the one or more light-transfer optical components 109-13,
one or more skin sensors' island sub-areas, comprising:
one or more main unit temperature sensors 109-141 configured to sense through the one or more light-transfer optical components 109-13.

The shape and the materials of the skin sensors' island area 109 are such that to enable the optical sensors' components to emit, respectively detect light through the one or more light-transfer optical components 109-13. The shape and the material of the skin sensors' island sub-areas are such that to enable the one or more main unit contact and/or contactless temperature sensors 109-141 to sense through the skin sensors' area 109.

The one or more main unit optical sensors 109-1 and the one or more main unit temperature sensors 109-141 belong to the category of the main unit sensors' components MUSC.

Non-limiting examples of optical sensors 109-1 are: photoplethysmography PPG, photodiodes, charge-connected device CCD sensors, complementary metal-oxide-semiconductor CMOS sensor, etc.

Each light-detector is spatially separated by each light source by a light separation distance dn.

Each light-detector together with each light source are configured to generate a light path.

The light separation distance dn is comprised between a pre-determined minimum light separation distance MIN-dn and a pre-determined maximum light separation distance MAX-dn, the pre-determined minimum light separation distance MIN-dn and the pre-determined maximum light separation distance MAX-dn, depending on a signal quality parameter such as the perfusion index of the anatomic part of the patient.

Said perfusion index PI is the ratio of the pulsatile blood flow to the non-pulsatile or static blood in peripheral tissue of the anatomic part of the patient.

Figure 4A:
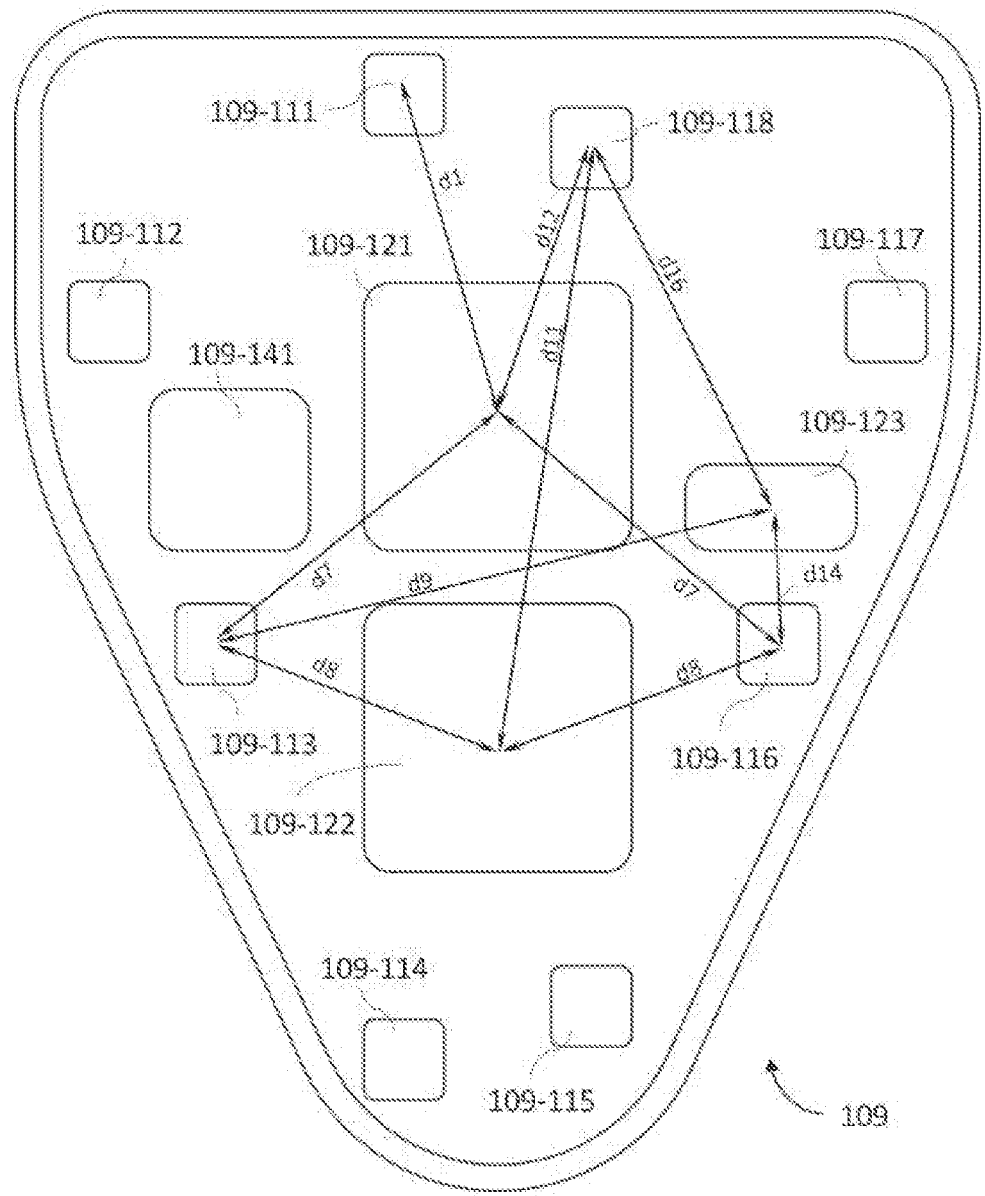
FIG. 4A illustrates the skin sensors' island area.
Figure 4B:
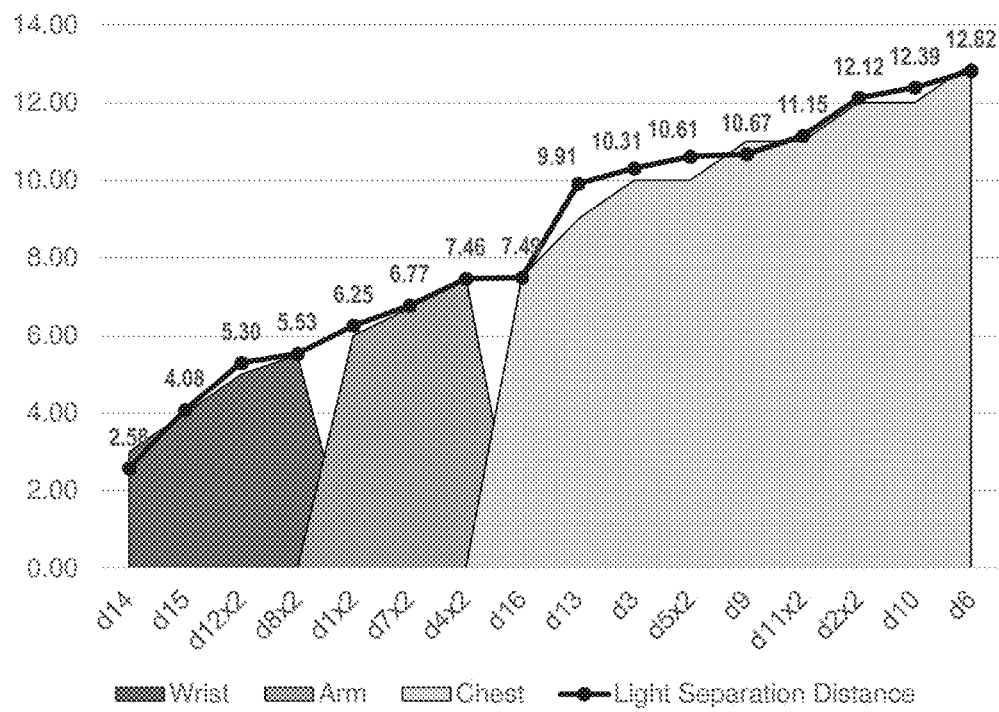
FIG. 4B illustrates an example of the light path distances dn.

A non-limiting example of realization is shown in FIG. 4A and FIG. 4B, where the light sources are represented by eight light emitting diodes LEDs with reference numbers from 109-111 to 109-118 and the light detectors are represented by 3 photodiodes with reference numbers from 109-121 to 109-123.

In the example of FIG. 4A, the number of light paths 109-15 is 24 resulting from the combination of the 8 light emitting diodes LEDs from 109-111 to 109-118 and 3 photodiodes from 109-121 to 109-123. For the sake of clarity, only part of the light separation distances dn are represented in FIG. 4A, in particular the light separation distance d1 between the light emitting diode LED 109-111 and the photodiode 109-121, the light separation distance d12 between the light emitting diode LED 109-118 and the photodiode 109-121, etc.

The example of realization is shown in FIG. 4A and FIG. 4B illustrates the dynamically configurable optical sensor light path for a range of anatomically body places with different perfusion indexes.

In some cases, the skin sensors' island area 109 further includes: contact microphones, radar sensor, ultrasound piezo sensor, laser interferometer sensor for micro skin/blood vessels displacement detection, not represented graphically.

When the light separation distance dn enables best signal quality for the respective anatomic part and the specific measurement, the light separation distance dn becomes an optimal light separation distance dn. Taking as example the photoplethysmography PPG sensor, the best signal quality for reflective PPG sensor for various anatomic parts of the patient requires different geometrical separation distances between the light sources and the light-detectors.

For example, in the non-limiting example of realization is shown in FIG. 4A, if the anatomical part is the wrist, the light separation distances dn varies between 2.58-5.53 mm; if the anatomical part is the arm, the light separation distances dn varies between 6.25-7.46 mm; whereas if the anatomical part is the chest, the light separation distances dn varies between 7.49-12.82 mm, as it is shown in FIG. 4B.

As seen in FIG. 4A, different geometrical configuration of the light emitting diodes LEDs 109-111 to 109-118 and of the photodiodes 109-121 to 109-123 was chosen such that to cover all range of optimal light separation distance dn in the range between the pre-determined minimum light separation distance MIN-dn=2 mm and the pre-determined maximum light separation distance MAX-dn=13 mm in order to cover with a single photoplethysmography PPG the three anatomic parts of this non-limiting example: wrist, arm, chest.

In one example of this embodiment, the one or more light-transfer optical components for the one or more optical sensors 109-1 comprises an optically transparent or a translucent material arranged to face the skin of the patient. Facing of the skin of the patient may be carried out either in physical contact with the patient or without physical contact, ensuring only optical contact.

In a second main unit preferred embodiment, with reference to FIG. 5 and FIG. 6A, the medical device is configured to be used by two or more patients by further comprising means for identifying the patient including at least:
- a fingerprint biometric area 111, configured to acquire the unique identification characteristics of physical features data of the patient,
- one or more biometric sensors 112 included in the processors' sub-unit PSU, configured to identify the patient data file based on the physical features data acquired by the fingerprint biometric area 111.

The biometric sensors 112 belong to the category of the main unit sensors' components MUSC.

In a third main unit preferred embodiment, with reference to FIG. 1, the processors' sub-unit PSU further comprises the wireless connection module 121, configured to connect the main unit MU to the one or more external devices in order to be use the measurements for monitoring the health parameters of the patient.

Said external devices can be handheld devices such as phone, tablets, or processing units such as computers, laptops, or storage devices including the cloud or cloud-like storage means.

It is advantageous to have the wireless connection module 121 as unique, centralized connection to the one or more external devices regardless of the selected sensor modules SM.

In a fourth main unit preferred embodiment, with reference to FIG. 7C, the processors' sub-unit PSU further comprises the artificial intelligence processor 124, configured for:
- processing the measurements of health parameters received from one or more of the following: the main processor 101, one or more external sensors,
- running artificial intelligence models on edge and classifying the measurements of health parameters according to health criteria,
- sending classified measurements of health parameters to the main processor 101,
- making available by the main processor 101 of the classified measurements of health parameters to one or more external devices.

Example of Realization for the Main Unit MU

With reference to FIG. 5, FIG. 6A, FIG. 6B, FIG. 7A, FIG. 7B, FIG. 7C, the invention discloses an example of realization of the main unit MU for an easier understanding of the invention.

The shape and the size of main unit MU of the invention is such that the main unit can be easily held in the hand of the patient or worn on the body. The main unit MU of the invention is configured to be connected to the sensor module SM on one side of the main unit MU.

The shape of the MU of the example of realization is symmetrical and oval-shaped, having a narrower portion and a wider portion. This shape is one of the numerous shapes possible without departing from the scope of the invention. Other possible shapes are: round, squared, irregular shape.

It shall be understood that the shape of the components exemplified hereafter and their relative positioning is not limiting the invention.

The main unit MU of the example of realization illustrates a combination of all the previously-disclosed preferred embodiments as it includes the skin sensors' island area 109, the means for identifying the patient and the artificial intelligence processor.

The following components of the main unit MU are disclosed hereafter starting from the side opposite to the side of connection the main unit MU to the sensor module SM.

As represented in FIG. 5, the main unit MU has a top cover 113, a bottom cover 114, one or more batteries 110, and one printed circuit board PCB 115 on which the respective subcomponents of the processors' sub-unit PSU and of the main unit sensors' components MUSC as well as the one or more biometric sensors 112 are placed according to known techniques. The person skilled in the art knows that it is possible to use two or more printed circuit boards PCB 115 to accommodate the afore-mentioned electronic components without departing from the teaching of the invention, as FIG. 5 shows for simplicity a single printed circuit board PCB 115.

The printed circuit board PCB 115 further accommodates the artificial intelligence processor 124, not represented graphically in FIG. 5 but represented in FIG. 7C.

FIG. 5 also discloses a buzzer 116, placed on the printed circuit board PCB 115 configured to provide acoustic feedback such as when the measurements detect anomalous values, or when there is an error which prevents the medical device to function properly.

The printed circuit board PCB 115 may further accommodate a haptic interface controller 117, a wireless connection module 121 such as Bluetooth, RFID, GSM, GPS module, an electromagnetic shield.

In this example of realization, the one or more biometric sensors 112 and the buzzer 116 are fixed on the top cover 113. The main unit fixed-function electrical contacts 104-1 and the main unit multi-function electrical contacts 104-2 are either accommodated on a separate PCB, not represented graphically, or directly inserted in the material of the bottom cover 114, for example by using the over molding injection technique.

The one or more batteries 110 are configured to power the main unit MU, according to prior art.

The top cover 113 has a button hole 113-1 and an on-off button 113-2 accommodated in the button hole 113-1. When the on-off button 113-2 is pressed by the patient, once the main unit MU is mechanically connected to the sensor module SM, the electrical connection is established, and the medical device of the invention can be used. The presence of the on-off button 113-2 is optional in the main unit MU, as the main unit MU can be powered on when mechanically and electrically connected to the sensor module SM and, when not in use, can be configured to entry into a stand-by mode.

The fingerprint biometric area 111 is placed on the top cover 113, as seen in FIG. 5 and FIG. 6.

The bottom cover 114 accommodates the main unit mechanical means MMM, as seen from FIG. 6, FIG. 7A and FIG. 7B. In this example, the guiding element 107 is placed centrally in the narrower portion of the main unit, the spring-loaded detent mechanism is mechanical and the number of spring-loaded detents 108-1 is two, placed symmetrically in respect to the guiding element 107.

The bottom cover 114 has an outer gasket 114-1 and an inner gasket 114-2. The outer gasket 114-1 is configured to seal the bottom cover 114 so that the medical device be water-resistant or waterproof once the main unit MU mechanically connected to the sensor module SM.

FIG. 6B show schematically the main unit fixed-function electrical contacts 104-1 and the main unit multi-function electrical contacts 104-2, the graphical representation of which is symbolical and not limitative.

As represented in FIG. 6B, the portion surrounding the fixed-function electrical contacts 104-1 is sealed by the inner gasket 114-2. It is possible that the inner gasket 114-2 seals the main unit multi-function electrical contacts 104-2 or the main unit fixed-function electrical contacts 104-1 and the main unit multi-function electrical contacts 104-2.

The inner gasket 114-2 has double role: on one side reinforcing the sealing against water, including patient's sweat, for the respective electrical contacts and, on the other side, compensating for a possible height difference of the portion surrounding the respective electrical contacts and the general surface of the bottom cover 114 facing the sensor module SM.

In FIG. 5 and FIG. 6A, FIG. 6B, the skin sensors' island area 109 is shown schematically, including the optically transparent or a translucent material arranged to face the skin of the patient.

As shown in FIG. 7C, in this non-limiting example of realization, for powering the medical device, the main processor 101 communicates with the power management unit 120, the power management unit 120 being in contact with the battery 110 and with the power output interface 128, the power output interface 128 being configured to power the sensor module SM.

As shown in FIG. 7C, the main processor 101 communicates with the memory 102, with the communication drivers 103, with the main unit sensors' components MUSC and with the enabling components EC for transmitting the instructions through the one or more programmable multiplexer switches 105 and through the one or more simple switches 106.

With reference to FIG. 7B and FIG. 7C, non-limiting examples of the main unit sensors' components MUSC with whom the main processor 101 communicates are as follows:
  the biometric sensor 112,
  the contact microphone array 122, placed on the skin sensors' island area 109 and configured to acquire from the skin of the patient the sounds of the heart and lungs when used with the sensor module SM of the first sensor module preferred embodiment,
  the voice microphone 123, placed on the printed circuit board PCB 115 that is closest to one of the edges of the main unit MU, being configured to acquire sounds from the ambiance, including voice commands—such as "call 911", or dictate notes to avoid writing them, and configured for noise cancelation when one of the skin contacts microphones are activated, when used with the sensor module SM of the first sensor module preferred embodiment, or by means of the sensor module SM of the second sensor module preferred embodiment,
  the motion sensor component 125 configured to help filtering the noise of the electric signals acquired from the patient by means of the sensor module SM of the first sensor module preferred embodiment, or to count patient steps or activity level.
  the first electrocardiogram analogue front end ECG AFE component 126, configured to convert the electric signals acquired from the patient by means of the sensor module SM for outputting the electrocardiogram of the first sensor module preferred embodiment, or by means of the sensor module SM of the second sensor module preferred embodiment,
  the bio-impedance component 127, configured to convert skin impedance values acquired from the patient by means of the sensor module SM of the first sensor module preferred embodiment or by means of the sensor module SM of the second sensor module preferred embodiment,
  the ECG/BI electrode interface 132, configured to filter the electric signals acquired from the patient by means of the sensor module SM.

The connection of the contact microphone array 122 and of the voice microphone 123 with the main processor 101 is done through the artificial intelligence processor 124 for the embodiments that include said artificial intelligence processor 124. The reason of connecting the contact microphone array 122 and of the voice microphone 123 with the main processor 101 through the artificial intelligence processor 124 is that said artificial intelligence processor 124 is already configured to be optimized to process "always on" audio signals and to output detected classified commands to the main processor only if predetermined sound conditions are fulfilled, for example if the specific sounds captured from the heart and lungs in case of the contact microphone array 122 are of interest, such as cough or anomalies in the mechanical activity of the heart such as heart murmur.

In the absence of the artificial intelligence processor 124, the connection of the contact microphone array 122 and of the voice microphone 123 with the main processor 101 is done directly.

As shown in FIG. 7C, the main processor 101 communicates with the main unit sensors' components MUSC that enhance the functioning of the invention:
  the wireless communication unit 121, including but not limited to Bluetooth, WIFI communication protocols, near-field communication protocol NFC, mobile network or any combination thereof, the wireless communication unit 121 configured for making available by the processors' sub-unit PSU of the measurements of health parameters to one or more external devices,
  a display interface 119 configured for displaying the measurements of health parameters,
  the buzzer 116, configured to emitting a confirmation or warning sound used for example if the contact with the skin is not appropriate, or the battery is weak, etc.,
  the haptic interface controller 117 configured to emitting a vibration used for example if the contact with the skin is not appropriate, or the battery is weak, etc. The haptic interface controller can function either substituting the buzzer 116 or in conjunction with the buzzer 116,
  a USB interface 129 configured for connecting the main unit MU to an external device,
  a power output interface 128, for powering the selected sensor module SM.

Preferred Embodiments of the Sensor Module SM

Hereafter are disclosed seven preferred embodiments of the sensor module SM.

FIGS. 8A, 8B, 8C and 8D illustrate non-limiting examples of positioning the medical device corresponding, respectively, to the first preferred embodiment of the sensor module— FIG. 8A, the fourth first preferred embodiment of the sensor module— FIG. 8B, the seventh first preferred embodiment of the sensor module— FIG. 8C and the fifth first preferred embodiment of the sensor module— FIG. 8D.

With reference to FIGS. 9A to 9H, the first sensor module preferred embodiment is used for continuous measurements of health parameters related to the activity of the heart and/or lungs over a preset period as prescribed by the health specialist for example two weeks. For this reason, the memory 102 is configured to store the measurements for said preset period and the sensor module SM of the first sensor module preferred embodiment is configured to be worn on the skin of the patient during said preset period, as shown in FIG. 8A. The position of the sensor module of the first sensor module preferred embodiment on the chest of the patient is not limited by the two examples depicted in FIG. 8A.

In the first sensor module preferred embodiment, with reference to FIG. 9A, FIG. 9B, FIG. 9C, FIG. 9D, the sensor module SM further comprises sensor module attaching means, and sensors' components SC.

The sensor module attaching means are configured to accommodate the sensor module array interface SMAI and configured to attach the sensor module SM to the chest of the patient, when the first sensor module preferred embodiment is selected to be mechanically and electrically connected to the main unit MU.

The sensor module attaching means comprise a flexible foil 202. The flexible foil 202 has a flexible foil first side 202-1 and a flexible foil second side 202-2. The sensor module receptacle 201 is fixed on the flexible foil first side 202-1 and the flexible foil second side 202-2 is configured for skin attachment on the chest of the patient, similarly to the attachment of a medical patch.

The sensor module array interface SMAI of the first sensor module preferred embodiment comprises only sensor module fixed-function electrical contacts 204-1.

The sensors' components EC of the sensor module SM comprise a printed electronic assembly electrode 203, arranged on the flexible foil second side 202-2. The printed electronic assembly electrode 203 is configured to acquire electrical signals from the chest of the patient. The electrical signals refer to the functioning of the heart and to the respiration parameters, said respiration parameters reflected by the bio-impedance of the skin. The printed electronic assembly electrode 203 is configured to connect to the sensor module fixed-function electrical contacts 204-1 arranged on the flexible foil first side 202-1.

The printed electronic assembly electrode 203 comprises:
printed electrode pads 203-1, configured to acquire the electrical signals from the skin of the chest of the patient; for example, the printed electrode pads 203-1 are made of silver or mix a silver and carbon,
printed electrical trace 203-2 for connecting the printed electrode pads 203-1 to the sensor module fixed-function electrical contacts 204-1,
printed contacts protection pads 203-4, configured to protect and enhance the electrical contact of the printed electrical trace 203-2 with the main unit fixed-function electrical contacts 104-1; for example, the printed contacts protection pads 203-4 are of carbon.

As seen in FIG. 9H, the main unit fixed-function electrical contacts 104-1 are configured to be connected to the sensor module fixed-function electrical contacts 204-1 and the sensor module fixed-function electrical contacts 204-1 are connected at least to the printed electronic assembly electrode 203, to the sensor module lock-in detection interface 230, and to the sensor module identification interface SM ID 231.

The main unit sensors' components MUSC further comprise at least the following:
the contact microphone array 122,
the voice microphone 123,
the motion sensor 125,
the first electrocardiogram analogue front end ECG AFE component 126,
the bio-impedance component 127,
the ECG/BI electrode interface 132.

For the preferred embodiments when the device further comprises the skin sensors' island area 109, as shown in FIG. 9B and FIG. 9C, the one or more main unit optical sensors 109-1 as well as one or more main unit temperature sensors 109-141 are configured to sense through the one or more light-transfer optical components 109-13. In this case, the sensor module receptacle 201 has a sensor module receptacle opening 201-11 matching the shape of the skin sensors' island area 109 in order to accommodate said skin sensors' island area 109.

Further on, the flexible foil 202 contains a flexible foil opening 202-4 matching the shape of the skin sensors' island area 109, the flexible foil opening 202-4 configured to allow said skin sensors' island area 109 be in physical contact with the patient's skin.

In the cases when the skin sensors' island area 109 include the contact microphone array 122, not represented graphically in FIG. 9B and FIG. 9C, said contact microphone array 122 is configured to auscultate the sounds of the heart or the lungs through said skin sensors' island area 109.

A non-limited list of examples of measurements for which the medical device of this preferred embodiment is configured is the following:
raw electrocardiography ECG and heart rate by the printed electronic assembly electrode 203 jointly with the first electrocardiogram analogue front end ECG AFE component 126, and with the motion sensor component 125 for noise reduction,
respiration rate by the printed electronic assembly electrode 203, jointly with the First Bio-impedance component, and with the motion sensor component 125,
blood pressure by the printed electronic assembly electrode 203 jointly with first electrocardiogram analogue front end ECG AFE component 126, the one or more main unit optical sensors 109-1, and with the motion sensor component 125,
cardiac output and stroke volume by the printed electronic assembly electrode 203 jointly with the first electrocardiogram analogue front end ECG AFE component 126, the one or more main unit photoplethysmography PPG sensor 109-1, and with the bio-impedance component 127,
sounds of the heart or the lungs by the contact microphone array 122 jointly with the printed electronic assembly electrode 203.

The configurations of the flexible foil 202 must respond to numerous challenges among which the following:
the flexible foil 202 must be flexible enough to enable the adapting of the surface of patient's chest, knowing that said surface is not flat,
the flexible foil 202 must be firmly fixed of the surface of patient's chest for the time when the sensor module SM is realizing the measurements together with the main unit MU. The more time it can be firmly fixed, the better, the flexible foil 202 must have certain degree of stiffness in its entirety and especially in its portion where the sensor module fixed-function electrical contacts 204-1 are arranged such that to prevent crumbling of the flexible foil 202 together with the sensor module array interface SMAI.

An example of realization with reference to FIG. 9D discloses the components of the flexible foil 202, starting with the second side of the flexible foil 202-2 which is fixed on patient's chest:

components of the flexible side of the electrode foil 202-2:
- a bottom liner 202-21, protecting the skin adhesive 202-23 when the flexible foil 202 is not in contact with the patient. The bottom liner 202-21 is removed before fixing the flexible foil 202 on patient's chest,
- hydrogel pads 202-22, used to enhance the acquirement of the electrical signals from the chest of the patient,
- the skin adhesive 202-23 for fixing the flexible foil 202 on patient's chest, the skin adhesive 202-23 accommodating printed electrical pads holes 202-231,
- a flexible foil substrate 202-24 for enhancing the adherence of the flexible foil 202 to the particulars of each patient's chest, comprising a flexible electric contact support 202-241 for the sensor module fixed-function electrical contacts 204-1,
- a flexible foil reinforcement membrane 202-25, configured for stiffening the flexible electric contact support 202-241,
- a double side adhesive 202-26, configured for mechanically fixing the receptacle 201 to the flexible foil 202, components of the flexible foil first side 202-1:
- a top liner 202-11, configured for protecting the flexible foil 202 against crumbling before fixing the flexible foil 202 on patient's chest, etc.
- a liner release tab 202-12 configured for easy release of the top liner 202-11, components of the printed electronic assembly electrode 203:
- the printed electrode pads 203-1, configured to acquire the electrical signals from the chest of the patient,
- the printed electrical trace 203-2 for connecting the printed electrode pads 203-1 to the printed contacts protection pads 203-4, configured to protect and enhance the electrical contact with the sensor module array interface SMAI,
- a dielectric encapsulation 203-21 for the printed electrical trace 203-2.

The number of printed electrical pads holes 202-231 matches the number of printed electrical pads 203-1. The number of the printed electrical pads 203-1 as shown in FIG. 9D is not limiting the invention.

The flexible electric contact support 202-241 must be at the same time sufficiently flexible to ensure its folding and sufficiently stiff to avoid crumbling during assembly. Flexibility is ensured by using a flexible material, such as low-density polyethylene, polyethylene terephthalate, polyurethane, polyester, silicone, fabric, nonwoven fabric, paper, or a combination of two or more from the afore-mentioned materials, whereas stiffness is ensured by using the flexible non-stretchable foil reinforcement membrane 202-25.

In case the materials of the flexible foil 202 permit re-use of the flexible foil 202, after having finished the measurements and after having disconnected the sensor module SM from the main unit MU, said flexible foil 202 can be used again.

In case the materials of the flexible foil 202 do not permit re-use of the flexible foil 202, after having finished the measurements and after having disconnected the sensor module SM from the main unit MU, said flexible foil 202 is discarded.

Hereafter are presented three alternative examples of the first sensor module preferred embodiment, with reference to FIG. 9E, FIG. 9F and FIG. 9G. The details of the flexible foil 202 of the three alternative examples of FIG. 9E, FIG. 9F and FIG. 9G are illustrated in FIG. 9D and are disclosed above, making reference to the preferred embodiments that comprise the skin sensors' island area 109. All three alternative examples refer to the sensor module attaching means. The configurations of the electrical coupling of the sensor module array interface SMAI and the configurations of the printed electronic assembly electrode 203 for acquiring the bio-signals are the same for all three alternative examples, whereas the attaching means and the positioning of the various components of the printed electronic assembly electrode 203 are different.

With reference to FIG. 9E, in the first alternative example of the first sensor module preferred embodiment, the sensor module fixed-function electrical contacts 204-1 are arranged on the flexible support 202-241 of the flexible foil second side 202-2, and the sensor module receptacle 201 has the sensor module receptacle opening 201-11.

The flexible electric contact support 202-241 and the sensor module receptacle opening 201-11 are configured to enable the fetching of the sensor module fixed-function electrical contacts 204-1 from the electrode foil second side 202-2 to the electrode foil first side 202-1 by folding said flexible electric contact support 202-241 through said sensor module receptacle opening 201-11 such that said sensor module fixed-function electrical contacts 204-1 be in electrical contact with the main unit fixed-function electrical contacts 104-1.

FIG. 9E schematically shows how the flexible electric contact support 202-241 is configured to be foldable.

In order to assembly the sensor module SM of the first alternative example, the flexible electric contact support 202-241 is firstly passed through the sensor module receptacle opening 201-11, then folded on the sensor module receptacle electric contacts recess area 201-12 until the flexible electric contact support 202-241 covers the entire sensor module receptacle electric contacts recess area 201-12.

With reference to FIG. 9F, in the second alternative example of the first sensor module preferred embodiment, the sensor module fixed-function electrical contacts 204-1 are arranged on the flexible electric contact support 202-241.

The flexible electric contact support 202-241 is arranged to be folded such that to enable fetching of said sensor module fixed-function electrical contacts 204-1 from the flexible foil second side 202-2 to the flexible foil first side 202-1.

The sensor module receptacle 201 has a sensor module receptacle aperture 201-13.

The sensor module receptacle aperture 201-13 is positioned within the sensor module cavity 201-1 matching the size and position of the sensor module fixed-function electrical contacts 204-1 arranged on the flexible electric contact support 202-241.

The flexible electric contact support 202-241 and the sensor module receptacle aperture 201-13 are configured to enable said sensor module fixed-function electrical contacts 204-1 to be in electrical contact with the main unit fixed-function electrical contacts 104-1.

With reference to FIG. 9G, in the third alternative example of the first sensor module preferred embodiment, the flexible foil 202 is configured to accommodate an electric circuit stiffener 202-3 for the sensor module fixed-function electrical contacts 204-1, the electric circuit stiffener 202-3 being mechanically and electrically secured on the flexible foil 202.

The sensor module receptacle 201 has a sensor module receptacle electric contacts aperture 201-13, the sensor module receptacle electric contacts aperture 201-13 accommodating the sensor module fixed-function electrical contacts 204-1 arranged on the electric circuit stiffener 202-3.

The sensor module receptacle electric contacts aperture 201-13 is positioned within the sensor module cavity 201-1, the sensor module receptacle electric contacts aperture 201-13, matching the size and the position of the sensor module fixed-function electrical contacts 204-1. The sensor module receptacle recess area 201-12 is dimensioned and positioned within the receptacle 201 to accommodate the electric circuit stiffener 202-3 and ensure the correct position of the sensor module fixed-function electrical contacts 204-1. The electric circuit stiffener 202-3 is preferably a printed circuit board PCB or a polyethylene terephthalate PET, the electric circuit stiffener 202-3 being provided with two-sides contact vias 202-311.

The electric circuit stiffener 202-3 has two sides: a first electric circuit stiffener side 202-31, the first electric circuit stiffener side 202-31 oriented towards the main unit MU, and a second electric circuit stiffener side 202-32, the second electric circuit stiffener side 202-32 oriented opposite the main unit MU.

The electric circuit stiffener 202-3 is provided with two-sides contact vias 202-311, each of the two-sides contact vias 202-311 having a contact vias' first side and a contact vias' second side, the contact vias' first side and the contact vias' second side not represented graphically. The contact vias' first side is on the same side with the first electric circuit stiffener side 202-31, whereas the contact vias' second side is on the second side with the second electric circuit stiffener side 202-32.

The first electric circuit stiffener side 202-31 is configured to accommodate the sensor module fixed-function electrical contacts 204-1 and the contact vias' first side.

Said contact vias' first side is configured to be in electrical contact with the sensor module fixed-function electrical contacts 204-1.

The second electric circuit stiffener side 202-32 is configured to be secured on the flexible foil first side 202-1 and to accommodate the contact vias' second side, the contact vias' second side being in electrical contact with printed electrical vias 202-5 by means of an electrically-conductive adhesive, The printed electrical vias 202-5 are configured to be electrically connected with the printed electrical trace 203-2.

The choice between the three alternative examples is done depending on the manufacturing possibilities of the flexible foil 202.

The first alternative example is suitable for manufacturing using semi-automatic production lines with low-end robots' assembly machine; it may require more manual process steps and human labor, whereas the second and the third alternative examples are suitable for manufacturing using automatic assembly robotic lines, being cost effective for very high production volumes.

The second sensor module preferred embodiment is used for spot measurements of health parameters related to the activity of the cardiovascular system, that includes the heart's electrical activity, mechanical heart activity, the blood parameters like oxygen saturation, blood pressure, respiratory system, as well as the temperature. The sensor module SM of the second sensor module preferred embodiment acquires on demand spot measurements of the bio-signals from the patient while the medical device carries out spot measurements and stores the measurements in the memory 102. The term "spot" is determined by the customary duration for each measurement according to medical practice, i.e. 30 seconds.

In the second sensor module preferred embodiment, the one or more bio-signals are acquired from the patient from different parts of the body of the patient, such as: the chest, the left knee join, the thumb fingers of the hands, ankle join.

Hereafter are presented two alternative examples of the second sensor module preferred embodiment.

In the first alternative example, with reference to FIGS. 10A to 10H, the sensor module SM further comprises the following sensors' components SC:

- a pair of finger lateral electrodes 205-1, 205-2, arranged on opposite sides on the external surface of the sensor module receptacle 201, such that the pair of finger lateral electrodes 205-1, 205-2 be simultaneously in contact with a thumb finger and an index finger of the same hand of the patient, the pair of finger lateral electrodes 205-1, 205-2 configured to acquire bio-signals from the thumb finger and the index finger, as depicted in FIG. 10A, FIG. 10B, FIG. 10C,
- a pair of bottom electrodes 206-1, 206-2 placed on the external surface of the sensor module receptacle 201, the pair of bottom electrodes 206-1, 206-2 arranged such that to be simultaneously in contact to either the chest or the two thumb fingers for acquiring the corresponding bio-signals, as depicted in FIG. 10A, FIG. 10B, FIG. 10C,
- a multi-function electrode 207 placed on the external surface of the sensor module receptacle 201, configured to acquire bio-signals at least from the thumb or index fingers, the chest, and the knee join of the patient, the multi-function electrode 207 arranged around a sensor module optical area 209, as depicted in FIG. 10B,
- a stethoscope 208, arranged inside the module receptacle 201, the stethoscope 208 comprising a diaphragm 208-1 placed on the external surface of the sensor module receptacle 201, centrally placed between the bottom electrodes 206-1, 206-2, the stethoscope diaphragm 208-1 configured to acquire lung or heart sounds,
- the skin sensor module optical area 209, placed on the external surface of the sensor module receptacle 201, the skin sensor module optical area 209 comprising:
  one or more sensor module optical sensors 209-1,
  one or more forehead temperature sensors 209-2,
- a second electrocardiogram analogue front end ECG AFE component 226, The main unit sensors' components MUSC further comprise at least the following:
  the voice microphone 123,
  the motion sensor 125,
  the first electrocardiogram analogue front end ECG AFE component 126,
  the bio-impedance component 127,
  the ECG/BI electrode interface 132.

The non-limiting example of shape of the sensor module SM as shown in with reference to FIGS. 10A-10G, is optimized to be hand-held and to acquire the bio-signal from irregular surfaces of different parts of the body of the patient mentioned above.

In this non-limiting example, the shape the sensor module SM is an isosceles triangle in cross-section, with rounded angles. The pair of finger lateral electrodes 205-1, 205-2 is placed on the lateral equal sides, whereas the multi-function electrode 207 is placed in any vertex of the triangle opposite to the pair of finger lateral electrodes 205-1, 205-2, in order to ensure a good contact with the fingers that have a round shape, the chest that is plane and with the knee join which is concave.

The multi-function electrode 207 it is designed as a L-shape, having a first side of the L placed on the external surface of the sensor module receptacle 201 in the same axis plane with the pair of finger lateral electrodes 205-1, 205-2, said first side of the L designed as a convex surface to enable its accommodation on surface of the join knee. The second side of the L is provided in the center with a finger recess 209-3, configured to accommodate any finger of the patient. The second side of the L has flat margins, the flat margins placed around the finger recess 209-3 in the same plane with the pair of bottom electrodes 206-1, 206-2 and with the stethoscope diaphragm 208-1.

The finger recess 209-3 is configured to accommodate the skin sensor module optical area 209.

The sensor module of the second sensor module preferred embodiment is further provided with an USB port 211, the USB port 211 configured for connecting the sensor module to a power supply for charging or to another external device, e.g. a personal computer PC, laptop for data downloading or configuration.

The sensor module SM further comprises a sensor module multiplexer switch 210, the sensor module multiplexer switch 210 configured to selectively connect the pair of finger lateral electrodes 205-1, 205-2, the pair of bottom electrodes 206-1, 206-2 and the multi-function electrode 207, to the second electrocardiogram analogue front end ECG AFE component 226 and to the sensor module multi-function contacts 204-2 and to the sensor module fixed-function electrical contacts 204-1 creating one closed loop with the patient body from the list below:
- a first closed loop configured for simultaneously acquiring and pre-processing the bio-signals from the thumb finger and an index finger from of the same hand by the pair of finger lateral electrodes 205-1, 205-2 and the index or the thumb finger from the other hand by the multi-function electrode 207, as shown in FIG. 10E,
- a second closed loop configured for simultaneously acquiring and pre-processing the bio-signals from the chest by the pair of bottom electrodes 206-1, 206-2 and by the multi-function electrode 207, as shown in FIG. 10F,
- a third closed loop configured for simultaneously acquiring and pre-processing the bio-signals from the thumb fingers of both hands by the pair of bottom electrodes 206-1, 206 and the left knee join by the multi-function electrode 207, as shown in FIG. 10G.

The sensor module SM of the second sensor module preferred embodiment comprises both the sensor module fixed-function electrical contacts 204-1 and the module multi-function electrical contacts 204-2, as depicted in FIG. 10H.

The second sensor module preferred embodiment has eight alternative examples of use.

For this purpose, the one or more programmable multiplexer switches 105 are configured for selectively connecting the communication drivers 103 and the enabling components EC to the sensor module multi-function contacts 204-2, the sensor module multi-function contacts 204-2 corresponding to one of the closed loops, and/or to the sensors' components SC, according to the selection of one option from the list below:
  i. the one or more sensor module optical sensors 209-1,
  ii. the one or more forehead temperature sensors 209-2,
  iii. the stethoscope 208,
  iv. the first closed loop,
  v. the second closed loop,
  vi. the third closed loop,
  vii. the first closed loop and the one or more sensor module optical sensors 209-1,
  viii. the second closed loop and the stethoscope 208.

In the first alternative example of use, with reference to FIG. 10E and FIG. 10H, the measurements refer to pulse rate and pulse oximetry, such as arterial oxygen saturation SpO2.

The contact of the sensor module SM with the patient is done by placing the sensor module such that the one or more sensor module optical sensors 209-1 to be in contact with skin of the patient. A non-limiting example of placing of the one or more sensor module optical sensors 209-1 in contact with the skin of the patient is positioning any finger of the patient on the finger recess 209-3.

The one or more programmable multiplexer switches 105 selectively connect the communication drivers 103 and the enabling components EC to the sensor module multi-function contacts 204-2 corresponding to the one or more sensor module optical sensors 209-1.

A non-limiting example of type of sensor module optical sensors 209-1 is the photoplethysmography sensor PPG 209-1. The measurements are carried out by the photoplethysmography sensor PPG 209-1, while the final processing operations are carried out by the main unit MU.

In this case, the pair of finger lateral electrodes 205-1, 205-2, the pair of bottom electrodes 206-1, 206-2, the multi-function sensor module electrode 207 the stethoscope 208, and the one or more forehead temperature sensors 209-2 are deactivated. In the embodiments comprising the main unit with the skin sensors' island area 109, said skin sensors' island area 109 is deactivated.

In the second alternative example of use, with reference to FIG. 10D and FIG. 10H, the measurements refer to the temperature.

The contact of the sensor module SM with the patient is done by placing the sensor module SM such that the one or more forehead temperature sensors 209-2 to be in contact with skin of the patient as depicted FIG. 10D.

The measurements are carried out by the one or more forehead temperature sensors 209-2, while the final processing operations are carried out by the main unit MU.

In this case, the pair of finger lateral electrodes 205-1, 205-2, the pair of bottom electrodes 206-1, 206-2, the multi-function sensor module electrode 207, the stethoscope 208, and the one or more sensor module optical sensors 209-1 are deactivated. In the embodiments comprising the main unit with the skin sensors' island area 109, said skin sensors' island area 109 is deactivated.

In the third alternative example of use, with reference to FIG. 10F and FIG. 10H, the measurements refer to the sounds of the heart and/or lungs by using the stethoscope 208.

The contact of the sensor module SM with the patient is done by placing the sensor module such that to ensure the contact of the stethoscope diaphragm 208-1 on well-defined areas on the chest or the back of the patient as it is presented in FIG. 10F.

The sensor module further comprises the following module enabling components SEC:
- an audio output connector 208-2, configured for connecting an external headset in order to hear in real time stethoscope acquired audio signals,
- a stethoscope contact microphone array 208-3, configured for acquired the heart or lung audio signals from the patient's chest,
- a high throughput wireless communication protocol module 221 configured for transferring uncompressed stethoscope audio data to the external devices like phone, tablet or PC, by wireless communication protocols.
- a power supply 228, mating the power output interface 128 for powering the sensor module SM.

The one or more programmable multiplexer switches 105 selectively connect the communication drivers 103 and the enabling components EC to the sensor module multi-function contacts 204-2 corresponding to the stethoscope 208.

In this alternative example there is a single programmable multiplexer switch 105.

The programmable multiplexer switch 105 uses three main unit multi-function electrical contacts 104-2 and the Inter-IC Sound I2S drivers 103 to connect to a stethoscope Inter-IC Sound I2S interface, the stethoscope Inter-IC Sound I2S interface not represented graphically. Said Inter-IC Sound I2S drivers 103 are configured for audio streaming.

The programmable multiplexer switch 105 uses two main unit multi-function electrical contacts 104-2 and the Inter-Integrated Circuit I2C drivers 103 to connect to a stethoscope Inter-Integrated Circuit I2C interface, the stethoscope Inter-Integrated Circuit I2C interface not represented graphically. Said Inter-Integrated Circuit I2C drivers 103 are configured to command a stethoscope encoder, the stethoscope encoder not represented graphically.

The programmable multiplexer switch 105 uses six main unit multi-function electrical contacts 104-2 and the Secure Digital Input Output SDIO drivers 103 to connect to the high throughput wireless communication protocol module 221 for carrying out audio streaming.

The sensor module lock-in detection interface 230 connect to the lock-in detection interface 130, whereas the sensor module identification interface SM ID 231 connect to the identification interface SM ID 131.

The power supply 228 mates the power output interface 128 for powering the sensor module SM.

The measurements are carried out by the stethoscope 208 while the final processing operations are carried out by the main unit MU, or by the stethoscope 208 jointly with the voice microphone 123 used for noise reduction by noise cancelation techniques.

In this case, the pair of finger lateral electrodes 205-1, 205-2, the pair of bottom electrodes 206-1, 206-2, the multi-function sensor module electrode 207, the one or more sensor module optical sensors 209-1 and the one or more forehead temperature sensors 209-2 are deactivated. In the embodiments comprising the main unit with the skin sensors' island area 109, said skin sensors' island area 109 is deactivated.

In the fourth alternative example of use, with reference to FIG. 10E and FIG. 10H, the measurements refer to the electrocardiogram by activating the first closed loop.

The contact of the sensor module SM with the patient is done by placing the thumb and index fingers from one hand of the patient on the pair of finger lateral electrodes 205-1, 205-2 while the index or thumb finger from the other hand or any other part of the body e.g. wrist on the multi-function electrode 207, acquiring in this way said one or more bio-signals, as depicted FIG. 10E.

The sensor module multiplexer switch 210 selectively connects the pair of finger lateral electrodes 205-1, the multi-function electrode 207 to the sensor module fixed-function electrical contacts 204-1 creating the first closed loop.

The one or more programmable multiplexer switches 105 selectively connect the communication drivers 103 and the enabling components EC to the sensor module multi-function contacts 204-2 corresponding to the first loop.

The measurements are carried out by the first loop jointly with the first electrocardiogram analogue front end ECG AFE component 126, the ECG/BI electrode interface 132 and the motion sensor component 125 for noise reduction. The bio-impedance component 127 can also be used in this fourth alternative example in combination with the aforementioned sensor components for evaluating the level of stress of the patient. The final processing operations are carried out by the main unit MU.

In this case, the pair of bottom electrodes 206-1, 206-2, as well as the stethoscope 208, one or more sensor module optical sensors 209-1, the second electrocardiogram analogue front end ECG AFE component 226, and the one or more forehead temperature sensors 209-2 are deactivated. In the embodiments comprising the main unit with the skin sensors' island area 109, said skin sensors' island area 109 is deactivated.

In the fifth alternative example of use, with reference to FIGS. 10F and 10H, the measurements refer to electrocardiogram, carried out differently from the fourth alternative example, by activating the second closed loop.

The contact of the sensor module SM with the patient is done by placing the sensor module on the chest or the back of the patient, ensuring the contact of the pair of bottom electrodes 206-1, 206-2 and of the second side of the multi-function electrode 207 with the skin, as depicted in FIG. 10F.

The measurements are carried out by the second closed loop jointly with the second electrocardiogram analogue front end ECG AFE component 226, while the final processing operations are carried out by the main unit MU, or by the second closed loop jointly with the second electrocardiogram analogue front end ECG AFE component 226 and with the motion sensor component 125 for noise reduction.

In this case, the pair of finger lateral electrodes 205-1, 205-2, as well as the stethoscope 208, the one or more sensor module optical sensors 209-1, and the one or more forehead temperature sensors 209-2 are deactivated. In the embodiments comprising the main unit with the skin sensors' island area 109, said skin sensors' island area 109 is deactivated.

In the sixth alternative example of use, with reference to FIGS. 10G and 10H, the measurements refer to the electrocardiogram carried out accordingly to Einthoven's triangle method, activating the third closed loop.

The contact of the sensor module SM with the patient is done by placing one thumb finger of one hand on the first bottom electrode 206-1, the other thumb finger of the other hand on the second bottom electrode 206-2 and by placing the first side of the L-shape of the multi-function electrode 207 on the left leg knee join or, alternatively on the left leg ankle, realizing the Einthoven triangle design, as depicted in FIG. 10G.

The measurements are carried out by the third closed loop jointly with the second electrocardiogram analogue front end ECG AFE component 226, while the final processing operations are carried out by the main unit MU, or by the third closed loop jointly with the second electrocardiogram analogue front end ECG AFE component 226 and with the motion sensor component 125 for noise reduction.

In this case, the pair of finger lateral electrodes 205-1, 205-2, as well as the stethoscope 208, the one or more sensor module optical sensors 209-1, and the one or more forehead temperature sensors 209-2 are deactivated. In the embodiments comprising the main unit with the skin sensors' island area 109, said skin sensors' island area 109 is deactivated.

In the seventh alternative example of use, with reference to FIGS. 10E and 10H, the measurements refer to the electrocardiogram activating the first closed loop jointly with the one or more sensor module optical sensors 209-1, as well as pulse rate, the arterial oxygen saturation SpO2, heart rate.

The contact of the sensor module SM with the patient is done by placing the thumb and index fingers from one hand of the patient on the pair of finger lateral electrodes 205-1, 205-2, and simultaneously placing the finger of the other hand on the finger recess 209-3 such that the one or more sensor module optical sensors 209-1 to be in contact with the finger of the other hand, this finger of the other hand being simultaneously in contact with the multi-function electrode 207, as depicted FIG. 10E.

The sensor module multiplexer switch 210 selectively connects the pair of finger lateral electrodes 205-1, the multi-function electrode 207 to the second electrocardiogram analogue front end ECG AFE component 226 creating the first closed loop.

The one or more programmable multiplexer switches 105 selectively connect the communication drivers 103 and the enabling components EC to the sensor module multi-function contacts 204-2 corresponding to the first loop and to the one or more sensor module optical sensors 209-1, the one or more sensor module optical sensors 209-1 jointly with the second electrocardiogram analogue front end ECG AFE component 226.

Two intermediary measurements are carried out simultaneously:
  by the motion sensor component 125 for noise reduction,
  by the one or more sensor module optical sensors 209-1 jointly with the second electrocardiogram analogue front end ECG AFE component 226.

The final processing operations carried out by the main unit MU include synchronization and/or fusing of the above two intermediary measurements.

In this case, the pair of bottom electrodes 206-1, 206-2, as well as the stethoscope 208, and the one or more forehead temperature sensors 209-2 are deactivated. In the embodiments comprising the main unit with the skin sensors' island area 109, said skin sensors' island area 109 is deactivated.

In the eighth alternative example of use, with reference to FIG. 10F and FIG. 10H, the measurements refer to the heart and/or lungs auscultation combined with the electrocardiogram, usually named phonocardiogram PCG, by activating the second closed loop and the stethoscope 208.

The contact of the sensor module SM with the patient is done by placing the sensor module on the chest or the back of the patient, ensuring the contact of the pair of bottom electrodes 206-1, 206-2 and of the second side of the L-shape of the multi-function electrode 207 with the skin, as depicted in FIG. 10F, and, at the same time by placing the stethoscope 208 on the chest and/or back of the patient by means of the stethoscope diaphragm 208-1, as depicted in FIG. 10F.

The measurements are carried out by the second closed loop jointly with the stethoscope 208 and with the second electrocardiogram analogue front end ECG AFE component 226, or by the second closed loop jointly with the stethoscope 208 and with the second electrocardiogram analogue front end ECG AFE component 226 and with the motion sensor component 125 for noise reduction. The final processing operations are carried out by the main unit MU.

In this case, the pair of finger lateral electrodes 205-1, 205-2, as well as one or more sensor module optical sensors 209-1 and the one or more forehead temperature sensors 209-2 are deactivated. In the embodiments comprising the main unit with the skin sensors' island area 109, said skin sensors' island area 109 is deactivated.

In the second alternative example of the second sensor module preferred embodiment, not represented graphically, in order to enhance the quality of bio-signals acquired from the patient and to improve the common mode rejection parameter CMMR, a right-leg-driver RLD function is assigned to one of the pair of bottom electrodes 206-1, 206-2 or to one of the pair of finger lateral electrodes 205-1, 205-2. By assigning the right-leg-driver RLD function, the noise level of the acquired ECG electrical signal is reduced.

The third sensor module preferred embodiment is used for clinical video examination and spot measurements of health parameters related to the general patient health, activity of the cardiovascular system or hemodynamic parameters, that includes the heart's electrical activity, mechanical heart activity, the blood parameters like oxygen saturation, blood pressure, lung auscultation examination and respiratory rate, the temperature, video inspection of the throat and/or ears, video inspection of the skin for dermatological purposes, auscultation of the abdomen. This means that the sensor module SM of the third sensor module preferred embodiment acquires on demand spot measurements of the bio-signals from the patient while the medical device carries out spot measurements, stores the measurements in the memory 102, or send them through a/the wireless connection module 121 to external devices. The term "spot" is determined by the customary duration for each measurement according to medical practice, i.e. 30 seconds.

In the third sensor module preferred embodiment, the one or more bio-signals are acquired from the patient from different parts of the body of the patient, such as: the chest, the left knee join, the thumb fingers of the hands, ankle join, the throat and/or ears, and the abdomen.

Hereafter are presented two alternative examples of the third sensor module preferred embodiment.

In the first alternative example, with reference to FIGS. 11A to 11C, the sensor module SM further comprises the following sensors' components SC:
  a pair of finger lateral electrodes 205-1, 205-2, arranged on opposite sides on the external surface of the sensor module receptacle 201 such that the pair of finger lateral electrodes 205-1, 205-2 be simultaneously in contact with a thumb finger and an index finger of the same hand of the patient, the pair of finger lateral electrodes 205-1, 205-2 configured to acquire bio-signals from the thumb finger and an index finger, as depicted in FIG. 11A, FIG. 11B,
  a multi-function electrode 207 placed on the external surface of the sensor module receptacle 201, configured to acquire bio-signals at least from the thumb or index fingers, and the knee join of the patient, the multifunction electrode 207 arranged around a sensor module optical area 209, as depicted in FIG. 11A, a stethoscope 208, arranged inside the module receptacle 201, the stethoscope 208 comprising a diaphragm 208-1 placed on the external surface of the sensor module receptacle 201, the stethoscope diaphragm 208-1 configured to acquire lung or heart sounds, as depicted in FIG. 11A, FIG. 11B, the skin sensor module optical area 209, placed on the external surface of the sensor module receptacle 201, the skin sensor module optical area 209 comprising:
one or more sensor module optical sensors 209-1,
one or more forehead temperature sensors 209-2, a second electrocardiogram analogue front end ECG AFE component 226, a video camera 236-1, configured to acquire images from the throat and ears and the skin of the patient, the video camera 236-1 comprising:
a detachable tongue depressor assembly 236-11 configured to depress the tongue of the patient,
a detachable otoscope adaptor 236-12, configured to enhance the mechanical positioning of the video camera 236-1 into the ear, an infrared thermal imaging camera 236-2, configured to acquire thermal images from the patient's body.

The video camera 236-1 and the infrared thermal imaging camera 236-2 are placed in a video camera area 236, the video camera area 236 placed on the same side of the sensor module receptacle 201 with the skin sensor module optical area 209. The video camera area 236 accommodates two or more LEDs 236-5 for illuminating the area to be examined.

The sensor module SM further comprises an images signal processor ISP 239, the images signal processor ISP 239 configured to carry out intermediary processing and compression of the images and video stream acquired from the video camera 236-1 and from the infrared thermal imaging camera 236-2.

The main unit sensors' components MUSC further comprises:
the voice microphone 123,
the motion sensor 125,
the first electrocardiogram analogue front end ECG AFE component 126,
the bio-impedance component 127,
the ECG/BI electrode interface 132.

The non-limiting example of shape of the sensor module SM as shown in with reference to FIG. 11A and FIG. 11B, is optimized to be hand-held and to acquire the bio-signal from irregular surfaces of different parts of the body of the patient mentioned above.

In this non-limiting example, the shape of the sensor module receptacle 201 is elongated having the longitudinal axis significantly larger than the cross-section axis. The stethoscope 208 is placed at one end of the longitudinal axis, whereas the multi-function electrode 207 is placed at the other end, creating a vertex of the sensor module receptacle 201 in order to ensure a good contact with the fingers that have a round shape, the chest that is plane, the knee join and the ankle. The pair of finger lateral electrodes 205-1, 205-2 is placed on the lateral equal sides in the proximity of the stethoscope 208.

The multi-function electrode 207 it is designed as a L-shape, having a first side of the L placed in the same axis plane with the pair of finger lateral electrodes 205-1, 205-2, said first side of the L designed as a convex surface to enable its accommodation on surface of the join knee. The second side of the L is provided with a finger recess 209-3, configured to accommodate any finger of the patient. The second side of the L has flat margins, the flat margins placed around the finger recess 209-3.

The finger recess 209-3 is configured to accommodate the skin sensor module optical area 209.

The sensor module of the third sensor module preferred embodiment is further provided with an USB port 211, the USB port 211 configured for connecting the sensor module to a power supply for charging or to another external device e.g. PC, laptop for data downloading or configuration.

The sensor module SM further comprises a sensor module multiplexer switch 210, the sensor module multiplexer switch 210 configured to selectively connect the pair of finger lateral electrodes 205-1, 205-2, and the multi-function electrode 207 and the second electrocardiogram analogue front end ECG AFE component 226 to the sensor module multi-function contacts 204-2 and to the sensor module fixed-function electrical contacts 204-1 creating one closed loop with the patient body from the list below:
a first closed loop configured for simultaneously acquiring and pre-processing the bio-signals from the thumb finger and an index finger from of the same hand by the pair of finger lateral electrodes 205-1, 205-2 and the index or the thumb finger from the other hand by the multi-function electrode 207,
a second closed loop configured for simultaneously acquiring and pre-processing the bio-signals from the thumb fingers of both hands by the pair of finger lateral electrodes 205-1, 205-2 and from the left knee join or the left ankle by the multi-function electrode 207.

The sensor module further comprises the following enabling components SEC:
the audio output connector 208-2, configured for connecting an external headset in order to hear in real time stethoscope acquired audio signals,
the stethoscope contact microphone array 208-3, configured for acquired the heart or lung audio signals from the patient's chest,
the high throughput wireless communication protocol module 221 configured for transferring uncompressed stethoscope audio data to the external devices like phone, tablet or PC, by wireless communication protocols.
the USB port 211 configured for connecting the sensor module to a power supply for charging or to another external device e.g. PC, laptop for data downloading or configuration,
an LCD touch display 237, the LCD touch display 237 configured to display the images acquired by the video camera 236-1 and the infrared thermal imaging camera 236-2 and configured to allow interactions of the patient with the medical device,
a multifunction lateral button 237-1, the multifunction lateral button 237-1 configured to start and stop the measurements and to send commands to the images processor 239, e.g. for displaying the acquired images on the LCD touch display 237,
a GSM eSIM module 238, the GSM eSIM module 238 configured for transferring the uncompressed stethoscope audio data or the video stream to the external devices like phone, tablet or PC, by mobile telecommunication protocols,
the power supply 228, mating the power output interface 128 for powering the sensor module SM.

The sensor module SM of the third sensor module preferred embodiment comprises both the sensor module fixed-function electrical contacts 204-1 and the module multi-function electrical contacts 204-2, as depicted in FIG. 11C.

The third sensor module preferred embodiment has eight alternative examples of use.

For this purpose, the one or more programmable multiplexer switches 105 are configured for selectively connecting the communication drivers 103 and the enabling components EC to the sensor module multi-function contacts 204-2, the sensor module multi-function contacts 204-2 corresponding to one of the closed loops, and/or to the sensors' components SC, according to the selection of one option from the list:

i. the one or more sensor module optical sensors 209-1,
ii. the one or more forehead temperature sensors 209-2,
iii. the stethoscope 208,
iv. the first closed loop,
v. the second closed loop,
vi. the first closed loop and the one or more sensor module optical sensors 209-1,
vii. the video camera 236-1,
viii. the infrared thermal imaging camera 236-2.

The first four alternative examples of use of the third sensor module preferred embodiment are identical with the respective first four alternative examples of use of the second sensor module preferred embodiment.

The sixth alternative example of use of the third sensor module preferred embodiment is identical with the seventh alternative example of use of the second sensor module preferred embodiment.

In the fifth alternative example of use, with reference to FIG. 11C, the measurements refer to the electrocardiogram carried out accordingly to Einthoven's triangle method, activating the second closed loop.

The contact of the sensor module SM with the patient is done by placing one thumb finger of one hand on the first finger lateral electrode 205-1, the other thumb finger of the other hand on the second finger lateral electrode 205-2 and by placing the multi-function electrode 207 on the left leg knee join or, alternatively on the left leg ankle, realizing the Einthoven triangle design, not represented graphically.

The one or more programmable multiplexer switches 105 selectively connect the communication drivers 103 and the enabling components EC to the sensor module multi-function contacts 204-2 corresponding to the second closed loop.

The measurements are carried out by the second closed loop jointly with the second electrocardiogram analogue front end ECG AFE component 226, while the final processing operations are carried out by the main unit MU, or by the second closed loop jointly with the second electrocardiogram analogue front end ECG AFE component 226 and with the motion sensor component 125 for noise reduction.

In this case, the stethoscope 208, one or more sensor module optical sensors 209-1 and the one or more forehead temperature sensors 209-2 are deactivated. In the embodiments comprising the main unit with the skin sensors' island area 109, said skin sensors' island area 109 is deactivated.

In the seventh alternative example of use, the video camera 236-1 is configured to acquire images from the throat and ears of the patient or from the skin.

The one or more programmable multiplexer switches 105 selectively connect the communication drivers 103 and the enabling components EC to the sensor module multi-function contacts 204-2 corresponding to the video camera 236-1.

The tongue depressor assembly 236-11 has an L-shape, having on one side a tongue fixing frame 236-111 and, on the other side, a tongue depressor 236-112.

In case examination of the throat is required, the tongue fixing frame 236-111 is attached to the video camera area 236 by means of a video camera area spring-loaded detent mechanism 236-4, said video camera area spring-loaded detent mechanism 236-4 matching video camera area guiding recesses 236-3, the video camera area guiding recesses 236-3 placed on the edges of the video camera area 236.

The tongue depressor 236-112 is used to hold still the tongue of the patient while the video camera 236-1 acquires images.

The otoscope adaptor 236-12 comprises an otoscope fixing frame 236-121 and an otoscope 236-122, the otoscope 236-122 prolonging the otoscope fixing frame 236-121.

In case examination of the ears is required, otoscope fixing frame 236-121 is attached to the video camera area 236 by means of the video camera area spring-loaded detent mechanism 236-4.

The images acquired by the video camera 236-1 undergo intermediary processing and compression of the images and video stream, the intermediary processing results being then sent to the main unit MU for final processing.

In this case, the stethoscope 208, the pair of finger lateral electrodes 205-1, 205-2, the multi-function electrode 207, one or more sensor module optical sensors 209-1 and the one or more forehead temperature sensors 209-2 are deactivated. In the embodiments comprising the main unit with the skin sensors' island area 109, said skin sensors' island area 109 is deactivated.

In the eighth alternative example of use, the infrared thermal imaging camera 236-2, configured to acquire images from the inside of the patient's body, such as for example examination of the breasts for detecting breast cancer.

The one or more programmable multiplexer switches 105 selectively connect the communication drivers 103 and the enabling components EC to the sensor module multi-function contacts 204-2 corresponding to the infrared thermal imaging camera 236-2.

The examination of the patient is done by placing the sensor module SM such that the infrared thermal imaging camera 236-2 face the skin of the patient corresponding to the area from the inside of the patient's body that requires examination. It is not necessary to be in direct contact with the skin.

The images acquired by the infrared thermal imaging camera 236-2 undergo intermediary processing and compression of the images and video stream, the intermediary processing results being then sent to the main unit MU for final processing.

In this case, the stethoscope 208, the pair of finger lateral electrodes 205-1, 205-2, the multi-function electrode 207, the one or more sensor module optical sensors 209-1 and the one or more forehead temperature sensors 209-2 are deactivated. In the embodiments comprising the main unit with the skin sensors' island area 109, said skin sensors' island area 109 is deactivated.

In the second alternative example of the second sensor module preferred embodiment, not represented graphically, in order to enhance the quality of bio-signals acquired from the patient and to improve the common mode rejection parameter CMMR, a right-leg-driver RLD function is assigned to the pair of finger lateral electrodes 205-1, 205-2. By assigning the right-leg-driver RLD function, the noise level of the acquired ECG electrical signal is reduced.

The fourth sensor module preferred embodiment is used for continuous monitoring of patient electrocardiogram ECG, usually for periods up to 24-48 h, the one or more bio-signals being acquired from the chest of the patient. The fourth sensor module preferred embodiment has the advantage of obtaining supplementary heart activity vector leads e.g., from 2 to 12 for more accurate heart disease diagnostic because the bio-signals are acquired from more places from the chest, and the advantage of analyzing data in real time.

Yet another advantage is that the sensor module of the fourth sensor module preferred embodiment can be used by the patient for detailed, second-line measurements after first-line measurements carried out with the sensor module of the first or second sensor module preferred embodiment, said measurements carried out with the sensor module of the first or second sensor module preferred embodiment having spotted a problem which requires the second-line measurements.

With reference to FIG. 8B, FIG. 12A and FIG. 12B, the sensor module SM of the fourth sensor module preferred embodiment further comprises the following sensors' components SC:
- one or more second electrocardiogram analogue front end ECG AFE components 226.
- one or more filter protection circuits 241, each filter protection circuit 241 connected, respectively, to one second electrocardiogram analogue front end ECG AFE component 226, the one or two second electrocardiogram analogue front end ECG AFE components 226, and the corresponding one or more filter protection circuits 241 being arranged inside the sensor module receptacle 201,
- an electrode analogic wire assembly 242 attachable to the sensor module receptacle 201 by means of a lead connector 242-3.

The lead connector 242-3 is configured to be electrically connected to the one or two electrocardiogram analogue front end ECG AFE components 226 by means of the respective one or two filter protection circuits 241.

The electrode analogic assembly 242 comprises:
- a plurality of electrodes 242-2, at least two, preferable five for each electrocardiogram analogue front end ECG AFE component 226, the plurality of electrodes 242-2 configured to acquire the electrical signals from the chest of the patient;
- the plurality of electrodes 242-2 configured to be electrically connected through the lead connector 242-3 to the filter protection circuits 241 by means of a plurality of electrode wires 242-1, each electrode wire 242-1 corresponding to one electrode 242-2 from the plurality of electrodes 242-2. The connection to the filter protection circuits 241 is carried out by inserting the lead connector 242-3 in the USB port 211.

FIG. 12A shows a non-limiting example of realization with one electrocardiogram analogue front end ECG AFE component 226 having five of electrodes 242-2, whereas FIG. 12B shows another non-limiting example of realization with two electrocardiogram analogue front end ECG AFE components 226, the number of electrodes 242-2 of each of the two electrocardiogram analogue front end ECG AFE component 226 being at least two, preferably five.

The main unit sensors' components MUSC further comprise at least the following:
- the voice microphone 123,
- the motion sensor 125,
- the first electrocardiogram analogue front end ECG AFE component 126,
- the bio-impedance component 127,
- the ECG/BI electrode interface 132.

The fourth sensor module preferred embodiment has at least the following sensor module enabling components SEC:
- the USB port 211,
- sensor module lock-in detection interface 230,
- sensor module identification interface SM ID 231.

The one or more programmable multiplexer switches 105 are configured to selectively connect the communication drivers 103 and the enabling components EC to the sensor module multi-function contacts 204-2 corresponding to the to the one or two second electrocardiogram analogue front end ECG AFE components 226 for carrying out the ECG measurements.

The plurality of electrodes 242-2 are placed on patient body on specific well-known places for acquiring different heart electric vectors, alternatively named leads in the state of art.

The sensor module SM of the fourth sensor module preferred embodiment uses either one electrocardiogram analogue front end ECG AFE component 226 or two second electrocardiogram analogue front end ECG AFE components 226, the latter example of realization being depicted in FIG. 12B. When using two second electrocardiogram analogue front end ECG AFE components 226, the accuracy of the measurements is improved.

For each electrocardiogram analogue front end ECG AFE component 226 it is used a filter protection circuit 241 and two to five, preferably five electrodes 242-2.

The sensor module of the fourth sensor module preferred embodiment is further provided with an USB port 211, the USB port 211 configured for connecting the sensor module to a power supply for charging, connecting to another external device e.g. PC, laptop for data downloading or configuration or to connect the lead connector 242-3 to the filter and protection circuit 241.

The sensor module of the fourth sensor module preferred embodiment is further provided with a body fixing clip 245, for attaching to patient's clothes. The body fixing clip 245 is a non-limiting example of sensor module attaching means.

The sensor module SM of the fourth sensor module preferred embodiment comprises both the sensor module fixed-function electrical contacts 204-1, and sensor module multi-function contacts 204-2, as depicted in FIG. 12B.

The fifth sensor module preferred embodiment is used for real-time, short-term measurements of health parameters related to the activity of the heart and/or lungs over a predetermined period of time.

The sensor module SM of the preferred embodiment has the advantage that the patient can carry it during his daily sport activities or rehabilitation exercises without being disturbed by the medical device, as shown in FIG. 8D.

With reference to FIG. 13A, FIG. 13B and FIG. 13C, the sensor module SM of the fifth sensor module preferred embodiment further comprises sensors' components SC and sensor module attaching means.

The sensors' components SC include a dry electrodes assembly 232 comprising dry electrodes 232-1, the dry electrodes 232-1 configured to acquire bio-signals from the chest of the patient, and an electrical trace 232-2, the electrical trace 232-2 configured to connect the dry electrodes 232-1 with the sensor module fixed-function electrical contacts 204-1, The dry electrodes 232-1 can be made of optimized polymer conductive materials.

The use of the dry electrodes 232-1 is advantageous for the fifth sensor module preferred embodiment because it allows using the medical device having the selected the sensor module of the fifth sensor module preferred embodiment for medium up to moderate intensity activities during exercises without impairing the ECG signal quality due to the abundance sweat of the patient's body.

The sensor module attaching means include:
a textile elastic strap 240, having:
   a textile elastic strap first side 240-1 comprising means for attaching the sensor module receptacle 201,
   a textile elastic strap second side 240-2 configured for accommodating the dry electrodes assembly 232,
a flexible patient protection foil comprising:
   a flexible patient protection foil first side 233-1, the flexible patient protection foil first side 233-1 arranged on the electrical trace 232-2, the flexible patient protection foil 233,
   a flexible patient protection foil second side 233-2, the flexible patient protection foil second side 233-2 accommodating a flexible electric contact support, not shown graphically.

The sensor module fixed-function electrical contacts 204-1 are arranged on the flexible electric contact support, said sensor module fixed-function electrical contacts 204-1 not being visible in FIG. 13A and FIG. 13B.

The sensor module receptacle 201 comprises a sensor module receptacle opening 201-11.

The sensor module receptacle opening 201-11 is configured to enable the fetching of the sensor module fixed-function electrical contacts 204-1 from the flexible patient protection foil second side 233-2 to the flexible patient protection foil first side 233-1 by folding said flexible electric contact support 202-241 through said sensor module receptacle opening 201-11 such that said sensor module fixed-function electrical contacts 204-1 be in electrical contact with main unit fixed-function electrical contacts 104-1.

The main unit sensors' components MUSC further comprises:
the contact microphone array 122,
the voice microphone 123,
the motion sensor 125,
the first electrocardiogram analogue front end ECG AFE component 126,
the bio-impedance component 127,
the ECG/BI electrode interface 132.

The main unit MU comprises a skin sensors' island area 109, the skin sensors' island area 109 is configured to sense through the one or more light-transfer optical components 109-13.

The shape of the sensor module receptacle opening 201-11 matches the shape of the skin sensors' island area 109 in order to accommodate said skin sensors' island area 109.

The flexible patient protection foil 233 contains a flexible foil opening, not represented graphically in FIG. 13A and FIG. 13B, the flexible foil opening matching the shape of the skin sensors' island area 109, and the flexible foil opening configured to allow said skin sensors' island area 109 be in physical contact with the patient's skin.

The skin sensors' island area 109 comprises one or more main unit optical sensors 109-1, each of the one or more optical sensors 109-1 comprising:
   one or more light sources arranged to emit light through one or more light-transfer optical components 109-13,
   one or more light-detectors, arranged to detect light through the one or more light-transfer optical components 109-13,
   one or more skin sensors' island sub-areas, comprising one or more main unit temperature sensors 109-141 configured to sense through the one or more light-transfer optical components 109-13.

Each light-detector is spatially separated by each light source by a light separation distance dn, and each light-detector together with each light source are configured to generate a light path.

The light separation distance dn is comprised between a pre-determined minimum light separation distance MIN-dn and a pre-determined maximum light separation distance MAX-dn, the pre-determined minimum light separation distance MIN-dn and the pre-determined maximum light separation distance MAX-dn being configured for chest measurements.

The skin sensors' island area 109 further includes the contact microphone array 122, not represented graphically in FIG. 13A and FIG. 13B, said contact microphone array 122 configured to auscultate the sounds of the heart or the lungs through said skin sensors' island area 109.

When the main unit fixed-function electrical contacts 104-1 are connected to the sensor module fixed-function electrical contacts 204-1, the dry electrodes assembly 232 is configured to acquire and pre-process the bio-signals from the chest of the patient, and the skin sensors' island area 109 is configured to acquire the bio-signals from the chest of the patient.

A non-limited list of examples of measurements for which the medical device of this preferred embodiment is configured is the following:
   raw electrocardiography ECG and heart rate by the dry electrodes assembly 232 jointly with the first electrocardiogram analogue front end ECG AFE component 126, and with the motion sensor component 125 for noise reduction,
   respiration rate by the dry electrodes assembly 232, jointly with the First Bio-impedance component, and with the motion sensor component 125,
   blood pressure by the dry electrodes assembly 232 jointly with first electrocardiogram analogue front end ECG AFE component 126, the one or more main unit optical sensors 109-1, and with the motion sensor component 125,
   cardiac output and stroke volume by the dry electrodes assembly 232 jointly with the first electrocardiogram analogue front end ECG AFE component 126, the one or more main unit photoplethysmography PPG sensor 109-1, and with the bio-impedance component 127,
   sounds of the heart or the lungs by the contact microphone array 122 jointly with by the dry electrodes assembly 232.

The sixth sensor module preferred embodiment is used for real-time, short-term measurements of health parameters such as electrocardiogram ECG, heart rate, blood pressure, pulse rate and pulse oximetry, such as arterial oxygen saturation SpO2, all the afore-mentioned related to the activity of the heart over a predetermined period of time as well as temperature, stress level, or the number of steps, etc.

The sixth sensor module preferred embodiment is used for the cases when it is not required a very detailed level of measurements or high measurements frequency rate such as in the fourth sensor module preferred embodiment, being appropriate when the patient is in good health, offering highest wearing comfort level.

The sensor module SM of the preferred embodiment has the advantage that the patient can carry it during his daily routine activities, without being disturbed by the medical device which is attached on the wrist, as shown in FIG. 14C.

The main unit sensors' components MUSC further comprises:
- the voice microphone 123,
- the motion sensor 125,
- the first electrocardiogram analogue front end ECG AFE component 126,
- the bio-impedance component 127,
- the ECG/BI electrode interface 132.

The main unit MU further comprises the skin sensors' island area 109, the skin sensors' island area 109 configured to sense through the one or more light-transfer optical components 109-13.

The skin sensors' island area 109 comprises one or more main unit optical sensors 109-1, each of the one or more optical sensors 109-1 comprising:
- one or more light sources arranged to emit light through one or more light-transfer optical components 109-13,
- one or more light-detectors, arranged to detect light through the one or more light-transfer optical components 109-13,
- one or more skin sensors' island sub-areas, comprising one or more main unit temperature sensors 109-141 configured to sense through the one or more light-transfer optical components 109-13.

Each light-detector is spatially separated by each light source by a light separation distance dn, and each light-detector together with each light source are configured to generate a light path.

The light separation distance dn is comprised between a pre-determined minimum light separation distance MIN-dn and a pre-determined maximum light separation distance MAX-dn, the pre-determined minimum light separation distance MIN-dn and the pre-determined maximum light separation distance MAX-dn being configured for wrist measurements.

The sensor module receptacle 201 has a sensor module receptacle opening 201-11 matching the shape of the skin sensors' island area 109 in order to accommodate said skin sensors' island area 109.

With reference to FIG. 14A, FIG. 14B and FIG. 14C, and FIG. 14D, the sensor module SM further comprises sensors' components SC and sensor module attaching means.

The sensors' components SC include:
- a pair of finger lateral electrodes 205-1, 205-2, arranged on opposite sides on the external surface of the sensor module receptacle 201 such that the pair of finger lateral electrodes 205-1, 205-2 be simultaneously in contact with a thumb finger and an index finger of the same hand of the patient, the pair of finger lateral electrodes 205-1, 205-2 configured to acquire bio-signals from the thumb finger and an index finger,
- a wrist bottom electrode 206-3 placed on the external surface of the sensor module receptacle 201, configured to acquire bio-signals from the wrist of the second hand of the patient, the wrist bottom electrode 206-3 arranged around the skin sensors' island area 109.

The sensor module attaching means includes a wrist silicone strap 260 comprising means for attaching the sensor module receptacle 201.

The wrist silicone strap 260 has the shape of a bracelet that is attached to the wrist of the patient.

The main unit fixed-function electrical contacts 104-1 are connected to the sensor module fixed-function electrical contacts 204-1, the pair of finger lateral electrodes 205-1, 205-2 and the wrist bottom electrode 206-3 are configured to create a closed loop configured for simultaneously acquiring and pre-processing the bio-signals from the thumb finger and an index finger from of the same hand by the pair of finger lateral electrodes 205-1, 205-2 and from the wrist by the wrist bottom electrode 206-3 of the second hand.

The skin sensors' island area 109 is configured to acquire the bio-signals from the wrist.

A non-limited list of examples of measurements for which the medical device of this preferred embodiment is configured is the following:
- raw electrocardiography ECG and heart rate by the pair of finger lateral electrodes 205-1, 205-2 and the wrist bottom electrode 206-3 configured to acquire bio-signals from the wrist of the patient, jointly with the first electrocardiogram analogue front end ECG AFE component 126, and with the motion sensor component 125,
- blood pressure by the wrist bottom electrode 206-3 jointly with first electrocardiogram analogue front end ECG AFE component 126, the one or more main unit optical sensors 109-1, and with the motion sensor component 125,
- temperature by the one or more main unit temperature sensors 109-141,
- stress level by the first electrocardiogram analogue front end ECG AFE component 126, jointly with the ECG/BI electrode interface 132 and the motion sensor component 125.

The seventh sensor module preferred embodiment is used for real-time, short-term measurements of health parameters such as pulse rate, pulse oximetry, such as arterial oxygen saturation SpO2, temperature. One of the most frequently optical sensors 109-1 is the photoplethysmography PPG sensor 109-1.

The seventh sensor module preferred embodiment is used for the cases when it is not possible to use neither the sensor module of the sixth sensor module preferred embodiment nor the sensor module of the fifth sensor module preferred embodiment for causes being related to either patient body mass index or if patient has inserted medical catheter cannula.

The sensor module SM of the seventh sensor module preferred embodiment has the advantage that the patient can carry it during his daily home activities without being disturbed by the medical device which is attached to the arm, as shown in FIG. 8C.

With reference to FIG. 15A, FIG. 15B and FIG. 15C, the sensor module SM further comprises sensor module attaching means. Sensor module attaching means that include a textile elastic strap 270 comprising means for attaching the sensor module receptacle 201.

The textile elastic strap 270 has the shape of an arm band attached to the arm of the patient.

The main unit sensors' components MUSC further comprises:
- the motion sensor 125.

The main unit MU further comprises a skin sensors' island area 109, the skin sensors' island area 109 is configured to sense through the one or more light-transfer optical components 109-13.

The skin sensors' island area 109 comprises one or more main unit optical sensors 109-1, each of the one or more optical sensors 109-1 comprising:
- one or more light sources arranged to emit light through one or more light-transfer optical components 109-13, one or more light-detectors, arranged to detect light through the one or more light-transfer optical components 109-13, one or more skin sensors' island sub-areas, comprising one or more main unit temperature sensors 109-141 configured to sense through the one or more light-transfer optical components 109-13.

Each light-detector is spatially separated by each light source by a light separation distance dn, and each light-detector together with each light source are configured to generate a light path.

The light separation distance dn is comprised between a pre-determined minimum light separation distance MIN-dn and a pre-determined maximum light separation distance MAX-dn, the pre-determined minimum light separation distance MIN-dn and the pre-determined maximum light separation distance MAX-dn being configured for arm measurements.

The sensor module receptacle 201 has a sensor module receptacle opening 201-11 matching the shape of the skin sensors' island area 109 in order to accommodate said skin sensors' island area 109.

The main unit fixed-function electrical contacts 104-1 are connected to the sensor module fixed-function electrical contacts 204-1, the skin sensors' island area 109 is configured to acquire the bio-signals from the arm.

A non-limited list of examples of measurements for which the medical device of this preferred embodiment is configured is the following:

Temperature by the one or more main unit temperature sensors 109-141,

Pulse rate and/or pulse oximetry by the one or more main unit optical sensors 109-1, and with the motion sensor component 125.

The medical device of the invention is configured to be connectable to various types of external devices.

FIG. 16 shows an example of external device 255 that is connected to the USB port 211 by means of a USB cable 255-1. The external device 255 is configured to carry out one or more of the following tasks:

charging the medical device by further connecting the medical device to a power supply through the USB cable 255-1, exchanging data between the memory 102 and one or more external memories, connecting the processor's sub-unit PSU to an external device processor for controlling the step 5 of the method.

FIG. 17 shows another example of external device: a multiple charger device 256 configured for simultaneously accommodating one or more medical devices of the invention, or one or more main units MU or one or more sensor modules SMs, hereafter called accommodated devices. The multiple charger device 256 is configured to carry out one or more of the following tasks:

charging the medical devices by further connecting the medical device to a power supply through the USB cable 255-1, exchanging data between the memories 102 of either medical device and one or more external memories, connecting the processor's sub-unit PSU of either medical device to the external device processor for controlling the step 5 of the method, provide ultraviolet light for disinfection of the medical devices while the medical devices are charging.

FIG. 17 depicts the multiple charger device 256 configured for charging six medical devices of the invention, the number not being limited. The multiple charger device 256 is used, for example, in the medical facilities before giving each medical device to the patients, or after having received the medical devices from the patients.

FIG. 17 shows three main units MU accommodated and a sensor module SM of the second sensor module preferred embodiment, the sensor module cavity 201-1 of the sensor module SM of the second sensor module preferred embodiment being visible in the figure.

The multiple charger device 256 is provided with a number of UV LEDs 256-1, one UV LEDs 256-1 for disinfection of the respective accommodated device.

The multiple charger device 256 is provided with one or more multiple charger device displays 256-2 for displaying the charge status of battery for each of the accommodated devices and disinfection status of each of the accommodated devices.

Finally, as shown in FIG. 17, it is possible to combine the multiple charger device 256 and the external device 255, by plugging the external device 255 to a multiple charger device USB port 256-3.

Second Aspect of the Invention

With reference to FIG. 18, in a second aspect of the invention it is provided a computer-implemented method of monitoring health parameters of a patient using the medical device according to any of the embodiments described above. The method has ten steps.

In the first step, the main unit MU is electrically and mechanically connected to the selected sensor module SM. The selection of the sensor module SM is carried out among the plurality of sensor modules SM described above for carrying out the measurements of health parameters that are specifically required for each patient.

For patient safety reason, all main unit fixed-function electrical contacts 104-1 and main unit multi-function electrical contacts 104-2 having output capabilities, drive current or voltage are switched off until the main unit MU is mechanically and electrically connected to the sensor module SM.

If the attached sensor SM requires power supply, the processors' sub-unit PSU enables the power output interface 128 to power the selected sensor module SM by connecting the main unit fixed-function electrical contact 104-1 corresponding to the power output interface 128.

In the second step, when the sensor module SM is electrically and mechanically connected to the main unit MU, the lock-in detection interface 130 together with the sensor module lock-in detection interface 230 detect that the electrical and mechanical connection of the sensor module SM to the main unit MU has been established.

Then, in the third step, the identification interface SM ID 131 together with the sensor module identification interface SM ID 231 detect which sensor module SM is electrically and mechanically connected to the main unit MU and recognize the associated sensor module tasks.

In the fourth step the processors' sub-unit PSU selects one or more specific sensor module tasks from the sensor module tasks corresponding to the required measurements of health parameters. Usually said sensor module tasks are included in a sensor module tasks list.

In the fifth step, the configuration for the sensor module SM is loaded by the processors' sub-unit PSU, corresponding to the one or more specific sensor module tasks, either from the memory 102 or, for the embodiments where the main unit includes the wireless connection module 121, received by said wireless connection module 121, for example, from the specific external device.

In the sixth step, simultaneously, at the instructions received from the processors' sub-unit PSU, corresponding to the one or more selected specific sensor module tasks two operations are carried out:

The main unit sensors' components MUSC and the enabling components EC are electrically connected to the sensor module fixed-function electrical contacts 204-1, for the one or more selected specific sensor module tasks, according to the configuration.

The communication drivers 103 and the enabling components EC are electrically connected to the sensor module multi-function contacts 204-2 or to the sensor module fixed-function electrical contacts 204-1, or to the sensor module multi-function contacts 204-2 and the sensor module fixed-function electrical contacts 204-1, according to the configuration.

In the seventh step, the medical device acquires the one or more bio-signals from an anatomic part of the patient corresponding to the required measurements of health parameters.

In the majority of cases, the medical device is placed in contact with the skin of the patient in selected anatomic area or areas, depending on the type of measurements. The sensor module preferred embodiments disclosed ways of placing the medical device in contact with the patient.

In other cases, the medical device is placed in the proximity of the patient, such that the patient be in within the range of measurement of said one or more bio-signals by the medical device.

In the eighth step, the one or more bio-signals are processed by the medical device.

According to the second principle, the intermediary processing operations are distributed among the sensor module SM and the main unit MU.

Depending on the embodiment of the sensor module SM, as well as depending on the type of required measurements of health parameters to be carried out, the distribution of the intermediary processing operations among the sensor module SM and the main unit MU is also different: in some examples, the sensor module SM carries out more intermediary processing, whereas in other examples the sensor module SM carries out less intermediary processing operations. In all cases, the final processing operations are carried out by the main unit MU.

The measurements of health parameters are outputted by the main processor 101 of the processors' sub-unit PSU.

The measurements of health parameters are displayed by using the display interface 119.

In the nineth step of the method, the measurements of health parameters are stored in a memory 102 as a patient data file and are made available by the processors' sub-unit PSU of the measurements of health parameters to one or more external devices in order to be used for monitoring the health parameters of the patient.

The measured parameters are available either for displaying locally on display, the display not represented graphically, by means of the display interface 119 LED or for displaying on said external devices, the external devices connected to the medical device by means of the wireless connection, or for displaying both locally and on the external devices.

In the tenth step of the method, once the measurements are finished, the main unit MU is electrically disconnected from the sensor module SM by sending instructions to the detection pair of corresponding electrical contacts to disconnect the main unit lock-in detection fixed-function electrical contact 104-1 from the corresponding module lock-in detection fixed-function electrical contact 204-1.

The mechanical disconnection is carried out by the patient.

The electrical disconnection of the main unit MU is important for patient safety reasons because it affects all the main unit electrical contacts that were used during the measurements, both the main unit fixed-function electrical contacts 104-1 and the main unit multi-function electrical contacts 104-2 After the mechanical disconnection, there is no risk of injecting the patient voltages outside the medical standards limits.

The post-processing of the measurement of said health parameters, as well as the methods for making available the measurements in order to be used for the monitoring of the health parameters are outside the scope of this invention.

Another set of steps of the method can begin using another selected sensor module SM.

The method according to the invention as disclosed above has the advantage that it enables the measurement of said health parameters either as spot measurements, continuously, or as repetitive measurements over a period of time.

In a preferred embodiment of the method, the method comprises a further step in which the processor's sub-unit PSU is connected via wireless telecommunication to the external device processor, said further step taking place before starting the method and in which a part of the instructions stored in the memory 102 are replaced by external instructions controlling the 6th step of the method of said preferred embodiment. This responds to the situations in which the measurements take place in an examination of the patient by the health specialist via telemedicine said health specialist's using said external device processor during the telemedicine consultation to carry out the measurements. For example: measurements of the electrical heart activity with an electrocardiograph ECG remotely controlled by the external device processor during the consultation.

The method according to the invention as disclosed above has the advantage that it enables carrying out of the measurements by the patient himself or it allows the medical specialist to carry out them during the telemedicine consultation.

In the preferred embodiment when the processors' sub-unit PSU further comprises the artificial intelligence processor, the method of the invention comprises further steps:
    processing the measurements of health parameters received from one or more of the following:
        the main processor 101,
        from one or more external sensors, by running artificial intelligence models on edge and classifying the measurements of health parameters according to health criteria,
    sending classified measurements of health parameters to the main processor 101,
    making available by the processors' sub-unit PSU of the classified measurements of health parameters to the one or more external devices.

In another preferred embodiment, when the medical device further comprises means for identifying the patient including at least a fingerprint biometric area 111 and one or more biometric sensors 112 included in the processors' sub-unit PSU, the method of the invention comprises one further sub-step in step 5 before the loading of the configuration for the selected sensor module SM by the processors' sub-unit PSU:

patient authentication by means of the fingerprint biometric area 111 and the one or more biometric sensors 112 and loading a corresponding patient configuration.

The corresponding patient configuration refers to specific details for each patient, such as, for example, the sensor modules SM that were used in the past.

The corresponding patient configuration is loaded by the processors' sub-unit PSU, either from the memory 102 or, for the embodiments where the main unit includes the wireless connection module 121, received by said wireless connection module 121, for example, from the specific external device.

For this purpose, the method of the invention comprises one further sub-step after or during carrying out step 1 of the method:

placing the finger of the patient on the fingerprint biometric area 111.

Third Aspect of the Invention

In a third aspect of the invention it is presented a non-transitory computer-readable storage medium encoded with a computer program, the computer program comprising instructions executable by the medical device for monitoring health parameters of a patient of any preferred embodiment, which, upon such execution by the medical device, causes the medical device to perform operations of the method for monitoring health parameters of the patient of any preferred embodiment.

In a preferred embodiment, the computer program comprises instructions to perform operations of the method for monitoring at least the following health parameters of the patient: a blood pressure, a blood oxygenation rate, a heart rate, a body temperature, an electrocardiogram wave form representing the electrical heart activity, sounds of the heart, sounds of the lungs, sounds of the abdomen, images from the throat, images from the ears, images from the skin, thermal images from the patient's body, as well as combinations thereof.

While certain embodiments of the present invention have been described in detail, those skilled in the art will recognize various alternative embodiments for practicing the invention as defined by the following claims.

Reference Signs

MU main unit
PSU processors' sub-unit
   101 main processor
   102 memory
   103 communication drivers
MUAI main unit array interface
   104-1 main unit fixed-function electrical contacts
   104-2 main unit multi-function electrical contacts
105 one or more programmable multiplexer switches
106 one or more simple switches
MMM main unit mechanical means
   107 a guiding element
      108-1 spring-loaded detent
109 skin sensors' island area
   109-1 one or more main unit optical sensors
      one or more light sources: 8 light emitting diodes LEDs from 109-111 to 109-118
      one or more light-detectors: 3 photodiodes from 109-121 to 109-123
      109-13 one or more light-transfer optical components
      109-141 one or more main unit temperature sensors from the one or more skin sensors' island sub-areas
d1, d2, d3, . . . dn light separation distance
110 battery
111 a fingerprint biometric area
112—one or more biometric sensors
113 top cover
   113-1 button hole
   113-2 on-off button
114 bottom cover
   114-1 outer gasket
   114-2 inner gasket
115 main PCB
MUSC main unit sensors' components
   109-1 one or more main unit optical sensors
      109-141 one or more main unit temperature sensors
122 contact microphone array
123 voice microphone
125 motion sensor
126 first electrocardiogram analogue front end ECG AFE component
127 bio-impedance component
132 ECG/BI electrode interface
EC enabling components
116 buzzer
117 haptic interface controller
119 display interface
120 power management unit
121 wireless connection module
124 artificial intelligence processor
128 power output interface
129 USB interface
130 lock-in detection interface
131 identification SM ID interface
SM sensor module
SMAI sensor module array interface for all preferred embodiments
   204-1 sensor module fixed-function electrical contacts
   204-2 module multi-function electrical contacts
SMM sensor module mechanical means for all preferred embodiments
201 sensor module receptacle
   201-1 a sensor module cavity
   201-2 a guiding recess
   201-3 sensor module detent recesses
SC sensors' components—see each preferred embodiment
SEC Sensor module enabling components—see each preferred embodiment.
First sensor module preferred embodiment SM1
SC sensors' components for the first sensor module preferred embodiment
   201-11 sensor module receptacle opening
   201-12 sensor module receptacle electric contacts recess area
   201-13 sensor module receptacle electric contacts aperture
202 flexible foil
   202-1 flexible foil first side
      202-11 top liner
      202-12 liner release tab
   202-2 flexible foil second side
      202-21 bottom liner
      202-22 hydrogel pads
      202-23 skin adhesive
         202-231 printed electrical pads holes 202-24 flexible foil substrate
  202-241 flexible electric contact support
  202-25 flexible foil reinforcement membrane
  202-26 double side adhesive liner
202-3 electric circuit stiffener
  202-31 top electric circuit stiffener side
    202-311 electric circuit stiffener vias
  202-32 bottom electric circuit stiffener side
202-4 flexible foil opening
202-5 flexible foil printed electrical vias
203 printed electronic assembly electrode
  203-1 printed electrode pads
  203-2 printed electrical trace
    203-21 dielectric encapsulation
  203-4 printed electrode protection pads
SEC Sensor module enabling components for the first sensor module preferred embodiment
230 sensor module lock-in detection interface
231 sensor module identification interface SM ID
Main unit sensors' components MUSC for the first sensor module preferred embodiment:
122 contact microphone array
123 voice microphone
125 motion sensor
126 first electrocardiogram analogue front end ECG AFE component,
127 bio-impedance component,
132 ECG/BI electrode interface.
Second sensor module preferred embodiment SM2
  209-3 finger recess
  209-13 skin sensors' island's recess area
SC sensors' components for the second sensor module preferred embodiment
205-1, 205-2 pair of finger lateral electrodes
  205-1 first finger lateral electrode
  205-2 second finger lateral electrode
206-1, 206-2 pair of bottom electrodes
  206-1 first bottom electrode
  206-2 second bottom electrode
207 multi-function electrode
208 stethoscope 208
  208-1 stethoscope diaphragm
209 a skin sensor module optical area
  209-1 one or more sensor module optical sensors
  209-2 one or more forehead temperature sensors
210 sensor module multiplexer switch
226 second electrocardiogram analogue front end ECG AFE component
Sensor module enabling components SEC for the second sensor module preferred embodiment
211 USB port
221 high throughput wireless communication protocol module
  208-2 stethoscope audio output connector
  208-3 stethoscope contact microphone array
228 power supply
230 sensor module lock-in detection interface
231 sensor module identification interface SM ID
Main unit sensors' components MUSC for the second sensor module preferred embodiment
123 voice microphone
125 motion sensor
126 first electrocardiogram analogue front end ECG AFE component,
127 bio-impedance component,
132 ECG/BI electrode interface.
Third sensor module preferred embodiment SM3
sensors' components SC for the third sensor module preferred embodiment
205-1, 205-2 pair of finger lateral electrodes
  205-1 first finger lateral electrode
  205-2 second finger lateral electrode
208 stethoscope
  208-1 stethoscope diaphragm
  208-2 audio output connector
209 skin sensor module optical area
  209-1 one or more sensor module optical sensors
  209-2 one or more forehead temperature sensors
236 video camera area
  236-1 video camera
    236-11 detachable tongue depressor assembly
      236-111 tongue fixing frame
      236-112 tongue depressor
    236-12 detachable otoscope adaptor
      236-121 otoscope fixing frame
      236-122 otoscope
  236-2 infrared thermal imaging camera
  236-3 video camera area guiding recesses
  236-4 video camera area spring-loaded detent mechanism
  236-5 LEDs
239 images signal processor ISP
210 sensor module multiplexer switch
Sensor module enabling components SEC for the third sensor module preferred embodiment
211 USB port
221 high throughput wireless communication protocol module
208-2 stethoscope audio output connector
208-3 stethoscope contact microphone array
237 LCD touch display
  237-1 a multifunction lateral button
238 GSM eSIM module
228 power supply
230 sensor module lock-in detection interface
231 sensor module identification interface SM ID
Main unit sensors' components MUSC for the third sensor module preferred embodiment
123 voice microphone
125 motion sensor
126 first electrocardiogram analogue front end ECG AFE component,
127 bio-impedance component,
132 ECG/BI electrode interface.
Fourth sensor module preferred embodiment SM4
sensors' components SC for the fourth sensor module preferred embodiment
241 filter protection circuit
242 electrode analogic wire assembly
  242-1 electrode wires
  242-2 electrodes
  242-3 lead connector
245 body fixing clip
226 second electrocardiogram analogue front end ECG AFE component
Sensor module enabling components SEC for the fourth sensor module preferred embodiment
228 power supply
230 sensor module lock-in detection interface
231 sensor module identification interface SM ID
211 USB port
Main unit sensors' components MUSC for the fourth sensor module preferred embodiment
123 voice microphone 125 motion sensor
126 first electrocardiogram analogue front end ECG AFE component,
127 bio-impedance component,
132 ECG/BI electrode interface.
Fifth sensor module preferred embodiment SM5
sensors' components SC for the fifth sensor module preferred embodiment
232 electronic assembly electrode
   232-1 dry electrodes
      232-11 printed or polymer dry electrode pad
   232-2 electrical trace
233 flexible patient protection foil
   233-1 flexible patient protection foil first side
   233-2 flexible patient protection foil second side
      201-11 sensor module receptacle opening
240 textile elastic strap 240
   240-1 first side textile elastic strap
   240-2 second side textile elastic strap
Sensor module enabling components SEC for the fifth sensor module preferred embodiment
230 sensor module lock-in detection interface
231 sensor module identification interface SM ID
Main unit sensors' components MUSC for the fifth sensor module preferred embodiment
123 voice microphone
125 motion sensor
126 first electrocardiogram analogue front end ECG AFE component,
127 bio-impedance component,
132 ECG/BI electrode interface.
Sixth sensor module preferred embodiment SM6
sensors' components SC for the sixth sensor module preferred embodiment
205-1, 205-2 pair of finger lateral electrodes
   205-1 first finger lateral electrode
   205-2 second finger lateral electrode
109 skin sensors' island area
   109-1 one or more main unit optical sensors
      one or more light sources: 8 light emitting diodes LEDs from 109-111 to 109-118
      one or more light-detectors: 3 photodiodes from 109-121 to 109-123
      109-13 one or more light-transfer optical components
         109-141 one or more main unit temperature sensors from the one or more skin sensors' island sub-areas
d1, d2, d3, . . . dn light separation distance
206-3 wrist bottom electrode
Sensor module attaching means for the sixth sensor module preferred embodiment
   260 wrist silicone strap
Sensor module enabling components SEC for the sixth sensor module preferred embodiment
230 sensor module lock-in detection interface 230
231 sensor module identification interface 231 SM ID
Main unit sensors' components MUSC for the sixth sensor module preferred embodiment
123 voice microphone
125 motion sensor
126 first electrocardiogram analogue front end ECG AFE component,
127 bio-impedance component,
132 ECG/BI electrode interface.
Seventh sensor module preferred embodiment SM7
sensors' components SC for the seventh sensor module preferred embodiment
109 skin sensors' island area
   109-1 one or more main unit optical sensors
      one or more light sources: 8 light emitting diodes LEDs from 109-111 to 109-118
      one or more light-detectors: 3 photodiodes from 109-121 to 109-123
      109-13 one or more light-transfer optical components
         109-141 one or more main unit temperature sensors from the one or more skin sensors' island sub-areas
d1, d2, d3, . . . dn light separation distance
Sensor module attaching means for the seventh sensor module preferred embodiment
270 textile elastic strap
Sensor module enabling components SEC for the seventh sensor module preferred embodiment
230 sensor module lock-in detection interface
231 sensor module identification interface SM ID
Main unit sensors' components MUSC for the seventh sensor module preferred embodiment
125 motion sensor
Examples of external devices
255 external device 255
   255-1 USB cable
256 multiple charger device
   256-1 UV LEDs
   256-2 multiple charger device display

The invention claimed is:

1. A medical device for monitoring health parameters of a patient comprising a main unit (MU) electrically and mechanically connectable to a sensor module (SM),
when the sensor module (SM) is electrically and mechanically connected to the main unit (MU), the medical device is configured to acquire one or more bio-signals of the patient corresponding to an anatomic part of the patient, and the medical device is configured to carry out measurements of health parameters by means of configurations of the main unit (MU) and, respectively of the sensor module (SM),
the main unit (MU) comprises:
   main unit mechanical means (MMM) configured for detachable mechanical connection to a sensor module mechanical means (SMM) of the sensor module (SM),
   wherein the shape of the sensor module (SM) is configured to accommodate partially the main unit (MU) within a sensor module cavity of a sensor module receptacle of the sensor module (SM), and
   wherein the sensor module mechanical means (SMM) comprises:
      a guiding recess corresponding to a guiding element of the main unit for guiding the mechanical connection of the main unit (MU) within said sensor module cavity,
      two or more sensor module detent recesses, each sensor module detent recess corresponding to a spring-loaded detent of a spring-loaded detent mechanism,
   a main unit array interface (MUAI) configured for electrical connection to a sensor module array interface (SMAI) of the sensor module (SM), the main unit array interface (MUAI) comprising:
   main unit fixed-function electrical contacts,
   main unit multi-function electrical contacts, one or more programmable multiplexer switches,
one or more simple switches,
a processors' sub-unit (PSU), the processors' sub-unit (PSU) comprising:
a main processor, the main processor comprising communication drivers,
a memory,
main unit sensors' components (MUSC),
enabling components (EC), the enabling components (EC) comprising at least:
a lock-in detection interface,
an identification interface (SM ID),
the sensor module (SM) comprises:
sensors' components (SC), the sensors' components (SC) configured to carry out sensor module tasks,
the sensor module array interface (SMAI) arranged within the sensor module cavity, the sensor module array interface (SMAI) comprising:
sensor module fixed-function electrical contacts, or
sensor module multi-function contacts, or
sensor module fixed-function electrical contacts and sensor module multi-function contacts,
sensor module enabling components (SEC), the sensor module enabling components (SEC) comprising at least:
a sensor module lock-in detection interface, the sensor module lock-in detection interface configured to mate the lock-in detection interface of the main unit (MU),
a sensor module identification interface (SM ID), the sensor module (SM ID) identification interface configured to mate the identification interface (SM ID) of the main unit (MU),
[1] wherein the main unit fixed-function electrical contacts are configured to be connected to the sensor module fixed-function electrical contacts when the sensor module (SM) is mechanically connected to the main unit (MU), and the main unit multi-function electrical contacts are configured to be selectively connected to one of the three selected from the below list when the sensor module (SM) is mechanically connected to the main unit (MU):
to the sensor module multi-function contacts, or
to the sensor module fixed-function electrical contacts, or
to the sensor module multi-function contacts and the sensor module fixed-function electrical contacts,
[2] wherein the one or more simple switches are configured for connecting the main unit sensors' components (MUSC) and the enabling components (EC) to the main unit fixed-function electrical contacts, and the one or more programmable multiplexer switches are configured for selectively connecting the communication drivers and the enabling components (EC) to the main unit multi-function electrical contacts,
[3] wherein the lock-in detection interface is configured together with the sensor module lock-in detection interface to detect when the electrical and mechanical connection of the sensor module (SM) to the main unit (MU) is established, the identification interface (SM ID) is configured together with the sensor module identification interface (SM ID) to recognize the sensor module (SM) connected to the main unit (MU) and the associated sensor module tasks of said connected sensor module (SM), and

[4] wherein the processors' sub-unit (PSU) is configured to comprise pre-determined processors' instructions stored in the memory for the following:
instructions for detection of the sensor module (SM) when the sensor module (SM) is electrically and mechanically connected to the main unit (MU),
instructions for the recognition of the associated sensor module tasks,
instructions for selection of one or more specific sensor module tasks,
instructions for loading configuration for sensor module (SM), corresponding to one or more specific sensor module tasks,
instructions for connecting, by means of the one or more simple switches, the main unit sensors' components (MUSC) and the enabling components (EC) to the sensor module fixed-function electrical contacts, for the one or more selected specific sensor module tasks, according to the configuration,
instructions for selectively connecting, by means of the one or more programmable multiplexer switches, the communication drivers and the enabling components (EC) to the sensor module multi-function contacts or to the sensor module fixed-function electrical contacts, or to the sensor module multi-function contacts and the sensor module fixed-function electrical contacts, for the one or more selected specific sensor module tasks, according to the configuration,
instructions for processing the measurements,
instructions for storage of the processed measurements in the memory as a patient data file, and instructions for making available the measurements of health parameters to one or more external devices in order to be used for monitoring the health parameters of the patient,
instructions for electrically disconnecting of the main unit (MU) from the sensor module (SM).

2. The medical device of claim 1, wherein the main unit (MU) further comprises:
a skin sensors' island area, the skin sensors' island area comprising:
one or more main unit optical sensors, each of the one or more optical sensors comprising:
one or more light sources arranged to emit light through one or more light-transfer optical components,
one or more light-detectors, arranged to detect light through the one or more light-transfer optical components,
one or more skin sensors' island sub-areas comprising:
one or more main unit temperature sensors configured to sense through the one or more light-transfer optical components,
wherein each light-detector is spatially separated by each light source by a light separation distance (dn), each light-detector together with each light source are configured to generate a light path, the light separation distance (dn) being comprised between a pre-determined minimum light separation distance (MIN-dn) and a pre-determined maximum light separation distance (MAX-dn), the pre-determined minimum light separation distance (MIN-dn) and the pre-determined maximum light separation distance (MAX-dn), depending on a signal quality parameter such as the perfusion index of the anatomic part of the patient.

3. The medical device of claim 1, wherein the medical device further comprises means for identifying the patient including at least:
- a fingerprint biometric area, configured to acquire the unique identification characteristics of physical features data of the patient, and
- one or more biometric sensors included in the processors' sub-unit (PSSU), configured to identify the patient data file based on the physical features data acquired by the fingerprint biometric area.

4. The medical device of claim 1, wherein the processors' sub-unit (PSU) further comprises a wireless connection module, configured to connect the main unit (MU) to the one or more external devices in order to use the measurements for monitoring the health parameters of the patient.

5. The medical device of claim 1, wherein the sensor module (SM) further comprises:
sensor module attaching means:
- a flexible foil, the flexible foil having a flexible foil first side and a flexible foil second side, and the flexible foil second side configured for skin attachment on the chest of the patient,
- the sensor module receptacle fixed on the flexible foil first side, sensors' components (SC):
- a printed electronic assembly electrode, arranged on the flexible foil second side, the printed electronic assembly electrode configured to acquire electrical signals from the chest of the patient and configured to be connected to the sensor module fixed-function electrical contacts, the printed electronic assembly electrode comprising:
  - printed electrode pads, configured to acquire the electrical signals from the chest of the patient,
  - printed electrical trace for connecting the printed electrode pads to the sensor module fixed-function electrical contacts,
  - printed contacts protection pads, configured to protect and enhance the electrical contact of the printed electrical trace with the main unit fixed-function electrical contacts, and
the main unit sensors' components (MUSC) further comprise:
- a contact microphone array,
- a voice microphone,
- a motion sensor,
- a first electrocardiogram analogue front end (ECG AFE) component,
- a bio-impedance component, and
- an (ECG/BI) electrode interface.

6. The medical device of claim 5, wherein the sensor module fixed-function electrical contacts are arranged on a flexible electric contact support of the flexible foil second side, the sensor module receptacle has a sensor module receptacle opening, the flexible electric contact support and the sensor module receptacle opening are configured to enable the fetching of the sensor module fixed-function electrical contacts from the flexible foil second side to the flexible foil first side by folding said flexible electric contact support through said sensor module receptacle opening such that said sensor module fixed-function electrical contacts be in electrical contact with main unit fixed-function electrical contacts.

7. The medical device of claim 5, wherein the sensor module fixed-function electrical contacts are arranged on the flexible support, the flexible electric contact is arranged to be folded such that to enable the fetching of said sensor module fixed-function electrical contacts from the flexible foil second side to the electrode foil first side, the sensor module receptacle has a sensor module receptacle aperture, the sensor module receptacle aperture is positioned within the sensor module cavity, the sensor module receptacle aperture matching the size and position of the sensor module fixed-function electrical contacts arranged on the flexible electric contact support, the flexible electric contact support and the sensor module receptacle aperture are configured to enable said sensor module fixed-function electrical contacts to be in electrical contact with the main unit fixed-function electrical contacts.

8. The medical device of claim 5,
wherein the flexible foil is configured to accommodate an electric circuit stiffener for the sensor module fixed-function electrical contacts, the electric circuit stiffener configured to be mechanically and electrically secured on the flexible foil, the sensor module receptacle has a sensor module receptacle electric contacts aperture, the sensor module receptacle electric contacts aperture positioned within the sensor module cavity, the sensor module receptacle electric contacts aperture accommodating the sensor module fixed-function electrical contacts arranged on the electric circuit stiffener, the sensor module fixed-function electrical contacts arranged on the electric circuit stiffener, the electric circuit stiffener having two sides: a first electric circuit stiffener side, the first electric circuit stiffener side oriented towards the main unit (MU), and a second electric circuit stiffener side, the second electric circuit stiffener side oriented opposite the main unit (MU), the electric circuit stiffener provided with two-sides contact vias, each of the two-sides contact vias having a contact vias' first side and a contact vias' second side, and
wherein the first electric circuit stiffener side is configured to accommodate the sensor module fixed-function electrical contacts and the contact vias' first side, said contact vias' first side is configured to be in electrical contact with the sensor module fixed-function electrical contacts, the second electric circuit stiffener side is configured to be secured on the flexible foil first side and to accommodate the contact vias' second side, the contact vias' second side being in electrical contact with printed electrical vias by means of an electrically-conductive adhesive, the printed electrical vias are configured to be electrically connected with the printed electrical trace.

9. The medical device of claim 1, wherein the sensor module (SM) further comprises:
sensors' components (SC):
- a pair of finger lateral electrodes, arranged on opposite sides on the external surface of the sensor module receptacle, such that the pair of finger lateral electrodes be simultaneously in contact with a thumb finger and an index finger of the same hand of the patient, the pair of finger lateral electrodes configured to acquire bio-signals from the thumb finger and the index finger,
- a pair of bottom electrodes placed on the external surface of the sensor module receptacle, the pair of bottom electrodes, arranged such that to be simultaneously in contact to either the chest or the two thumb fingers for acquiring the corresponding bio-signals,
- a multi-function electrode placed on the external surface of the sensor module receptacle, configured to acquire bio-signals at least from the thumb or index fingers, the chest, and the knee join of the patient, the multi-function electrode arranged around the sensor module optical area,
a stethoscope, arranged inside the module receptacle, the stethoscope comprising a diaphragm placed on the external surface of the sensor module receptacle, centrally placed between the bottom electrodes, the stethoscope diaphragm configured to acquire lung or heart sounds,
a skin sensor module optical area, placed on the external surface of the sensor module receptacle, the skin sensor module optical area comprising:
one or more sensor module optical sensors (209-1),
one or more forehead temperature sensors,
a second electrocardiogram analogue front end (ECG AFE) component,
the main unit sensors' components (MUSC) further comprise:
a voice microphone,
a motion sensor,
a first electrocardiogram analogue front end (ECG AFE) component,
a bio-impedance component,
a (ECG/BI) electrode interface,
wherein the sensor module (SM) further comprises a sensor module multiplexer switch, the sensor module multiplexer switch configured to selectively connect the pair of finger lateral electrodes, the pair of bottom electrodes and the multi-function electrode to the second electrocardiogram analogue front end (ECG AFE) component and to the sensor module multi-function contacts and to the sensor module fixed-function electrical contacts creating one closed loop with the patient body from the list below:
a first closed loop configured for simultaneously acquiring and pre-processing the bio-signals from the thumb finger and an index finger from of the same hand by the pair of finger lateral electrodes and the index or the thumb finger from the other hand by the multi-function electrode,
a second closed loop configured for simultaneously acquiring and pre-processing the bio-signals from the chest by the pair of bottom electrodes, and by the multi-function electrode,
a third closed loop configured for simultaneously acquiring and pre-processing the bio-signals from the thumb fingers of both hands by the pair of bottom electrodes and the left knee join by the multi-function electrode, and
wherein the one or more programmable multiplexer switches are configured for selectively connecting the communication drivers and the enabling components (EC) to the sensor module multi-function contacts, the sensor module multi-function contacts corresponding to one of the closed loops, and/or to the sensors' components (SC), according to the selection of one option from the list:
i. the one or more sensor module optical sensors,
ii. the one or more forehead temperature sensors,
iii. the stethoscope,
iv. the first closed loop,
v. the second closed loop,
vi. the third closed loop,
vii. the first closed loop and the one or more sensor module optical sensors, and
viii. the second closed loop and the stethoscope.

10. The medical device of claim 1, wherein the sensor module (SM) further comprises:
sensors' components (SC):
a pair of finger lateral electrodes, arranged on opposite sides on the external surface of the sensor module receptacle such that the pair of finger lateral electrodes be simultaneously in contact with a thumb finger and an index finger of the same hand of the patient, the pair of finger lateral electrodes configured to acquire bio-signals from the thumb finger and an index finger,
a multi-function electrode placed on the external surface of the sensor module receptacle, configured to acquire bio-signals at least from the thumb or index fingers, and the knee join of the patient, the multi-function electrode arranged around the sensor module optical area,
a stethoscope, arranged inside the module receptacle, the stethoscope comprising a diaphragm placed on the external surface of the sensor module receptacle, the stethoscope diaphragm configured to acquire lung or heart sounds,
a skin sensor module optical area, placed on the external surface of the sensor module receptacle, the skin sensor module optical area comprising:
one or more sensor module optical sensors,
one or more forehead temperature sensors,
a second electrocardiogram analogue front end ECG AFE component,
a video camera, configured to acquire images from the throat and ears and the skin of the patient, the video camera comprising:
a detachable tongue depressor assembly configured to depress the tongue of the patient,
a detachable otoscope adaptor, configured to enhance the mechanical positioning of the video camera into the ear,
an infrared thermal imaging camera, configured to acquire thermal images from the patient's body,
an images signal processor (ISP), the images signal processor (ISP) configured to carry out intermediary processing of the images acquired from the video camera and from the infrared thermal imaging camera,
the main unit sensors' components (MUSC) further comprise:
a voice microphone,
a motion sensor,
a first electrocardiogram analogue front end (ECG AFE) component,
a bio-impedance component,
a (ECG/BI) electrode interface,
wherein the sensor module (SM) further comprises a sensor module multiplexer switch, the sensor module multiplexer switch configured to selectively connect the pair of finger lateral electrodes, and the multi-function electrode to the second electrocardiogram analogue front end (ECG AFE) component to the sensor module multi-function contacts and to the sensor module fixed-function electrical contacts creating one closed loop with the patient body from the list below:
a first closed loop configured for simultaneously acquiring and pre-processing the bio-signals from the thumb finger and an index finger from of the same hand by the pair of finger lateral electrodes and the index or the thumb finger from the other hand by the multi-function electrode, a second closed loop configured for simultaneously acquiring and pre-processing the bio-signals from the thumb fingers of both hands by the pair of finger lateral electrodes and from the left knee join or the left ankle by the multi-function electrode, and wherein the one or more programmable multiplexer switches are configured for selectively connecting the communication drivers and the enabling components (EC) to the sensor module multi-function contacts, the sensor module multi-function contacts corresponding to one of the closed loops, and/or to the sensors' components (SC), according to the selection of one option from the list:
  i. the one or more sensor module optical sensors,
  ii. the one or more forehead temperature sensors,
  iii. the stethoscope,
  iv. the first closed loop,
  v. the second closed loop,
  vi. the first closed loop and the one or more sensor module optical sensors,
  vii. the video camera, and
  viii. the infrared thermal imaging camera.

11. The medical device of claim 1, wherein the sensor module (SM) further comprises:
sensors' components (SC):
  one or more second electrocardiogram analogue front end (ECG AFE) components,
  one or more filter protection circuits, each filter protection circuit connected, respectively, to one second electrocardiogram analogue front end (ECG AFE) component,
  the one or more second electrocardiogram analogue front end (ECG AFE) components, and the corresponding one or more filter protection circuits arranged inside the sensor module receptacle,
  an electrode analogic wire assembly attachable to the sensor module receptacle by means of a lead connector,
  the lead connector configured to be electrically connected to the one or more electrocardiogram analogue front end (ECG AFE) components by means of the respective one or more filter protection circuits;
  the electrode analogic wire assembly comprising:
    a plurality of electrodes, at least two, preferable five for each electrocardiogram analogue front end (ECG AFE) component, the plurality of electrodes configured to acquire the electrical signals from the chest of the patient;
    the plurality of electrodes configured to be electrically connected through the lead connector to the filter protection circuits by means of a plurality of electrode wires, each electrode wire corresponding to one electrode from the plurality of electrodes,
the main unit sensors' components (MUSC) further comprise:
  a voice microphone,
  a motion sensor,
  a first electrocardiogram analogue front end (ECG AFE) component,
  a bio-impedance component, and
  an (ECG/BI) electrode interface, and
wherein the one or more programmable multiplexer switches are configured for selectively connecting the communication drivers and the enabling components (EC) to the sensor module multi-function contacts, the sensor module multi-function contacts corresponding to the one or more second electrocardiogram analogue front end (ECG AFE) components.

12. The medical device of claim 1,
wherein the sensor module (SM) further comprises:
sensors' components (SC):
  a dry electrodes assembly comprising dry electrodes, the dry electrodes configured to acquire bio-signals from the chest of the patient, and an electrical trace, the electrical trace configured to connect the dry electrodes with the sensor module fixed-function electrical contacts,
sensor module attaching means:
  a textile elastic strap, having:
    a textile elastic strap first side comprising means for attaching the sensor module receptacle,
    a textile elastic strap second side configured for accommodating the dry electrodes assembly,
  a flexible patient protection foil comprising:
    a flexible patient protection foil first side, the flexible patient protection foil first side arranged on the electrical trace,
    a flexible patient protection foil second side, the flexible patient protection foil second side accommodating a flexible electric contact support,
wherein the sensor module fixed-function electrical contacts are arranged on the flexible electric contact support, the sensor module receptacle comprises a sensor module receptacle opening, the sensor module receptacle opening being configured to enable the fetching of the sensor module fixed-function electrical contacts from the flexible patient protection foil second side to the flexible patient protection foil first side by folding said flexible electric contact support through said sensor module receptacle opening such that said sensor module fixed-function electrical contacts be in electrical contact with main unit fixed-function electrical contacts,
the main unit sensors' components (MUSC) further comprise:
  a contact microphone array,
  a voice microphone,
  a motion sensor,
  a first electrocardiogram analogue front end (ECG AFE) component,
  a bio-impedance component,
  an (ECG/BI) electrode interface,
the main unit (MU) comprises:
  a skin sensors' island area, the skin sensors' island area comprising:
    one or more main unit optical sensors, each of the one or more optical sensors comprising:
      one or more light sources arranged to emit light through one or more light-transfer optical components,
      one or more light-detectors, arranged to detect light through the one or more light-transfer optical components,
    one or more skin sensors' island sub-areas, comprising:
      one or more main unit temperature sensors configured to sense through the one or more light-transfer optical components,
wherein each light-detector is spatially separated by each light source by a light separation distance (dn), each light-detector together with each light source are configured to generate a light path, the light separation distance (dn) is comprised between a pre-determined minimum light separation distance (MIN-dn) and a pre-determined maximum light separation distance (MAX-dn), the pre-determined minimum light separation distance (MIN-dn) and the pre-determined maximum light separation distance (MAX-dn) being configured for chest measurements, wherein the sensor module receptacle opening is configured to accommodate the skin sensors' island area, and wherein when the main unit fixed-function electrical contacts are connected to the sensor module fixed-function electrical contacts, the dry electrodes assembly is configured to acquire and pre-process the bio-signals from the chest of the patient, and the skin sensors' island area is configured to acquire the bio-signals from the chest of the patient.

13. The medical device of claim 1,
wherein the main unit sensors' components (MUSC) further comprises:
a voice microphone,
a motion sensor,
a first electrocardiogram analogue front end (ECG AFE) component,
a bio-impedance component,
an (ECG/BI) electrode interface,
the main unit (MU) further comprises:
a skin sensors' island area, the skin sensors' island area comprising:
one or more main unit optical sensors, each of the one or more optical sensors comprising:
one or more light sources arranged to emit light through one or more light-transfer optical components,
one or more light-detectors, arranged to detect light through the one or more light-transfer optical components,
one or more skin sensors' island sub-areas, comprising:
one or more main unit temperature sensors configured to sense through the one or more light-transfer optical components,
wherein each light-detector is spatially separated by each light source by a light separation distance (dn), each light-detector together with each light source are configured to generate a light path, the light separation distance (dn) is comprised between a pre-determined minimum light separation distance (MIN-dn) and a pre-determined maximum light separation distance (MAX-dn), the pre-determined minimum light separation distance (MIN-dn) and the pre-determined maximum light separation distance (MAX-dn) being configured for wrist measurements, and wherein the sensor module receptacle opening is configured to accommodate the skin sensors' island area, the sensor module (SM) further comprises:
sensors' components (SC):
a pair of finger lateral electrodes, arranged on opposite sides on the external surface of the sensor module receptacle such that the pair of finger lateral electrodes be simultaneously in contact with a thumb finger and an index finger of the same hand of the patient, the pair of finger lateral electrodes configured to acquire bio-signals from the thumb finger and an index finger,
a wrist bottom electrode placed on the external surface of the sensor module receptacle, configured to acquire bio-signals from the wrist of the second hand of the patient, the wrist bottom electrode arranged around the skin sensors' island area,
sensor module attaching means:
a wrist silicone strap comprising means for attaching the sensor module receptacle, and
wherein when the main unit fixed-function electrical contacts are connected to the sensor module fixed-function electrical contacts, the pair of finger lateral electrodes and the wrist bottom electrode are configured to create a closed loop configured for simultaneously acquiring and pre-processing the bio-signals from the thumb finger and an index finger from of the same hand by the pair of finger lateral electrodes and from the wrist by the wrist bottom electrode of the second hand, the skin sensors' island area is configured to acquire the bio-signals from the wrist.

14. The medical device of claim 1,
wherein the sensor module (SM) further comprises:
the main unit sensors' components (MUSC) further comprise:
a motion sensor,
the main unit (MU) further comprises:
a skin sensors' island area, the skin sensors' island area comprising:
one or more main unit optical sensors, each of the one or more optical sensors comprising:
one or more light sources arranged to emit light through one or more light-transfer optical components,
one or more light-detectors, arranged to detect light through the one or more light-transfer optical components,
one or more skin sensors' island sub-areas, comprising:
one or more main unit temperature sensors configured to sense through the one or more light-transfer optical components,
wherein each light-detector is spatially separated by each light source by a light separation distance (dn), each light-detector together with each light source are configured to generate a light path, the light separation distance (dn) is comprised between a pre-determined minimum light separation distance (MIN-dn) and a pre-determined maximum light separation distance (MAX-dn), the pre-determined minimum light separation distance (MIN-dn) and the pre-determined maximum light separation distance (MAX-dn) being configured for arm measurements,
sensor module attaching means:
a textile elastic strap comprising means for attaching the sensor module receptacle,
wherein the sensor module receptacle opening is configured to accommodate the skin sensors' island area, and
wherein when the main unit fixed-function electrical contacts are connected to the sensor module fixed-function electrical contacts, the skin sensors' island area is configured to acquire the bio-signals from the arm.

15. A computer-implemented method of monitoring health parameters of a patient using the medical device configured to carry out measurements of health parameters according to claim 1, the method comprising the following steps:
S1 electrically and mechanically connecting of the main unit (MU) of the medical device to a selected sensor module (SM) of the medical device, S2 detecting the electrical and mechanical connection between the main unit (MU) and the sensor module (SM) by the lock-in detection interface together with the sensor module lock-in detection interface, S3 recognizing the associated sensor module tasks of the sensor module (SM) by the identification interface (SM ID) together with the sensor module identification interface (SM ID), S4 selecting by the processors' sub-unit (PSU) one or more specific sensor module tasks from the sensor module tasks S5 loading configuration for the sensor module (SM) by the processors' sub-unit (PSU) corresponding to the one or more specific sensor module tasks, S6 Simultaneously, at the instructions received from the processors' sub-unit (PSU), for the one or more selected specific sensor module tasks:

electrically connecting the main unit sensors' components (MUSC) and the enabling components (EC) to the sensor module fixed-function electrical contacts, according to the configuration, electrically connecting the communication drivers to the sensor module multi-function contacts or to the sensor module fixed-function electrical contacts, or to the sensor module multi-function contacts and to the sensor module fixed-function electrical contacts, according to the configuration, S7 acquiring by the medical device of the one or more bio-signals from an anatomic part of the patient, S8 processing the one or more bio-signals and outputting the measurements of health parameters by the main processor of the processors' sub-unit (PSU), S9 storing the measurements of health parameters in a memory as a patient data file to be used for monitoring health parameters of the patient, and making available by the processors' sub-unit (PSU) of the measurements of health parameters to one or more external devices in order to be used for monitoring the health parameters of the patient, S10 electrically and mechanically disconnecting of the main unit (MU) from the sensor module (SM).

16. The method of claim 15, wherein the method of the invention comprises one further sub-step in step 1 after or during carrying out step 1 of the method, placing the finger of the patient on a fingerprint biometric area, and the method of the invention comprises one further sub-step in step 5 before the loading of the configuration for the selected sensor module (SM) by the processors' sub-unit (PSU):

patient authentication by means of a fingerprint biometric area and one or more biometric sensors and loading a corresponding patient configuration.

17. A non-transitory computer-readable storage medium encoded with a computer program, the computer program comprising instructions executable by the medical device for monitoring health parameters of a patient of claim 1, which, upon such execution by the medical device, causes the medical device to perform operations of the method for monitoring health parameters of the patient according to claim 15.

18. The storage medium of claim 17, wherein the computer program comprises instructions to perform operations of the method for monitoring at least the following health parameters of the patient: a blood pressure, a blood oxygenation rate, glucose level, a heart rate, a body temperature, an electrocardiogram wave form representing the electrical heart activity, sounds of the heart, sounds of the lungs, sounds of the abdomen, images from the throat, images from the ears, images from the skin, thermal images from the patient's body, as well as combinations thereof.

* * * * *